(12) United States Patent
Park et al.

(10) Patent No.: US 10,011,586 B2
(45) Date of Patent: Jul. 3, 2018

(54) HETEROCYCLIC COMPOUND, METHOD FOR PREPARING THE SAME, AND PHARMACEUTICAL COMPOSITION COMPRISING THE SAME

(71) Applicant: Daewoong Pharmaceutical Co., Ltd., Gyeonggi-do (KR)

(72) Inventors: Joon Seok Park, Gyeonggi-do (KR); Youn Jung Yoon, Gyeonggi-do (KR); Min Jae Cho, Gyeonggi-do (KR); Ho Bin Lee, Seoul (KR); Ja Kyung Yoo, Gyeonggi-do (KR); Bong Yong Lee, Seoul (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/556,352

(22) PCT Filed: Jun. 7, 2016

(86) PCT No.: PCT/KR2016/005999
§ 371 (c)(1),
(2) Date: Sep. 7, 2017

(87) PCT Pub. No.: WO2016/200116
PCT Pub. Date: Dec. 15, 2016

(65) Prior Publication Data
US 2018/0044322 A1 Feb. 15, 2018

(30) Foreign Application Priority Data
Jun. 8, 2015 (KR) .................. 10-2015-0080722

(51) Int. Cl.
*C07D 401/06* (2006.01)
*C07D 417/14* (2006.01)
*C07D 401/14* (2006.01)
*C07D 471/04* (2006.01)

(52) U.S. Cl.
CPC ......... *C07D 401/06* (2013.01); *C07D 401/14* (2013.01); *C07D 417/14* (2013.01); *C07D 471/04* (2013.01)

(58) Field of Classification Search
CPC .. C07D 401/06; C07D 401/14; C07D 417/14; C07D 471/04
USPC ........................................ 514/303
See application file for complete search history.

(56) References Cited

U.S. PATENT DOCUMENTS

2017/0088551 A1* 3/2017 Park ..................... C07D 473/40

FOREIGN PATENT DOCUMENTS

| WO | WO-2010/019210 A2 | 2/2010 |
| WO | WO-2010/096170 A2 | 8/2010 |
| WO | WO-2013/106702 A1 | 7/2013 |

OTHER PUBLICATIONS

"Opinion of the Scientific Panel on Additives and Products or Substances Used in Animal Feed on a Request From the Commission on the re-Evaluation of Coccidiostat Stenorol in Accordance with Article 9G of Council Directive 70/524/EEC", The EFSA Journal 8, 2003, pp. 1-45.
McLaughlin et al., "Dihydroxylation of Vinyl Sulfones: Stereoselective Synthesis of (+)- and (−)-Febrifugine and Halofuginone", J. Org. Chem. 75, 2010, pp. 518-521.
Kim et. el., "Aminoacyl-tRNA Synthetases and Tumorigenesis: More Than Housekeeping", Nature Reviews Cancer, vol. 11, Oct. 2011, pp. 708-718.
Cui et al., "Efficient One-Pot Synthesis of 2-substituted Benzimidazoles From Triacyloxyborane Intermediates", Synlett, vol. 23, 2012, pp. 247-250.
Bava et al., "CPEB1 Coordinates Alternative 3'-UTR Formation With Translational Regulation", Nature, 2013, 7 pages.
Roy et al., "One-Pot Sequential Syntheses of 1, 2-disubstituted Benzimidazoles Under Metal-Free Conditions", Tetrahedron Letters, vol. 54, No. 38, 2013, pp. 5243-5245.
Carlson et al., "Halofuginone-induced Amino Acid Starvation Regulates Stat3-dependent Th17 Effector Function and Reduces Established Autoimmune Inflammation", J. Immunol., Jan. 31, 2014, 10 pages.
Park et al., "Halofuginone Ameliorates Autoimmune Arthritis in Mice by Regulating the Balance Between Th17 and Treg Cells and Inhibiting Osteoclastogenesis", Arthritis & Rheumatology, vol. 66, No. 5, May 2014, pp. 1195-1207.
Mark Pines, "Halofuginone for Fibrosis, Regeneration and Cancer in the Gastrointestinal Tract", World Journal of Gastroenterology, vol. 20, Issue 40, Oct. 28, 2014, pp. 14778-14786.
McLaughlin et al., "The Chemistry and Biology of Febrifugine and Halofuginone", Bioorganic & Medicinal Chemistry, vol. 22, 2014, pp. 1993-2004.
Search Report and Written Opinion in International Application No. PCT/KR2016/005999 dated Oct. 20, 2016, 14 pages.

\* cited by examiner

*Primary Examiner* — Daniel R Carcanague
(74) *Attorney, Agent, or Firm* — Marshall, Gerstein & Borun LLP

(57) ABSTRACT

The present invention relates to a heterocyclic compound having a novel structure that can be used in the prevention or treatment of diseases caused by abnormality in a PRS (prolyl-tRNA synthetase) activity, a method for preparing the same, and a pharmaceutical composition comprising the same.

12 Claims, No Drawings

HETEROCYCLIC COMPOUND, METHOD FOR PREPARING THE SAME, AND PHARMACEUTICAL COMPOSITION COMPRISING THE SAME

TECHNICAL FIELD

The present invention relates to a heterocyclic compound having a novel structure that can be used in the prevention or treatment of diseases caused by abnormality in a PRS (prolyl-tRNA synthetase) activity, a method for preparing the same, and a pharmaceutical composition comprising the same.

BACKGROUND OF ART

PRS (prolyl-tRNA synthetase) is one of the aminoacyl-tRNA synthetase (ARS) family and serves to activate an amino acid for protein synthesis. That is, ARS performs a translational function to form aminoacyl adenylate (AA-AMP) and then transfer the activated amino acid to the 3-end of the corresponding tRNA. Since ARS plays an important role in the synthesis of protein, If ARS is inhibited, the growth of all cells is suppressed. Thus, ARS has been recognized as a promising target for a therapeutic agent for treating diseases that should suppress antibiotics or cell overexpression (Nature, 494:121-125).

PRS is present in, or functions as, a multisynthetase complex (MSC) in the form of EPRS (Glutamyl-Prolyl-tRNA Synthetase). In particular, among various MSCs, EPRS functions as a translational silencer that suppresses the production of VEGF (vascular endothelial growth factor A) which is a key factor in angiogenesis. In addition, it is reported that EPRS is closely related with various solid tumors (Nat. Rev. Cancer, 2011, 11, 708-718).

The only substance, known as the PRS inhibitor, is halofuginone. Halofuginone is a derivative of febrifugine derived from natural products and has anti-malarial effects and various anti-inflammatory effects. It can also be used as an animal feed additive. Currently, halofuginone is being clinically studied as anti-cancer agent, an anti-inflammatory agent (J Immunol, 2014, 192(5), 2167-76), therapeutic agents for the treatment of autoimmune diseases (Arthritis Rheumatol, 2014,66 (5), 1195-207), and therapeutic agents for the treatment of fibrosis diseases (World J Gastroenterol, 2014,20 (40), 14778-14786) (Bioorg. Med. Chem. 2014, 22, 1993-2004).

However, it has been reported that halofuginone acts on various targets and has a very severe toxicity and further there is a risk of genotoxicity (The EFSA Journal, 2003, 8: 1-45). Therefore, discovering PRS inhibitors having higher safety to the human body among substances capable of inhibiting PRS like halofuginone has a significance in terms of developing an anti-cancer agent of the next generation that can be used as an antifibrosis agent, an anti-inflammatory agent, an autoimmune therapeutic agent alone or in combination with an existing targeted anti-cancer agent.

In this regard, the present inventors have conducted numerous studies to develop a novel compound with reduced toxicity while having a PRS enzyme inhibitory effect, and found that the compound having a novel structure which will be described later selectively inhibits the PRS, thereby completing the present invention. The compounds belonging to the present invention themselves have mainly a PRS enzyme inhibitory activity, but do not exclude a possibility of exhibiting a pharmacological action as an efficacious agent by a special body environment or by products of metabolic process, after absorption into the body.

DETAILED DESCRIPTION OF THE INVENTION

Technical Problem

The present invention provides a heterocyclic compound having a novel structure that can be used in the prevention or treatment of cancers, inflammatory diseases, autoimmune diseases or fibrosis, a method for preparing the same, and a pharmaceutical composition comprising the same.

Technical Solution

In order to achieve the above objects, the present invention provides a compound represented by the following Chemical Formula 1, or a pharmaceutically acceptable salt thereof:

[Chemical Formula 1]

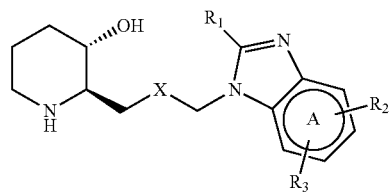

wherein:
A is a benzene ring, or a pyridine ring,
X is CO, or CHOH,
$R_1$ is hydrogen, or C1-4 hydroxyalkyl,
$R_2$ is phenyl, pyrazolyl, pyridin-2-onyl, pyrrolidinyl, or thiazolyl,
  wherein $R_2$ is unsubstituted or substituted by one or two substituents each independently selected from the group consisting of $C_{1-4}$ alkyl, $C_{1-4}$ alkoxy, $C_{1-4}$ haloalkyl, halogen and cyano, and
$R_3$ is hydrogen, or $C_{1-4}$ alkyl.
Preferably, A, together with an imidazole ring fused to A, forms a structure of

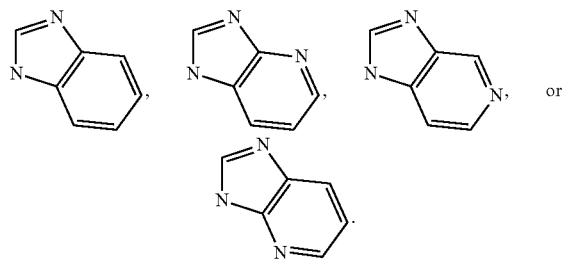

Also preferably, $R_1$ is hydrogen, or hydroxymethyl.
Also preferably, $R_2$ is a phenyl unsubstituted or substituted by one or two substituents each independently selected from the consisting of $C_{1-4}$ alkyl, $C_{1-4}$ alkoxy, $C_{1-4}$ haloalkyl, halogen and cyano; an unsubstituted pyrazolyl; an unsubstituted pyridin-2-onyl; an unsubstituted pyrrolidinyl; or an unsubstituted thiazolyl.

Also preferably, R₂ is unsubstituted or substituted by one or two substituents each independently selected from methyl, methoxy, trifluoromethyl, fluoro, chloro and cyano.

Also preferably, R₃ is hydrogen, or methyl.

Also preferably,

A is benzene ring,

X is CO, or CHOH,

R₁ is hydrogen, or C₁₋₄ hydroxyalkyl,

R₂ is phenyl, pyrazolyl, pyridin-2-onyl, or thiazolyl,
wherein R₂ is unsubstituted or substituted by one or two substituents each independently selected from the group consisting of C₁₋₄ alkyl, C₁₋₄ alkoxy, C₁₋₄ haloalkyl, halogen and cyano; and R₃ is hydrogen, or C₁₋₄ alkyl.

Also preferably, A, together with an imidazole ring fused to A, forms

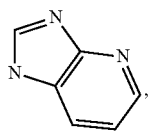

X is CO,

R₁ is hydrogen,

R₂ is phenyl,
wherein R₂ is substituted by C₁₋₄ haloalkyl, or halogen, and

R₃ is hydrogen.

Also preferably, A, together with an imidazole ring fused to A, forms

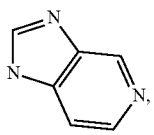

X is CO,

R₁ is hydrogen,

R₂ is phenyl, or pyrrolidinyl,
wherein R₂ is unsubstituted or substituted by one or two substituents each independently selected from C₁₋₄ haloalkyl and halogen, and R₃ is hydrogen.

Also preferably, A, together with an imidazole ring fused to A, forms

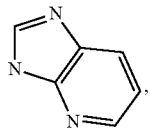

X is CO, or CHOH,

R₁ is hydrogen,

R₂ is phenyl,
wherein R₂ is substituted by C₁₋₄ haloalkyl or halogen, and R₃ is hydrogen.

Representative examples of the compounds represented by Chemical Formula 1 are as follows:

1) 1-((2R,3S)-3-hydroxypiperidin-2-yl)-3-(4-phenyl-1H-benzo[d]imidazol-1-yl)propan-2-one,
2) 1-(4-(3-fluorophenyl)-1H-imidazo[4,5-c]pyridin-1-yl)-3-((2R,3S)-3-hydroxypiperidin-2-yl)propan-2-one,
3) 1-(4-(3-chlorophenyl)-1H-imidazo[4,5-c]pyridin-1-yl)-3-((2R,3S)-3-hydroxypiperidin-2-yl)propan-2-one,
4) 1-((2R,3S)-3-hydroxypiperidin-2-yl)-3-(4-(3-(trifluoromethyl)phenyl)-1H-imidazo[4,5-c]pyridin-1-yl)propan-2-one,
5) 1-(4-(3-chloro-5-fluorophenyl)-1H-imidazo[4,5-c]pyridin-1-yl)-3-((2R,3S)-3-hydroxypiperidin-2-yl)propan-2-one,
6) 1-(4-(3,5-dichlorophenyl)-1H-imidazo[4,5-c]pyridin-1-yl)-3-((2R,3S)-3-hydroxypiperidin-2-yl)propan-2-one,
7) 1-((2R,3S)-3-hydroxypiperidin-2-yl)-3-(4-(pyrrolidin-1-yl)-1H-imidazo[4,5-c]pyridin-1-yl)propan-2-one,
8) 1-((2R,3S)-3-hydroxypiperidin-2-yl)-3-(5-phenyl-1H-benzo[d]imidazol-1-yl)propan-2-one,
9) 1-(5-(2-fluorophenyl)-1H-imidazo[4,5-b]pyridin-1-yl)-3-((2R,3S)-3-hydroxypiperidin-2-yl)propan-2-one,
10) 1-(5-(3-fluorophenyl)-1H-imidazo[4,5-b]pyridin-1-yl)-3-((2R,3S)-3-hydroxypiperidin-2-yl)propan-2-one,
11) 1-(5-(4-fluorophenyl)-1H-imidazo[4,5-b]pyridin-1-yl)-3-((2R,3S)-3-hydroxypiperidin-2-yl)propan-2-one,
12) 1-(5-(3-chlorophenyl)-1H-imidazo[4,5-b]pyridin-1-yl)-3-((2R,3S)-3-hydroxypiperidin-2-yl)propan-2-one,
13) 1-((2R,3S)-3-hydroxypiperidin-2-yl)-3-(5-(3-(trifluoromethyl)phenyl)-1H-imidazo[4,5-b]pyridin-1-yl)propan-2-one,
14) 1-(6-(3-chlorophenyl)-3H-imidazo[4,5-b]pyridin-3-yl)-3-((2R,3S)-3-hydroxypiperidin-2-yl)propan-2-one,
15) 1-((2R,3S)-3-hydroxypiperidin-2-yl)-3-(6-(3-(trifluoromethyl)phenyl)-3H-imidazo[4,5-b]pyridin-3-yl)propan-2-one,
16) 1-(5-(3-fluorophenyl)-4-methyl-1H-benzo[d]imidazol-1-yl)-3-((2R,3S)-3-hydroxypiperidin-2-yl)propan-2-one,
17) 1-(5-(3-chlorophenyl)-4-methyl-1H-benzo[d]imidazol-1-yl)-3-((2R,3S)-3-hydroxypiperidin-2-yl)propan-2-one,
18) 1-(5-(2-chlorophenyl)-4-methyl-1H-benzo[d]imidazol-1-yl)-3-((2R,3S)-3-hydroxypiperidin-2-yl)propan-2-one,
19) 1-(5-(4-chlorophenyl)-4-methyl-1H-benzo[d]imidazol-1-yl)-3-((2R,3S)-3-hydroxypiperidin-2-yl)propan-2-one,
20) 3-(1-(3-((2R,3S)-3-hydroxypiperidin-2-yl)-2-oxopropyl)-4-methyl-1H-benzo[d]imidazol-5-yl)benzonitrile,
21) 1-((2R,3S)-3-hydroxypiperidin-2-yl)-3-(4-methyl-5-(3-(trifluoromethyl)phenyl)-1H-benzo[d]imidazol-1-[d]propan-2-one,
22) 1-((2R,3S)-3-hydroxypiperidin-2-yl)-3-(5-(3-methoxyphenyl)-4-methyl-1H-benzo[d]imidazol-1-yl)propan-2-one,
23) 1-((2R,3S)-3-hydroxypiperidin-2-yl)-3-(4-methyl-5-(thiazol-4-yl)-1H-benzo[d]imidazol-1-yl)propan-2-one,
24) 1-((2R,3S)-3-hydroxypiperidin-2-yl)-3-(6-phenyl-1H-benzo[d]imidazol-1-yl)propan-2-one,
25) 1-(6-(3-fluorophenyl)-1H-benzo[d]imidazol-1-yl)-3-((2R,3S)-3-hydroxypiperidin-2-yl)propan-2-one,
26) 1-(6-(2-chlorophenyl)-1H-benzo[d]imidazol-1-yl)-3-((2R,3S)-3-hydroxypiperidin-2-yl)propan-2-one,
27) 1-(6-(3-chlorophenyl)-1H-benzo[d]imidazol-1-yl)-3-((2R,3S)-3-hydroxypiperidin-2-yl)propan-2-one,
28) 1-(6-(4-chlorophenyl)-1H-benzo[d]imidazol-1-yl)-3-((2R,3S)-3-hydroxypiperidin-2-yl)propan-2-one,
29) 1-((2R,3S)-3-hydroxypiperidin-2-yl)-3-(6-(3-(trifluoromethyl)phenyl)-1H-benzo[d]imidazol-1-yl)propan-2-one,
30) 1-((2R,3S)-3-hydroxypiperidin-2-yl)-3-(6-(m-tolyl)-1H-benzo[d]imidazol-1-yl)propan-2-one, 31) 1-(6-(3,5-dichlorophenyl)-1H-benzo[d]imidazol-1-yl)-3-((2R,3S)-3-hydroxypiperidin-2-yl)propan-2-one,
32) 1-(6-(3-chloro-5-fluorophenyl)-1H-benzo[d]imidazol-1-yl)-3-((2R,3S)-3-hydroxypiperidin-2-yl)propan-2-one,
33) 1-(6-(3-chloro-4-fluorophenyl)-1H-benzo[d]imidazol-1-yl)-3-((2R,3S)-3-hydroxypiperidin-2-yl)propan-2-one,
34) 1-(6-(3-chloro-5-methylphenyl)-1H-benzo[d]imidazol-1-yl)-3-((2R,3S)-3-hydroxypipendin-2-yl)propan-2-one,
35) 1-(6-(3-chloro-5-methoxyphenyl)-1H-benzo[d]imidazol-1-yl)-3-((2R,3S)-3-hydroxypipendin-2-yl)propan-2-one,
36) 3-chloro-5-(1-(3-((2R,3S)-3-hydroxypiperidin-2-yl)-2-oxopropyl)-1H-benzo[d]imidazol-6-yl)benzonitrile,
37) 1-(6-(1H-pyrazol-4-yl)-1H-benzo[d]imidazol-1-yl)-3-((2R,3S)-3-hydroxypiperidin-2-yl)propan-2-one,
38) 1-(6-(1H-pyrazol-3-yl)-1H-benzo[d]imidazol-1-yl)-3-((2R,3S)-3-hydroxypiperidin-2-yl)propan-2-one,
39) 1-((2R,3S)-3-hydroxypiperidin-2-yl)-3-(6-(thiazol-4-yl)-1H-benzo[d]imidazol-1-yl)propan-2-one,
40) 5-(1-(3-((2R,3S)-3-hydroxypipendin-2-yl)-2-oxopropyl)-1H-benzo[d]imidazol-6-yl)pyridin-2(1H)-one,
41) 1-(6-(3-chlorophenyl)-1H-imidazo[4,5-b]pyridin-1-yl)-3-((2R,3S)-3-hydroxypipendin-2-yl)propan-2-one,
42) 1-((2R,3S)-3-hydroxypiperidin-2-yl)-3-(6-(3-(trifluoromethyl)phenyl)-1H-imidazo[4,5-b]pyridin-1-yl)propan-2-one,
43) 1-(5-(2-fluorophenyl)-3H-imidazo[4,5-b]pyridin-3-yl)-3-((2R,3S)-3-hydroxypiperidin-2-yl)propan-2-one,
44) 1-(5-(3-fluorophenyl)-3H-imidazo[4,5-b]pyridin-3-yl)-3-((2R,3S)-3-hydroxypiperidin-2-yl)propan-2-one,
45) 1-(5-(4-fluorophenyl)-3H-imidazo[4,5-b]pyridin-3-yl)-3-((2R,3S)-3-hydroxypiperidin-2-yl)propan-2-one,
46) 1-(5-(3-chlorophenyl)-3H-imidazo[4,5-b]pyridin-3-yl)-3-((2R,3S)-3-hydroxypiperidin-2-yl)propan-2-one,
47) 1-((2R,3S)-3-hydroxypipendin-2-yl)-3-(5-(3-(trifluoromethyl)phenyl)-3H-imidazo[4,5-b]pyridin-3-yl)propan-2-one,
48) 1-((2R,3S)-3-hydroxypiperidin-2-yl)-3-(7-phenyl-1H-benzo[d]imidazol-1-yl)propan-2-one,
49) 1-(7-(3-fluorophenyl)-1H-benzo[d]imidazol-1-yl)-3-((2R,3S)-3-hydroxypipendin-2-yl)propan-2-one,
50) 1-(7-(3-chlorophenyl)-1H-benzo[d]imidazol-1-yl)-3-((2R,3S)-3-hydroxypiperidin-2-yl)propan-2-one,
51) 1-(7-(4-chlorophenyl)-1H-benzo[d]imidazol-1-yl)-3-((2R,3S)-3-hydroxypipendin-2-yl)propan-2-one,
52) 1-((2R,3S)-3-hydroxypipendin-2-yl)-3-(7-(2-(trifluoromethyl)phenyl)-1H-benzo[d]imidazol-1-yl)propan-2-one,
53) 1-((2R,3S)-3-hydroxypipendin-2-yl)-3-(7-(3-(trifluoromethyl)phenyl)-1H-benzo[d]imidazol-1-yl)propan-2-one,
54) 1-((2R,3S)-3-hydroxypipendin-2-yl)-3-(7-(4-(trifluoromethyl)phenyl)-1H-benzo[d]imidazol-1-yl)propan-2-one,
55) 1-(2-(hydroxymethyl)-5-phenyl-1H-benzo[d]imidazol-1-yl)-3-((2R,3S)-3-hydroxypipendin-2-yl)propan-2-one,
56) 1-(5-(3-fluorophenyl)-2-(hydroxymethyl)-1H-benzo[d]imidazol-1-yl)-3-((2R,3S)-3-hydroxypiperidin-2-yl)propan-2-one,
57) 1-(2-(hydroxymethyl)-6-phenyl-1H-benzo[d]imidazol-1-yl)-3-((2R,3S)-3-hydroxypipendin-2-yl)propan-2-one,
58) 1-(6-(2-fluorophenyl)-2-(hydroxymethyl)-1H-benzo[d]imidazol-1-yl)-3-((2R,3S)-3-hydroxypiperidin-2-yl)propan-2-one,
59) 1-(6-(3-fluorophenyl)-2-(hydroxymethyl)-1H-benzo[d]imidazol-1-yl)-3-((2R,3S)-3-hydroxypiperidin-2-yl)propan-2-one,
60) 1-(6-(4-fluorophenyl)-2-(hydroxymethyl)-1H-benzo[d]imidazol-1-yl)-3-((2R,3S)-3-hydroxypiperidin-2-yl)propan-2-one,
61) 1-(2-(hydroxymethyl)-6-(3-(trifluoromethyl)phenyl)-1H-benzo[d]imidazol-1-yl)-3-((2R,3S)-3-hydroxypiperidin-2-yl)propan-2-one,
62) (2R,3S)-2-(3-(6-(3-chlorophenyl)-1H-benzo[d]imidazol-1-yl)-2-hydroxypropyl)piperidin-3-ol, and
63) (2R,3S)-2-(3-(5-(3-chlorophenyl)-3H-imidazo[4,5-b]pyridin-3-yl)-2-hydroxypropyl)piperidin-3-ol.

Further, the compounds represented by Chemical Formula 1 may be used in the form of a pharmaceutically acceptable salt, and as the salt, an acid addition salt formed by a pharmaceutically acceptable free acid is useful. As the free acid, an inorganic acid and an organic acid may be used. Examples of the inorganic acid may include hydrochloric acid, bromic acid, sulfuric acid, phosphoric acid, and the like. Examples of the organic acid may include citric acid, acetic acid, lactic acid, maleic acid, gluconic acid, methanesulfonic acid, succinic acid, 4-toluene sulfonic acid, glutamic acid, aspartic acid or the like.

Salts or solvates of the compounds represented by Chemical Formula 1 that are pharmaceutically not acceptable can be used as intermediates in the preparation of the compound represented by Chemical Formula 1, a pharmaceutically acceptable salt or solvate thereof.

The compound represented by Chemical Formula 1 according to the present invention includes pharmaceutically acceptable salts thereof as well as all solvates and hydrates which can be prepared therefrom. The salts or solvates of the compound represented by Chemical Formula 1 can be prepared from the compounds represented by Chemical Formula 1 using conventional methods in the technical field to which the present invention pertains.

Also, the compound represented by Chemical Formula 1 according to the present invention can be prepared in crystalline form or non-crystalline form. When the compound represented by Chemical Formula 1 is produced in crystalline form, it may be optionally hydrated or solvated. The present invention may include not only stoichiometric hydrates of the compound represented by Chemical Formula 1 but also compounds containing a various amount of water. The solvates of the compound represented by Chemical Formula 1 according to the present invention include both stoichiometric solvates and non-stoichiometric solvates.

The present invention also provides a method for preparing a compound represented by Chemical Formula 1 as shown in the following Reaction Scheme 1:

[Reaction Scheme 1]

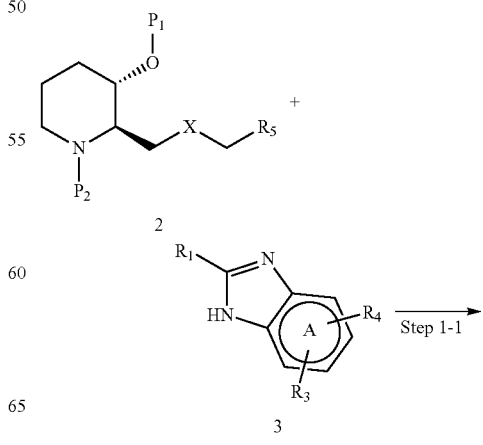

-continued

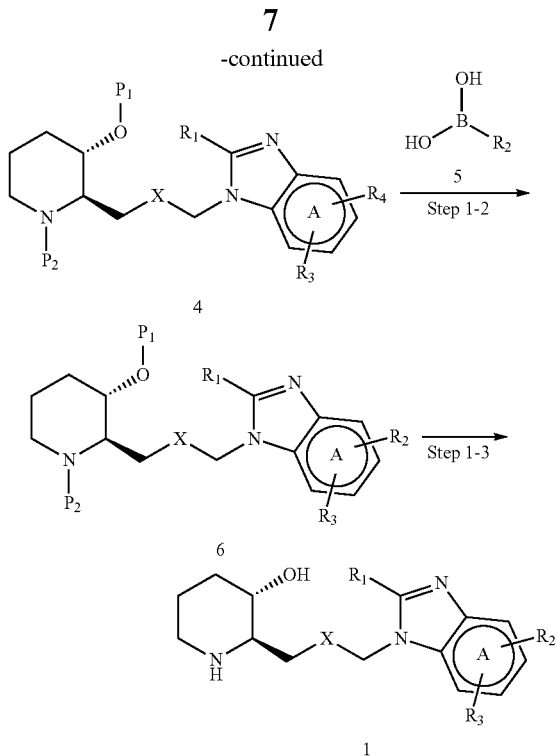

(in Reaction Scheme 1, A, X, $R_1$, $R_2$ and $R_3$ are as previously defined, $R_4$ and $R_5$ are each independently halogen, and $P_1$ and $P_2$ means each independently a protecting group. The protecting group can be (tert-butyldimethylsilyl)oxy, or benzyloxycarbonyl.)

The step 1-1 is a step of preparing a compound represented by Chemical Formula 4 by reacting a compound represented by Chemical Formula 2 with a compound represented by Chemical Formula 3 in the presence of a base. Conventional inorganic bases and organic bases can be used as the base. Non-limiting examples of the organic bases may include diisopropyl ethyl amine and triethyl amine. Non-limiting examples of the inorganic bases may include potassium carbonate, sodium carbonate, sodium hydrogen carbonate, cesium carbonate, or calcium carbonate. Also, the reaction may be carried out in a polar solvent such as methanol, ethanol, butanol, tetrahydrofuran, acetone, toluene, dimethylformamide, dimethylformsulfoxide, chloroform, dioxane, acetonitrile diethyl ether, or dichloromethane at 20° C. to 150° C. for 10 minutes to 24 hours.

The step 1-2 is a step of preparing a compound represented by Chemical Formula 6 by reacting a compound represented by Chemical Formula 4 and a compound represented by Chemical Formula 5 with a catalyst of tetrakis(triphenylphosphine)palladium, (1,1'-bis(diphenylphosphino)ferrocene)palladium dichloride or tris(dibenzylideneacetone)dipalladium in the presence of inorganic bases such as potassium carbonate, sodium carbonate, potassium cesium or sodium hydrogen carbonate. The reaction may be carried out in a polar solvent such as methanol, ethanol, tert-butanol, tetrahydrofuran, toluene, dioxane, dimethylformamide, ethylene glycol dimethyl ether, or water at 70° C. to 150° C. for 5 minutes to 18 hours.

The step 1-3 is a step of preparing a compound represented by Chemical Formula 1 by reacting a compound represented by Chemical Formula 6 in the presence of an acid. Non-limiting examples of the acid may include hydrochloric acid, bromic acid, hydrofluoric acid, trifluoroacetic acid or the like. Preferably, the reaction solvent may or may not use a polar organic solvent. Preferably, when using a polar organic solvent, dichloromethane, chloroform, toluene, dimethylformamide, dioxane, tetrahydrofuran or the like may be used, and the reaction can be carried out at room temperature to 100° C. for 10 minutes to 6 hours.

As another example, the compound represented by Chemical Formula 1 where $R_1$ is hydrogen can be prepared as shown in the following Reaction Scheme 2:

[Reaction Scheme 2]

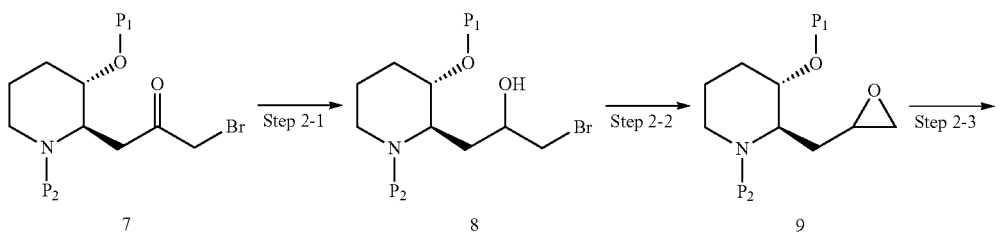

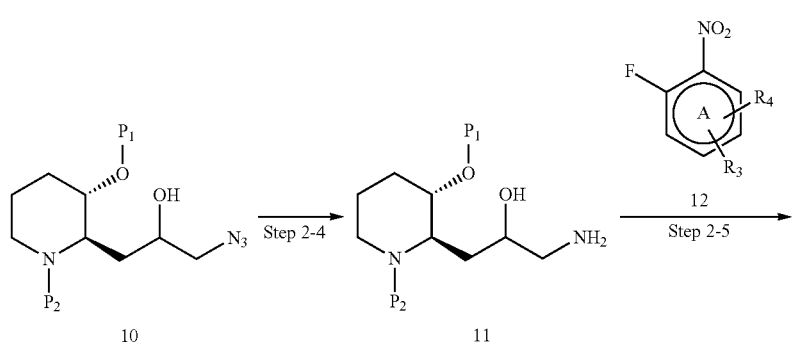

-continued

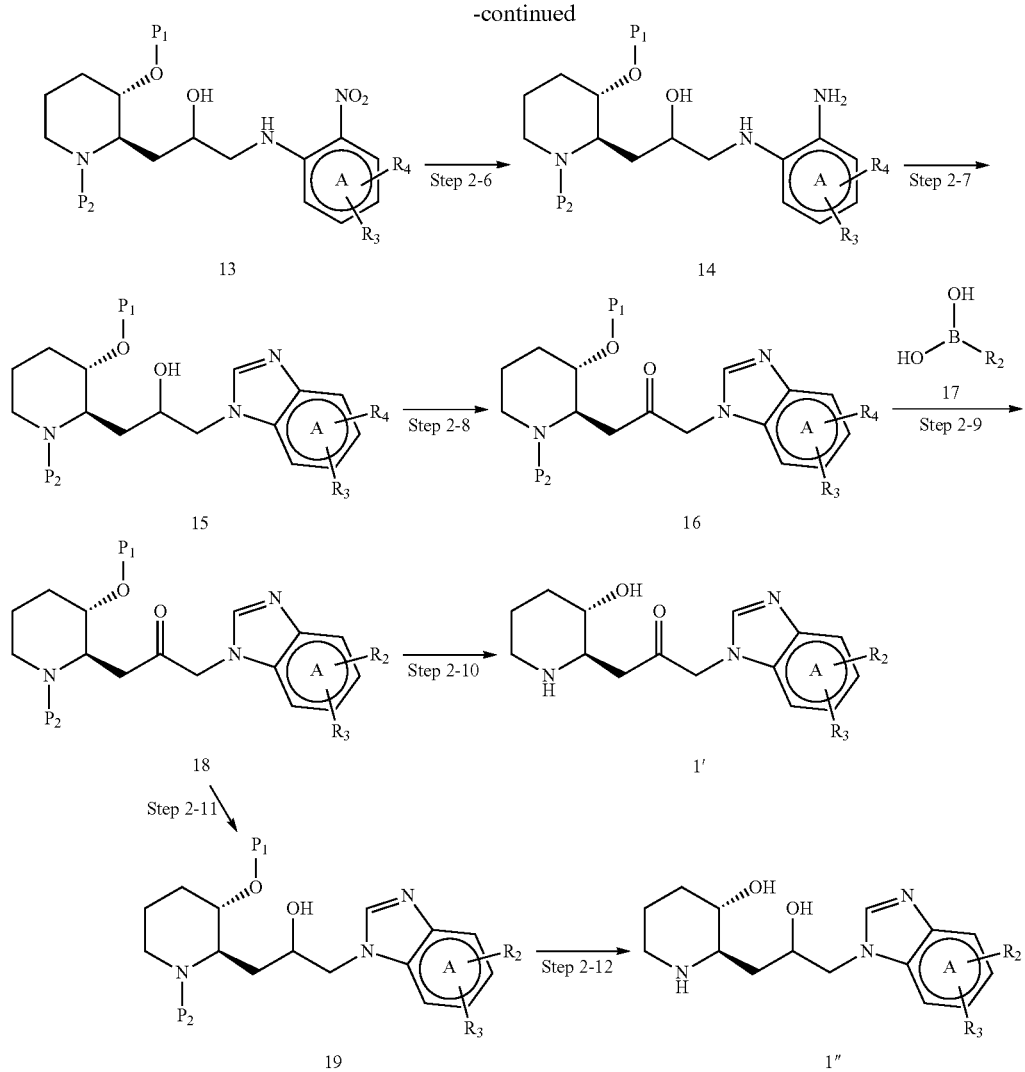

(in Reaction Scheme 2, A, $R_2$ and $R_3$ are as defined above, $R_4$ is halogen, and $P_1$ and $P_2$ means each independently a protecting group. The protecting group can be tert-butyldimethylsilyl)oxy, or benzyloxycarbonyl.)

The step 2-1 is a step of preparing a compound represented by Chemical Formula 8 by reacting a compound represented by Chemical Formula 7 in the presence of a base. The compound represented by Chemical Formula 7 can be produced according to a known method (e.g., McLaughlin and Evans, J Org. Chem, 2010, 75: 518-521), but is not limited thereto. Conventional inorganic bases can be used as the base, but non-limiting examples thereof may include sodium borohydride, lithium aluminum hydride, sodium carbonate, sodium formate, cerium chloride, borane-tetrahydrofuran. Further, the reaction may be carried out in a polar solvent such as methanol, ethanol, tetrahydrofuran, acetone, toluene, diethyl ether, or dichloromethane at −78° C. to 20° C. for 10 minutes to 12 hours.

The step 2-2 is a step of preparing a compound represented by Chemical Formula 9 by reacting a compound represented by Chemical Formula 8 in the presence of a base. A conventional inorganic base can be used as the base, and non-limiting examples thereof may include potassium hydroxide, lithium hydride, potassium fluoride, sodium hydride, sodium ethoxide, potassium carbonate, or potassium tert-butoxide. In addition, the reaction may be carried out in a polar solvent such as methanol, tetrahydrofuran, acetone, dioxane, diethyl ether, dichloromethane, dimethylformamide, or acetonitrile, at 0° C. to 20° C. for 10 minutes to 24 hours.

The step 2-3 is a step of preparing a compound represented by Chemical Formula 10 by reacting a compound represented by Chemical Formula 9 under acidic conditions in the presence of sodium azide and/or trimethylsilyl azide. Conventional inorganic acids and organic acids can be used as the acid, and non-limiting examples thereof may include ammonium chloride, tetrabutylammonium chloride, p-toluenesulfonic acid, acetic acid, hydrochloric acid, or sulfuric acid. Further, the reaction can be carried out in a polar solvent such as methanol, ethanol, tert-butanol, acetone, dimethylformamide, acetonitrile, or water at 20° C. to 100° C. for 10 minutes to 48 hours.

The step 2-4 is a step of preparing a compound represented by Chemical Formula 11 by reacting a compound represented by Chemical Formula 10 in the presence of a base. Conventional inorganic bases can be used as the base, and non-limiting examples thereof may include sodium borohydride, lithium aluminum hydride, palladium, nickel, or triphenylphosphine. Further, the reaction may be carried out in a polar solvent such as methanol, ethanol, tetrahydrofuran, acetone, toluene, dioxane, dimethylformamide, acetonitrile, diethyl ether, dichloromethane, or water at 20° C. to 80° C. for 10 minutes to 18 hours.

The step 2-5 is a step of preparing a compound represented by Chemical Formula 13 by reacting a compound represented by Chemical Formula 11 and a compound represented by Chemical Formula 12 in the presence of a base. Conventional inorganic bases and organic bases can be used as the base. Non-limiting examples of the organic base may include diisopropylethylamine or triethylamine, and non-limiting examples of the inorganic base may include potassium carbonate, sodium carbonate, sodium hydrogen carbonate, cesium carbonate, or calcium carbonate. Further, the reaction may be carried out in a polar solvent such as methanol, ethanol, butanol, tetrahydrofuran, acetone, toluene, dimethylformamide, dimethylformsulfoxide at 20° C. to 150° C. for 10 minutes to 24 hours.

The step 2-6 is a step of preparing a compound represented by Chemical Formula 14 by reacting a compound represented by Chemical Formula 13 in the presence of hydrogen and metal. Non-limiting examples of the metal may include palladium, nickel, or platinum oxide. Further, the reaction can be carried out in a polar solvent such as methanol, ethanol, isopropanol, tetrahydrofuran, dimethylformamide, ethyl acetate, dichloromethane, or water at 5° C. to 50° C. for 10 minutes to 12 hours.

The step 2-7 is a step of preparing a compound represented by Chemical Formula 15 by reacting a compound represented by Chemical Formula 14 i) in the presence of trimethyl orthoformate or triethyl orthoformate, and para toluenesulfonic acid or pyridinium para toluenesulfonate, or ii) in the presence of formic acid. The reaction may be carried out in a polar solvent such as methanol, ethanol, tetrahydrofuran, toluene, dioxane, dimethylformamide, acetone, chloroform, ethyl acetate, dichloromethane, or acetonitrile at 20° C. to 120° C. for 10 minutes to 12 hours.

The step 2-8 is a step of preparing a compound represented by Chemical Formula 16 by reacting a compound represented by Chemical Formula 15 with an oxidizing agent. Non-limiting examples of the oxidizing agent may include Dess-Martin periodinane, hydrogen peroxide, or oxaly chloride. Further, the reaction can be carried out in a polar solvent such as dichloromethane, dimethylformamide, dimethylformsulfoxide, toluene, chloroform, tetrahydrofuran, acetone, acetonitrile diethylether, or ethyl acetate at −78° C. to 30° C. for 10 minutes to 12 hours.

The step 2-9 is a step of preparing a compound represented by Chemical Formula 18 by reacting a compound represented by Chemical Formula 16 with a compound represented by Chemical Formula 17 in the presence of a catalyst of tetrakis(triphenylphosphine)palladium, (1,1'-bis(diphenylphosphino)ferrocene)palladium dichloride or tris(dibenzylideneacetone)dipalladium, and an inorganic base of potassium carbonate, sodium carbonate, cesium potassium or sodium hydrogen carbonate. The reaction is carried out in a polar solvent such as methanol, ethanol, tert-butanol, tetrahydrofuran, toluene, dioxane, dimethylformamide, ethylene glycol dimethyl ether, or water at 70° C. to 150° C. for 5 minutes to 18 hours.

The step 2-10 is a step of preparing a compound represented by Chemical Formula 1' by reacting a compound represented by Chemical Formula 18 in the presence of an acid. Non-limiting examples of the acid may include hydrochloric acid, bromic acid, hydrofluoric acid, trifluoroacetic acid or the like. Preferably, the reaction solvent may use or not use a polar organic solvent. Preferably, when using a polar organic solvent, dichloromethane, chloroform, toluene, dimethylformamide, dioxane, tetrahydrofuran or the like can be used, and the reaction can be carried out at room temperature to 100° C. for 10 minutes to 6 hours.

The step 2-11 is a step of preparing a compound represented by Chemical Formula 19 by reacting a compound represented by Chemical Formula 18 in the presence of a base. Conventional inorganic bases can be used as the base, and non-limiting examples thereof may include sodium borohydride, lithium aluminium hydride, sodium carbonate, sodium formate, cerium chloride, or borane-tetrahydrofuran. Further, the reaction may be carried out in a polar solvent such as methanol, ethanol, tetrahydrofuran, acetone, toluene, diethyl ether, or dichloromethane at −78° C. to 20° C. for 10 minutes to 12 hours.

The step 2-12 is a step of preparing a compound represented by Chemical Formula 1" by reacting a compound represented by Chemical Formula 19 in the presence of an acid. Non-limiting examples of the acid may include hydrochloric acid, bromic acid, hydrofluoric acid, trifluoroacetic acid or the like. Preferably, the reaction solvent may use or may not use a polar organic solvent. Preferably, when using a polar organic solvent, dichloromethane, chloroform, toluene, dimethylformamide, dioxane or tetrahydrofuran can be used, and the reaction may be carried out at room temperature to 100° C. for 10 minutes to 6 hours.

As another example, the compound represented by Chemical Formula 1 where $R_1$ is $C_{1-4}$ hydroxyalkyl can be prepared, for example, as shown in the following Reaction Scheme 3:

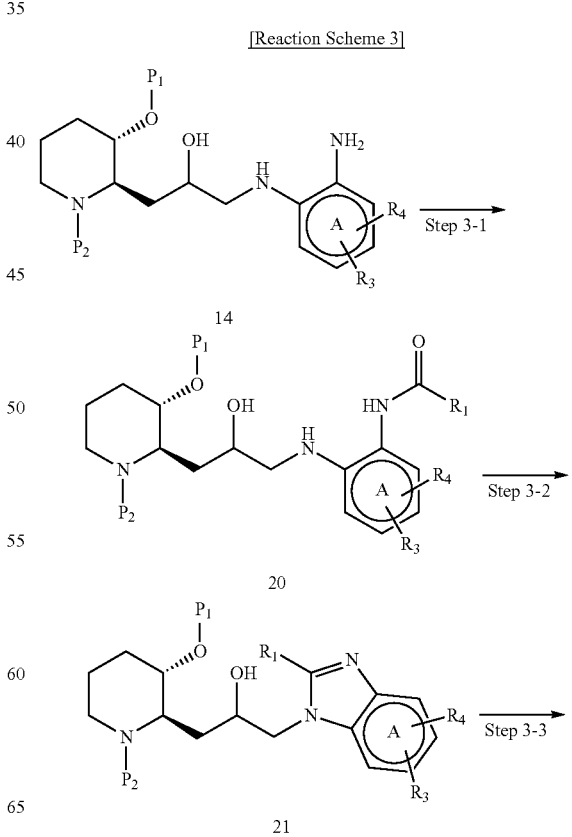

-continued

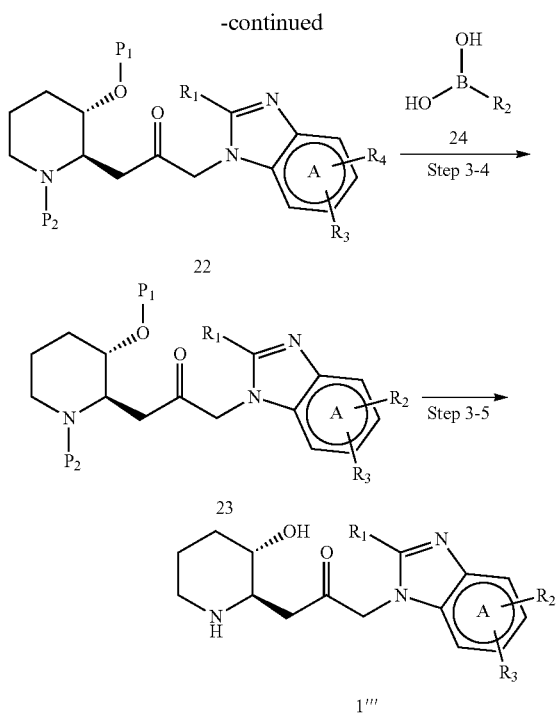

(in Reaction Scheme 3, A, X, $R_2$ and $R_3$ are as defined above, $R_4$ is halogen, and $P_1$ and $P_2$ means each independently a protecting group. The protecting group can be (tert-butyldimethylsilyl)oxy, or benzyloxycarbonyl.)

The step 3-1 is a step of preparing a compound represented by Chemical Formula 20 by reacting a compound represented by Chemical Formula 14 and $R_1$-substituted carboxylic acid ($R_1$—COOH) in the presence of an amide coupling reagent of bis-(2-oxo-3-oxazolydinyl)phosphoryl hydrochloride, 1-ethyl-(3-(3-dimethylamino)propyl)-carbodiimide hydrochloride, benzotriazol-1-yloxy-tris-(pyrrolidino)phosphonium hexafluorophosphate, benzotriazole-ol, (benzotriazol-1-yloxy)tris(dimethylamino)phosphonium hexafluorophosphate or O-(benzotriazol-1-yl)-N,N,N,N'-tetramethyluronium hexafluorophosphate, and a base of triethylamine, di-isopropyl ethylamine, pyridine, dimethylaniline, dimethylamino pyridine or sodium hydroxide. The reaction may be carried out in a polar solvent such as methanol, ethanol, propanol, tetrahydrofuran, toluene, dioxane, dimethylformamide, dichloromethane, acetonitrile, or acetone at −20° C. to 80° C. for 5 minutes to 18 hours.

The step 3-2 is a step of preparing a compound represented by Chemical Formula 21 by reacting a compound represented by Chemical Formula 20 i) in the presence of trimethyl orthoformate or triethyl orthoformate, and para toluenesulfonic acid or pyridinium paratoluenesulfonate, or ii) in the presence of formic acid. The reaction may be carried out in a polar solvent such as methanol, ethanol, tetrahydrofuran, toluene, dioxane, dimethylformamide, acetone, chloroform, ethyl acetate, dichloromethane, or acetonitrile at 20° C. to 120° C. for 10 minutes to 12 hours.

The step 3-3 is a step of preparing a compound represented by Chemical Formula 22 by reacting a compound represented by Chemical Formula 21 with an oxidizing agent. Non-limiting examples of the oxidizing agent may include Dess-Martin periodinane, hydrogen peroxide, or oxalyl chloride. Further, the reaction may be carried out in a polar solvent such as dichloromethane, dimethylformamide, dimethylformsulfoxide, toluene, chloroform, tetrahydrofuran, acetone, acetonitrile diethylether, or ethyl acetate at −78° C. to 30° C. for 10 minutes to 12 hours.

The step 3-4 is a step of preparing a compound represented by Chemical Formula 23 by reacting a compound represented by Chemical Formula 22 with a compound represented by Chemical Formula 24 in the presence of a catalyst such as tetrakis(triphenylphosphine)palladium, (1,1'-bis (diphenylphosphino)ferrocene)palladium dichloride or tris(dibenzylideneacetone)dipalladium, and an inorganic base such as potassium carbonate, sodium carbonate, cesium potassium or sodium hydrogen carbonate. The reaction may be carried out in a polar solvent such as methanol, ethanol, tert-butanol, tetrahydrofuran, toluene, dioxane, dimethylformamide, ethylene glycol dimethyl ether, or water at 70° C. to 150° C. for 5 minutes to 18 hours.

The step 3-5 is a step of preparing a compound represented by Chemical Formula 1′′′ by reacting a compound represented by Chemical Formula 23 in the presence of an acid. Non-limiting examples of the acid may include hydrochloric acid, bromic acid, hydrofluoric acid, trifluoroacetic acid or the like. Preferably, the reaction solvent may use or may not use a polar organic solvent. Preferably, when using a polar organic solvent, dichloromethane, chloroform, toluene, dimethylformamide, dioxane, tetrahydrofuran or the like may be used, and the reaction may be carried out at room temperature to 100° C. for 10 minutes to 6 hours.

In addition, the present invention provides a compound represented by Chemical Formula 16 or a compound represented by Chemical Formula 21 as an intermediate which can be used in the preparation of the compound represented by Chemical Formula 1.

[Chemical Formula 16]

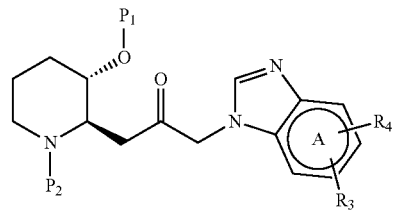

[Chemical Formula 21]

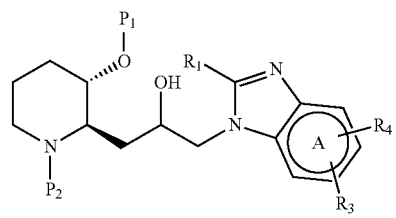

in Chemical Formulae 16 and 21,
$P_1$ and $P_2$ are each independently a protecting group,
A, $R_1$ and $R_3$ are as defined in Chemical Formula 1, and
$R_4$ is halogen.
Preferably, $P_1$ and $P_2$ are each independently (tert-butyldimethylsilyl)oxy, or benzyloxycarbonyl.
Also preferably, $R_4$ is bromo, chloro, or fluoro.
The compound represented by Chemical Formula 16 can be prepared by the step 2-5 through step 2-8 of the above-mentioned Reaction Scheme 2. Also, the compound represented by Chemical Formula 21 can be prepared by the steps 3-1 and 3-2 of the above-mentioned Reaction Scheme 3.

In addition, the present invention provides a pharmaceutical composition for the prevention or treatment of diseases caused by abnormal PRS (prolyl-tRNA synthetase) activity, comprising a compound represented by Chemical Formula 1 or a pharmaceutically acceptable salt thereof.

The compound represented by Chemical Formula 1 according to the present invention can inhibit PRS enzymatic activity and thus can be used in the prevention or treatment of diseases caused by abnormality in a PRS (prolyl-tRNA synthetase) activity. Examples of diseases caused by abnormality in the PRS (prolyl-tRNA synthetase) activity may include a cancer, an inflammatory disease, an autoimmune disease and a fibrosis.

As shown in Examples which will be described below, the compound represented by Chemical Formula 1 according to the present invention can significantly inhibit PRS enzymatic activity and also inhibit the growth of cancer cells. Thus, this compound may be effectively used in the prevention or treatment of the diseases.

The pharmaceutical composition according to the present invention can be formulated in types for oral or parenteral administrations according to a standard pharmaceutical practice. These formulations may contain additives such as pharmaceutically acceptable carrier, adjuvant or diluent in addition to the active ingredient. Suitable carriers may include, for example, physiological saline, polyethylene glycol, ethanol, vegetable oil, and isopropyl myristate, and the diluent may include, for example, lactose, dextrose, sucrose, mannitol, sorbitol, cellulose and/or glycine, but are not limited thereto. Further, the compounds of the present invention can be dissolved in oils, propylene glycol or other solvents which are usually used in the preparation of injectable solutions. In addition, the compounds of the present invention may be formulated as ointments or creams for topical application.

A preferred dose of the compound represented by Chemical Formula 1 according to the present invention may be varied according to the condition and weight of a patient, the severity of a disease, the type of a drug, and the route and duration of administration, but it may be suitably selected by those skilled in the art. In order to achieve the desirable effects, however, the compound of the present invention may be administrated daily at a dose of 0.0001 to 100 mg/kg (body weight), and preferably 0.001 to 100 mg/kg (body weight). The administration may be performed once a day or in divided doses each day through an oral or parenteral route.

Depending on the method of administration, the pharmaceutical composition according to the present invention may contain the compound represented by Chemical Formula 1 or a pharmaceutically acceptable salt thereof in an amount of 0.001 to 99% by weight, preferably 0.01 to 60% by weight.

The pharmaceutical composition of the present invention may be administered to mammals such as a rat, a mouse, a domestic animal, a human or the like, through various routes. The administration may be carried out through all possible methods, for example, oral, rectal, intravenous, intramuscular, subcutaneous, intra-endometrial or intracerebroventricular injection.

Advantageous Effects

As set forth above, the compound represented by Chemical Formula 1 according to the present invention can inhibit PRS enzymatic activity and thus may be effectively used in the prevention or treatment of diseases caused by abnormality in a PRS (prolyl-tRNA synthetase) activity, for example, cancers, inflammatory diseases, autoimmune diseases and fibrosis.

DETAILED DESCRIPTION OF THE EMBODIMENTS

Below, the present invention will be described in more detail by way of examples. However, these examples are provided only for illustration of the present invention, and should not be construed as limiting the scope of the present invention to these examples.

EXAMPLE 1

Preparation of 1-((2R,3S)-3-hydroxypiperidin-2-yl)-3-(4-phenyl-1H-benzo[d]imidazol-1-yl)propan-2-one

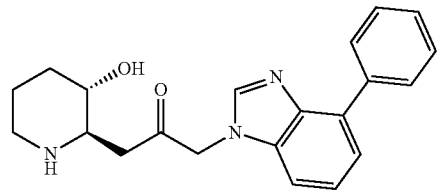 [SMILES: O=C(C[C@H]1NCCC[C@@H]1O)Cn1cnc2c(-c3ccccc3)cccc21]

Step 1-1: Preparation of benzyl (2R,3S)-2-(3-bromo-2-hydroxypropyl)-3-((tert-butyldimethylsilyl)oxy)piperidine-1-carboxylate Benzyl (2R,3S)-2-(3-bromo-2-oxopropyl)-3-((tert-butyldimethylsilyl)oxy)piperidine-1-carboxylate (5 g, 10.32 mmol) was dissolved in a mixed solvent of methanol and tetrahydrofuran (1:1) (20 mL, 0.5 M) and then cooled to 0° C. Then, sodium borohydride (390 mg, 10.32 mmol) was added thereto and stirred at 0° C. for 30 minutes. The temperature was raised to room temperature and the mixture was additionally stirred for 12 hours. When the reaction was completed, subsequent reactions were carried out without work-up and purification procedures.

Step 1-2: Preparation of benzyl (2R,3S)-3-((tert-butyldimethylsilyl)oxy)-2-(oxiren-2-ylmethyl)piperidine-1-carboxylate Potassium hydroxide (203 mg, 3.61 mmol) dissolved in a small amount of water was added to benzyl (2R,3S)-2-(3-bromo-2-hydroxypropyl)-3-((tert-butyldimethylsilyl)oxy) piperidine-1-carboxylate reaction solution obtained from Step 1-1, and then stirred at room temperature for 1 hour. When the reaction was completed, the solvent was removed, and the resulting mixture was diluted with ethyl acetate and then washed with saturated sodium chloride solution. The organic layer was collected, dried over magnesium sulfate, filtered and then concentrated under reduced pressure, and purified by column chromatography (hexane:ethyl acetate=4:1) to give the title compound (3.4 g, two step yield: 81%).

Step 1-3: Preparation of benzyl (2R,3S)-2-(3-azido-2-hydroxypropyl)-3-(tert-butyldimethylsilyl)oxy) piperidine-1-carboxylate Benzyl (2R,3S)-3-((tert-butyldiemthylsilyl)oxy)-2-(oxiren-2-ylmethyl)piperidine-1-carboxylate (3.4 g, 8.38 mmol) obtained from Step 1-2 was dissolved in a mixed solvent of methanol and water (8:1) (90 mL, 0.09 mmol), to which sodium azide (2.7 g, 41.92 mmol) and ammonium chloride (1.3 g, 25.15 mmol) were added and then stirred under reflux at 70° C. for 6 hours. When the reaction was completed, the resulting mixture was diluted with ethyl acetate and then washed with saturated sodium chloride solution. The organic layer was collected, dried over magnesium sulfate, filtered and then concentrated under reduced pressure, and purified by column chromatography (hexane:ethyl acetate=3:1) to give the title compound (3.8 g, yield: 98%).

Step 1-4: Preparation of benzyl (2R,3S)-2-(3-amino-2-hydroxypropyl)-3-((tert-butyldiemthylsilyl)oxy)piperidine-1-carboxylate Benzyl (2R,3S)-2-(3-azido-2-hydroxypropyl)-3-((tert-butyldimethylsilyl)oxy)piperidine-1-carboxylate (1.5 g, 3.34 mmol) obtained from Step 1-3 was dissolved in a mixed solvent of tetrahydrofuran and water (8:2) (50 mL, 0.08 M) to which triphenyl phosphine (1.8 g, 6.69 mmol) was added and stirred at room temperature for 6 hours. When the reaction was completed, the resulting mixture was diluted with ethyl acetate and washed with saturated sodium chloride solution. The organic layer was collected, dried over magnesium sulfate, filtered and then concentrated under reduced pressure, and purified by column chromatography (dichloromethane:methanol=9:1) to give the title compound (1.2 g, yield: 81%).

Step 1-5: Preparation of benzyl (2R,3S)-2-(3-((3-bromo-2-nitrophenyl)amino)-2-hydroxypropyl)-3-((tert-butyldimethylsilyl)oxy)piperidine-1-carboxylate Benzyl (2R,3S)-2-(3-amino-2-hydroxypropyl)-3-((tert-butyldiemthylsilyl)oxy)piperidine-1-carboxylate (120 mg, 0.27 mmol) obtained from Step 1-4 was dissolved in N,N-dimethylformamide (1 mL, 0.3 M) to which 1-bromo-3-fluoro-2-nitrobenzene (59 mg, 0.27 mmol) and diisopropyl ethyl amine (94 mg, 0.54 mmol) were added and then stirred under reflux at 80° C. for 6 hours. When the reaction was completed, the solvent was removed and the resulting mixture was diluted with ethyl acetate and washed with saturated sodium chloride solution. The organic layer was collected, dried over magnesium sulfate, filtered and then concentrated under reduced pressure, and purified by column chromatography (hexane:ethylacetate=2:1) to give the title compound (120 mg, yield: 71%).

Step 1-6: Preparation of benzyl (2R,3S)-2-(3-((2-amino-2-bromophenyl)amino)-2-hydroxypropyl)-3-((tert-butyldimethylsilyl)oxy)piperidine-1-carboxylate Benzyl (2R,3S)-2-(3-((3-bromo-2-nitrophenyl)amino)-2-hydroxypropyl)-3-((tert-butyldimethylsilyl)oxy)piperidine-1-carboxylate (120 mg, 0.19 mmol) obtained from Step 1-5 was dissolved in methanol (6 mL, 0.03 M) to which an appropriate amount of Raney nickel was added. After connecting a hydrogen balloon, the mixture was stirred at room temperature for 1 hour. When the reaction was completed, the reaction solution was filtered with a celite and concentrated under reduced pressure. Subsequent reactions were carried out without purification procedure.

Step 1-7: Preparation of benzyl (2R,3S)-2-(3-((4-bromo-1H-benzo[d]imidazol-1-yl)-2-hydroxypropyl)-3-((tert-butyldimethylsilyl)oxy)piperidine-1-carboxylate Benzyl (2R,3S)-2-(3-((2-amino-2-bromophenyl)amino)-2-hydroxypropyl)-3-((tert-butyldimethylsilyl)oxy)piperidine-1-carboxylate (120 mg, 0.20 mmol) obtained from Step 1-6 was dissolved in toluene (1 mL, 0.3M) to which papatoluene sulfonic acid (7 mg, 0.04 mmol) and triethylorthoformate (100 uL, 0.42 mmol) were added and then stirred at 40° C. for 12 hours. When the reaction was completed, the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=1:2) to give the title compound (64 mg, yield: 55%).

Step 1-8: Preparation of benzyl (2R,3S)-2-(3-(4-bromo-1H-benzo[d]imidazol-1-yl)-2-oxopropyl)-3-((tert-butyldimethylsilyl)oxy)piperidine-1-carboxylate Benzyl (2R,3S)-2-(3-((4-bromo-1H-benzo[d]imidazol-1-yl)-2-hydroxypropyl)-3-((tert-butyldimethylsilyl)oxy)piperidine-1-carboxylate (64 mg, 0.11 mmol) obtained from Step 1-7 was dissolved in dichloromethane (1 mL, 0.1 M) to which Dess-Martin periodinane (54 mg, 0.13 mmol) was added and then stirred at room temperature for 3 hours. When the reaction was completed, the resulting mixture was diluted with ethyl acetate and washed with saturated sodium chloride solution. The organic layer was collected, dried over magnesium sulfate, filtered and concentrated under reduced pressure, and then purified by column chromatography (dichloromethane:methanol=15:1) to give the title compound (49 mg, yield: 77%).

Step 1-9: Preparation of benzyl (2R,3S)-3-((tert-butyldimethylsilyl)oxy)-2-(2-oxo-3-(4-phenyl-1H-benzo[d]imidazol-1-yl)propyl)piperidine-1-carboxylate Benzyl (2R,3S)-2-(3-(4-bromo-1H-benzo[d]imidazol-1-yl)-2-oxopropyl)-3-((tert-butyldimethylsilyl)oxy)piperidine-1-carboxylate (49 mg, 0.08 mmol) obtained from Step 1-8 was dissolved in N,N-dimethylformamide (3 mL, 0.03 M) to which phenylboronic acid (15 mg, 0.12 mmol), tetrakis (triphenylphosphine)palladium(0) (19 mg, 0.02 mmol) and 2M aqueous sodium carbonate solution (300 uL, 0.3 M) were added and stirred at 120° C. for 45 minutes using a microwave apparatus. When the reaction was completed, the resulting mixture was diluted with ethyl acetate and washed with saturated sodium chloride solution. The organic layer was collected, dried over magnesium sulfate, filtered and concentrated under reduced pressure, and then purified by column chromatography (ethylacetate 100%) to give the title compound (42 mg, yield: 85%).

Step 1-10: Preparation of 1-((2R,3S)-3-hydroxypiperidin-2-yl)-3-(4-phenyl-1H-benzo[d]imidazol-1-yl)propan-2-one Benzyl (2R,3S)-3-((tert-butyldimethylsilyl)oxy)-2-(2-oxo-3-(4-phenyl-1H-benzo[d]imidazol-1-yl)propyl)piperidine-1-carboxylate (42 mg, 0.07 mmol) obtained from Step 1-9 was dissolved in 6N hydrogen chloride solution (2 mL 0.04 M) and then stirred under reflux for 1 hour. When the reaction was completed, the reaction solution was cooled to 0° C., neutralized (pH 7) with potassium carbonate, and extracted with a mixed solution of chloroform and a small amount of acetone. The organic layer was collected, dried over magnesium sulfate, filtered and concentrated under reduced pressure, and then recrystallized with diethylether to give the title compound (17 mg, yield: 70%).

$^1$H-NMR (500 MHz, DMSO-$d_6$): R 8.01 (s, 1H), 7.67 (d, 1H), 7.43 (m, 3H), 7.23 (m, 3H), 6.99 (d, 1H), 4.82 (dd, 2H), 4.64 (m, 1H), 2.77 (m, 1H), 2.68 (d, 1H), 2.25 (m, 1H), 2.22 (m, 2H), 1.78 (m, 1H), 1.68 (m, 1H), 1.48 (m, 1H), 1.25 (m, 1H), 1.12 (m, 1H)

EXAMPLE 2

Preparation of 1-(4-(3-fluorophenyl)-1H-imidazo[4,5-c]pyridin-1-yl)-3-((2R,3S)-3-hydroxypiperidin-2-yl)propan-2-one

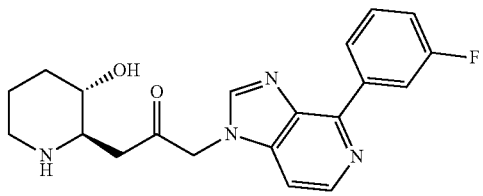 [SMILES: O=C(C[C@H]1NCCC[C@@H]1O)Cn1cnc2c(-c3cccc(F)c3)nccc21]

Step 2-1: Preparation of benzyl (2R,3S)-3-(3-(4-bromo-1H-imidazo[4,5-c]pyridin-1-yl)-2-oxopropyl)-3-((tert-butyldimethylsilyl)oxy)piperidine-1-carboxylate 4-Bromo-1H-imidazo[4,5-c]pyridine (204 mg, 1.03 mmol) was dissolved in N,N-dimethylformamide (4 mL, 0.25 M) to which potassium carbonate (285 mg, 2.06 mmol) was added and then stirred at room temperature at 10 minutes. Then, benzyl (2R,3S)-2-(3-bromo-2-oxopropyl)-3-((tert-butyldimethylsilyl)oxy)piperidine-1-carboxylate (500 mg, 1.03 mmol) was added thereto and stirred at room temperature for 3 hours. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (dichloromethane:methanol=10:1) to give the title compound (554 mg, yield: 89%).

Step 2-2: Preparation of benzyl (2R,3S)-3-((tert-butyldimethylsilyl)oxy)-2-(3-(4-(3-fluorophenyl)-1H-imidazo[4,5-c]pyridin-1-yl)-2-oxopropyl)piperidine-1-carboxylate Benzyl (2R,3S)-3-(3-(4-bromo-1H-imidazo[4,5-c]pyridin-1-yl)-2-oxopropyl)-3-((tert-butyldimethylsilyl)oxy)piperidine-1-carboxylate (91 mg, 0.15 mmol) obtained from Step 2-1 was dissolved in N,N-dimethylformamide (3 mL, 0.05 M) to which (3-fluorophenyl)boronic acid (31 mg, 0.23 mmol), tetrakis(triphenylphosphine)palladium (35 mg, 0.03 mmol) and 2M sodium carbonate (0.3 mL, 0.61 mmol) were sequentially added and then stirred at room temperature for 5 minutes. Then, the mixture was reacted at 130° C. for 45 minutes using a microwave. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=1:2) to give the title compound (61 mg, yield: 65%).

Step 2-3: Preparation of 1-(4-(3-fluorophenyl)-1H-imidazo[4,5-c]pyridin-1-yl)-3-((2R,3S)-3-hydroxypiperidin-2-yl)propane-2-one Benzyl (2R,3S)-3-((tert-butyldimethylsilyl)oxy)-2-(3-(4-(3-fluorophenyl)-1H-imidazo[4,5-c]pyridin-1-yl)-2-oxopropyl)piperidine-1-carboxylate (61 mg, 0.10 mmol) obtained from Step 2-2 was dissolved in 6N hydrogen chloride solution (3 mL 0.03 M) and then stirred under reflux for 1 hour. When the reaction was completed, the reaction solution was cooled to 0° C., neutralized (pH 7) with potassium carbonate and then extracted with a mixed solution of chloroform and a small amount of acetone. The organic layer was collected, dried over magnesium sulfate, filtered and concentrated under reduced pressure, and then recrystallized with diethylether to give the title compound (19 mg, yield: 52%).

$^1$H-NMR (500 MHz, DMSO-$d_6$): δ 8.64 (d, 1H), 8.59 (d, 1H), 8.44 (d, 1H), 8.33 (s, 1H), 7.56-7.61 (m, 2H), 7.29-7.32 (m, 1H), 5.46 (m, 2H), 5.01 (s, 1H), 3.12 (bs, 1H), 3.00 (dd, 1H), 2.89 (d, 1H), 2.81 (s, 1H), 1.92 (m, 1H), 1.63 (d, 1H), 1.23-1.46 (m, 3H).

EXAMPLE 3

Preparation of 1-(4-(3-chlorophenyl)-1H-imidazo[4,5-c]pyridin-1-yl)-3-((2R,3S)-3-hydroxypiperidin-2-yl)propan-2-one

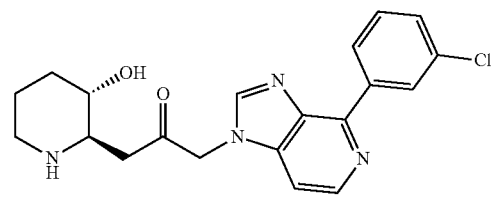 [SMILES: O=C(C[C@H]1NCCC[C@@H]1O)Cn1cnc2c(-c3cccc(Cl)c3)nccc21]

The title compound (18 mg, yield: 33%) was obtained in the same manner as in Example 2, with the exception that (3-chlorophenyl)boronic acid was used instead of (3-fluorophenyl)boronic acid.

$^1$H-NMR (500 MHz, DMSO-$d_6$): δ 8.86 (s, 1H), 8.74 (d, 1H), 8.44 (d, 1H), 8.34 (s, 1H), 7.52-7.60 (m, 3H), 5.42 (m, 2H), 4.92 (s, 1H), 3.07 (m, 1H), 2.98 (dd, 1H), 2.86 (d, 1H), 2.73 (m, 1H), 1.61 (d, 1H), 1.24-1.43 (m, 3H).

EXAMPLE 4

Preparation of 1-((2R,3S)-3-hydroxypiperidin-2-yl)-3-(4-(3-(trifluoromethyl)phenyl)-1H-imidazo[4,5-c]pyridin-1-yl)propan-2-one

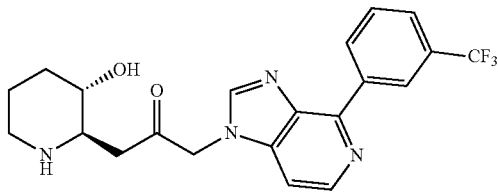 [SMILES: O=C(C[C@H]1NCCC[C@@H]1O)Cn1cnc2c(-c3cccc(C(F)(F)F)c3)nccc21]

The title compound (22 mg, yield: 39%) was obtained in the same manner as in Example 2, with the exception that (3-trifluoromethyl)boronic acid was used instead of (3-fluorophenyl)boronic acid.

$^1$H-NMR (500 MHz, DMSO-$d_6$): δ 9.16 (s, 1H), 9.08 (d, 1H), 8.48 (d, 1H), 8.36 (s, 1H), 7.79-7.85 (m, 2H), 7.60 (d, 1H), 5.46 (m, 2H), 4.95 (s, 1H), 3.09 (bs, 1H), 2.99 (dd, 1H), 2.87 (d, 1H), 2.77 (s, 1H), 1.92 (m, 1H), 1.62 (d, 1H), 1.27-1.44 (m, 3H).

EXAMPLE 5

Preparation of 1-(4-(3-chloro-5-fluorophenyl)-1H-imidazo[4,5-c]pyridin-1-yl)-3-((2R,3S)-3-hydroxypiperidin-2-yl)propan-2-one

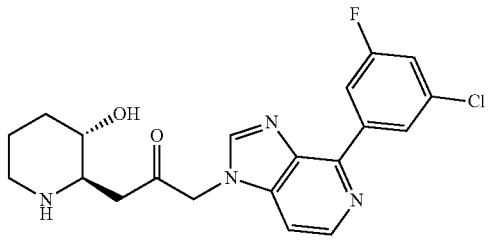 [SMILES: O=C(C[C@H]1NCCC[C@@H]1O)Cn1cnc2c(-c3cc(F)cc(Cl)c3)nccc21]

The title compound (19 mg, yield: 34%) was obtained in the same manner as in Example 2, with the exception that (3-chloro-5-fluoromethyl)boronic acid was used instead of (3-fluorophenyl)boronic acid.

$^1$H-NMR (500 MHz, DMSO-$d_6$): δ 8.78 (s, 1H), 8.59 (d, 1H), 8.45 (d, 1H), 8.38 (s, 1H), 7.62 (d, 1H), 7.55 (m, 1H), 5.46 (m, 1H), 4.92 (m, 1H), 3.09 (m, 1H), 2.98 (dd, 1H), 2.86 (d, 1H), 2.74 (m, 1H), 1.92 (m, 1H), 1.61 (d, 1H), 1.25-1.40 (m, 3H).

EXAMPLE 6

Preparation of 1-(4-(3,5-dichlorophenyl)-1H-imidazo[4,5-c]pyridin-1-yl)-3-((2R,3S)-3-hydroxypiperidin-2-yl)propan-2-one

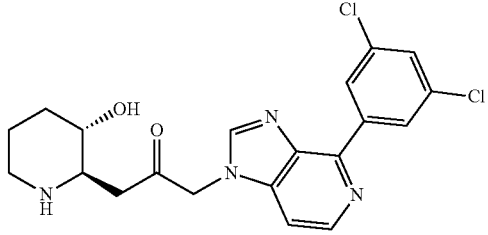 [SMILES: O=C(C[C@H]1NCCC[C@@H]1O)Cn1cnc2c(-c3cc(Cl)cc(Cl)c3)nccc21]

The title compound (20 mg, yield: 36%) was obtained in the same manner as in Example 2, with the exception that (3,5-dichlorophenyl)boronic acid was used instead of (3-fluorophenyl)boronic acid.

$^1$H-NMR (500 MHz, DMSO-$d_6$): δ 8.85 (d, 2H), 8.47 (d, 1H), 8.38 (s, 1H), 7.72 (m, 1H), 7.62 (m, 1H), 5.46 (m, 2H), 4.93 bs, 1H), 3.07 (m, 1H), 2.98 (dd, 1H), 2.86 (d, 1H), 2.75 (m, 1H), 1.92 (m, 1H), 1.61 (d, 1H), 1.25-1.41 (m, 3H).

EXAMPLE 7

Preparation of 1-((2R,3S)-3-hydroxypiperidin-2-yl)-3-(4-(pyrrolidin-1-yl)-1H-imidazo[4,5-c]pyridin-1-yl)propan-2-one

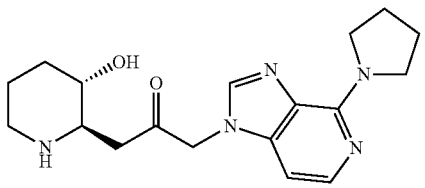 [SMILES: O=C(C[C@H]1NCCC[C@@H]1O)Cn1cnc2c(N3CCCC3)nccc21]

Step 7-1: Preparation of benzyl (2R,3S)-2-(3-(4-bromo-1H-imidazo[4,5-c]pyridin-1-yl)-2-oxopropyl)-3-((tert-butyldimethylsilyl)oxy)piperidine-1-carboxylate The title compound (554 mg, yield: 89%) was obtained from 4-bromo-1H-imidazo[4,5-c]pyridine (204 mg, 1.03 mmol), in the same manner as in Step 2-1 of Example 2.

Step 7-2: Preparation of benzyl (2R,3S)-3-((tert-butyldimethylsilyl)oxy)-2-(3-(4-(pyrrolidin-1-yl)-1H-imidazo[4,5-c]pyridin-1-yl)-2-oxopropyl)piperidine-1-carboxylate Benzyl (2R,3S)-2-(3-(4-bromo-1H-imidazo[4,5-c]pyridin-1-yl)-2-oxopropyl)-3-((tert-butyldimethylsilyl)oxy)piperidine-1-carboxylate (100 mg, 0.17 mmol) obtained from Step 7-1 was dissolved in ethanol (3 mL, 0.05 M) to which pyrrolidine (27 μL, 0.33 mmol) and triethylamine (93 μL, 0.66 mmol) were sequentially added and then stirred under reflux at 80° C. for 72 hours. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=1:2) to give the title compound (88 mg, yield: 89%).

Step 7-3: Preparation of (2R,3S)-3-hydroxypiperidin-2-yl)-3-(4-(pyrrolidin-1-yl)-1H-imidazo[4,5-c]pyridin-1-yl)propan-2-one Benzyl (2R,3S)-3-((tert-butyldimethylsilyl)oxy)-2-(3-(4-(pyrrolidin-1-yl)-1H-imidazo[4,5-c]pyridin-1-yl)-2-oxopropyl)piperidine-1-carboxylate (88 mg, 0.15 mmol) obtained from Step 7-2 was dissolved in 6N hydrochloric acid solution (3 mL, 0.05 M) and then stirred under reflux for 1 hour. When the reaction was completed, the reaction solution was cooled to 0° C., neutralized (pH 7) with potassium carbonate and then extracted with a mixed solution of chloroform and a small amount of acetone. The organic layer was collected, dried over magnesium sulfate, filtered and concentrated under reduced pressure, and then recrystallized with diethylether to give the title compound (23 mg, yield: 45%).

$^1$H-NMR (500 MHz, DMSO-$d_6$): δ 7.87 (s, 1H), 87.73 (d, 1H), 6.65 (d, 1H), 5.25 (m, 2H), 4.97 (s, 1H), 3.84 (s, 4H), 3.23 (s, 1H), 2.87-3.09 9m, 2H), 2.78 (S, 1H), 1.94 (m, 5H), 1.64 (d, 1H), 1.42 (m, 1H), 1.31 (s, 2H).

EXAMPLE 8

Preparation of 1-((2R,3S)-3-hydroxypiperidin-2-yl)-3-(5-phenyl-1H-benzo[d]imidazol-1-yl)propan-2-one

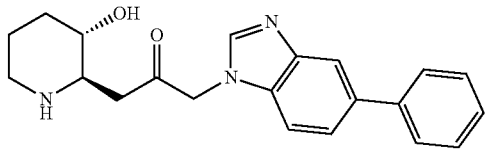 [SMILES: O=C(C[C@H]1NCCC[C@@H]1O)Cn1cnc2cc(-c3ccccc3)ccc21]

The title compound (25 mg, yield: 81%) was obtained in the same manner as in Example 1, with the exception that 4-bromo-1-fluoro-2-nitrobenzene was used instead of 1-bromo-3-fluoro-2-nitrobenzene in Step 1-5 of Example 1.

$^1$H-NMR (500 MHz, DMSO-$d_6$): δ 8.08 (s, 1H), 7.89 (s, 1H), 7.69 (d, 2H), 7.52 (d, 2H), 7.45 (m, 2H), 7.33 (m, 1H), 5.34 (dd, 2H), 4.85 (d, 1H), 3.16 (m, 1H), 2.93 (m, 1H), 2.80 (m, 1H), 2.65 (m, 1H), 2.38 (m, 2H), 1.89 (m, 1H), 1.56 (m, 1H), 1.35 (m, 1H), 1.22 (m, 1H)

EXAMPLE 9

Preparation of 1-(5-(2-fluorophenyl)-1H-imidazo[4,5-b]pyridin-1-yl)-3-((2R,3S)-3-hydroxypiperidin-2-yl)propan-2-one

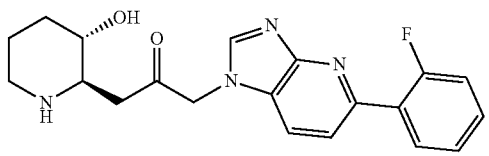 [SMILES: O=C(C[C@H]1NCCC[C@@H]1O)Cn1cnc2nc(-c3ccccc3F)ccc21]

Step 9-1: Preparation of benzyl (2R,3S)-2-(3-(5-bromo-1H-imidazo[4,5-b]pyridin-1-yl)-2-oxopropyl)-3-((tert-butyldimethylsilyl)oxy)piperidine-1-carboxylate 5-Bromo-1H-imidazo[4,5-b]pyridine (245 mg, 1.24 mmol) was dissolved in N,N-dimethylformamide (5 mL, 0.25 M) to which potassium carbonate (324 mg, 2.48 mmol) was added and then stirred at room temperature for 10 minutes. Then, benzyl (2R,3S)-2-(3-bromo-2-oxopropyl)-3-((tert-butyldimethylsilyl)oxy)piperidine-1-carboxylate (600 mg, 1.24 mmol) was added thereto and stirred at room temperature for 3 hours. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (dichloromethane:methanol=10:1) to give the title compound (300 mg, yield: 40%).

Step 9-2: Preparation of benzyl (2R,3S)-3-((tert-butyldimethylsilyl)oxy)-2-(3-(5-(2-fluorophenyl)-1H-imidazo[4,5-b]pyridin-1-yl)-2-oxopropyl)piperidine-1-carboxylate Benzyl (2R,3S)-2-(3-(5-bromo-1H-imidazo[4,5-b]pyridin-1-yl)-2-oxopropyl)-3-((tert-butyldimethylsilyl)oxy)piperidine-1-carboxylate (50 mg, 0.08 mmol) obtained from Step 9-1 was dissolved in N,N-dimethylformamide (2 mL, 0.05 M) to which (2-fluorophenyl)boronic acid (18 mg, 0.13 mmol), tetrakis(triphenylphosphine)palladium (20 mg, 0.02 mmol) and 2M sodium carbonate (0.2 mL, 0.33 mmol) were sequentially added and then stirred at room temperature for 5 minutes. Then, the mixture was reacted at 150° C. for 30 minutes using a microwave. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=1:2) to give the title compound (40 mg, yield: 78%).

Step 9-3: Preparation of 1-(5-(2-fluorophenyl)-1H-imidazo[4,5-b]pyridin-1-yl)-3-((2R,3S)-3-hydroxypiperidin-2-yl)propane-2-one Benzyl (2R,3S)-3-((tert-butyldimethylsilyl)oxy)-2-(3-(5-(2-fluorophenyl)-1H-imidazo[4,5-b]pyridin-1-yl)-2-oxopropyl)piperidine-1-carboxylate (40 mg, 0.06 mmol) obtained from Step 9-2 was dissolved in 6N hydrogen chloride solution (3 mL, 0.02 M) and then stirred under reflux for 1 hour. When the reaction was completed, the reaction solution was cooled to 0° C., neutralized (pH 7) with potassium carbonate and then extracted with a mixed solution of chloroform and a small amount of acetone. The organic layer was collected, dried over magnesium sulfate, filtered and concentrated under reduced pressure, and then recrystallized with diethylether to give the title compound (17 mg, yield: 70%).

$^1$H-NMR (500 MHz, DMSO-$d_6$): δ 8.36 (s, 1H), 8.00 (d, 1H), 7.94 (t, 1H), 7.66 (d, 1H), 7.46 (m, 1H), 7.53 (m, 2H), 5.40 (dd, 2H), 4.86 (d, 1H), 3.03 (m, 1H), 2.95 (dd, 1H), 2.83 (d, 1H), 2.70 (m, 1H), 2.42 (m, 1H), 2.39 (m, 1H), 1.92 (d, 1H), 1.59 (d, 1H), 1.35 (m 1H), 1.23 (m, 1H).

EXAMPLE 10

Preparation of 1-(5-(3-fluorophenyl)-1H-imidazo[4,5-b]pyridin-1-yl)-3-((2R,3S)-3-hydroxypiperidin-2-yl)propan-2-one

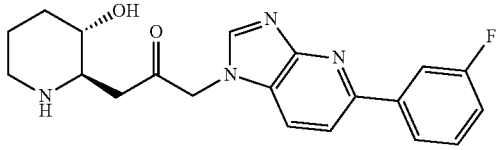 [SMILES: O=C(C[C@H]1NCCC[C@@H]1O)Cn1cnc2nc(-c3cccc(F)c3)ccc21]

The title compound (18 mg, yield: 72%) was obtained in the same manner as in Example 9, with the exception that (3-fluorophenyl)boronic acid was used instead of (2-fluorophenyl)boronic acid.

¹H-NMR (500 MHz, DMSO-d₆): δ 8.34 (s, 1H), 7.99 (t, 2H), 7.93 (m, 2H), 7.54 (dd, 1H), 7.23 (dt, 1H), 5.40 (dd, 2H), 4.85 (d, 1H), 3.00 (m, 1H), 2.95 (dd, 1H), 2.83 (d, 1H), 2.69 (m, 1H), 2.45 (m, 1H), 2.38 (t, 1H), 1.92 (d, 1H), 1.59 (d, 1H), 1.35 (m, 1H), 1.25 (m, 1H).

EXAMPLE 11

Preparation of 1-(5-(4-fluorophenyl)-1H-imidazo[4,5-b]pyridin-1-yl)-3-((2R,3S)-3-hydroxypiperidin-2-yl)propan-2-one

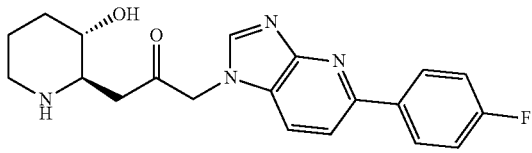 [SMILES: O=C(C[C@H]1NCCC[C@@H]1O)Cn1cnc2nc(-c3ccc(F)cc3)ccc21]

The title compound (17 mg, yield: 70%) was obtained in the same manner as in Example 9, with the exception that (4-fluorophenyl)boronic acid was used instead of (2-fluorophenyl)boronic acid.

¹H-NMR (500 MHz, DMSO-d₆): δ 8.32 (s, 1H), 8.17 (m, 2H), 7.89 (dd, 1H), 7.86 (dd, 1H), 7.33 (m, 2H), 5.39 (dd, 2H), 4.84 (d, 1H), 3.02 (m, 1H), 2.95 (dd, 1H), 2.83 (d, 1H), 2.69 (m, 1H), 2.43 (m, 1H), 2.38 (m, 1H), 1.92 (d, 1H), 1.59 (d, 1H), 1.35 (m, 1H), 1.25 (m, 1H).

EXAMPLE 12

Preparation of 1-(5-(3-chlorophenyl)-1H-imidazo[4,5-b]pyridin-1-yl)-3-((2R,3S)-3-hydroxypiperidin-2-yl)propan-2-one

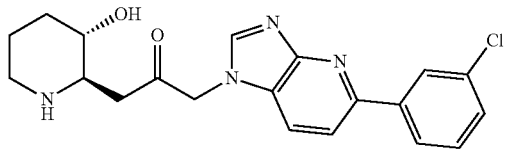 [SMILES: O=C(C[C@H]1NCCC[C@@H]1O)Cn1cnc2nc(-c3cccc(Cl)c3)ccc21]

The title compound (19 mg, yield: 80%) was obtained in the same manner as in Example 9, with the exception that (3-chlorophenyl)boronic acid was used instead of (2-chlorophenyl)boronic acid.

¹H-NMR (500 MHz, DMSO-d₆): δ 8.35 (s, 1H), 8.18 (s, 1H), 8.10 (d, 1H), 8.01 (d, 1H), 7.94 (d, 1H), 7.52 (t, 1H), 7.47 (d, 1H), 5.40 (dd, 2H), 4.85 (d, 1H), 3.05 (m, 1H), 2.94 (dd, 1H), 2.83 (d, 1H), 2.69 (m, 1H), 2.43 (m, 1H), 2.38 (m, 1H), 1.92 (d, 1H), 1.59 (d, 1H), 1.35 (m, 1H), 1.25 (m, 1H).

EXAMPLE 13

Preparation of 1-((2R,3S)-3-hydroxypiperidin-2-yl)-3-(5-(3-(trifluoromethyl)phenyl)-1H-imidazo[4,5-b]pyridin-1-yl)propan-2-one

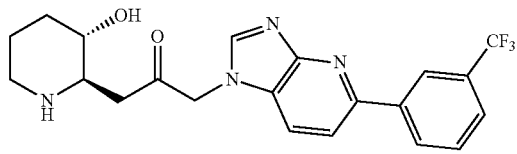 [SMILES: O=C(C[C@H]1NCCC[C@@H]1O)Cn1cnc2nc(-c3cccc(C(F)(F)F)c3)ccc21]

The title compound (20 mg, yield: 75%) was obtained in the same manner as in Example 9, with the exception that 3-(trifluoromethyl)phenyl)boronic acid was used instead of (2-fluorophenyl)boronic acid.

¹H-NMR (500 MHz, DMSO-d₆): δ 8.47 (s, 1H), 8.43 (m, 1H), 8.37 (d, 1H), 8.04 (m, 2H), 7.74 (m, 2H), 5.42 (dd, 2H), 4.84 (d, 1H), 3.03 (m, 1H), 2.96 (dd, 1H), 2.83 (d, 1H), 2.68 (m, 1H), 2.44 (m, 1H), 2.38 (m, 1H), 1.92 (d, 1H), 1.59 (d, 1H), 1.35 (m, 1H), 1.25 (m, 1H).

EXAMPLE 14

Preparation of 1-(6-(3-chlorophenyl)-3H-imidazo[4,5-b]pyridin-3-yl)-3-((2R,3S)-3-hydroxypiperidin-2-yl)propan-2-one

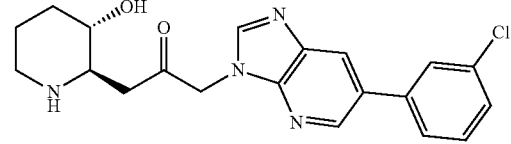 [SMILES: O=C(C[C@H]1NCCC[C@@H]1O)Cn1cnc2cc(-c3cccc(Cl)c3)cnc21]

Step 14-1: Preparation of benzyl (2R,3S)-2-(3-(6-bromo-3H-imidazo[4,5-b]pyridin-3-yl)-2-oxopropyl)-3-((tert-butyldimethylsilyl)oxy)piperidine-1-carboxylate 6-Bromo-3H-imidazo[4,5-b]pyridine (204 mg, 1.03 mmol) was dissolved in N,N-dimethylformamide (3 mL, 0.34 M) to which potassium carbonate (285 mg, 2.06 mmol) was added and then stirred at room temperature for 10 minutes. Then, benzyl (2R,3S)-2-(3-bromo-2-oxopropyl)-3-((tert-butyldimethylsilyl)oxy)piperidine-1-carboxylate (500 mg, 1.03 mmol) was added thereto at room temperature for 3 hours. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (dichloromethane:methanol=10:1) to give the title compound (266 mg, yield: 43%).

Step 14-2: Preparation of benzyl (2R,3S)-3-((tert-butyldimethylsilyl)oxy)-2-(3-(6-(3-chlorophenyl)-3H-imidazo[4,5-b]pyridin-3-yl)-2-oxopropyl)piperidine-1-carboxylate Benzyl (2R,3S)-2-(3-(6-bromo-3H-imidazo[4,5-b]pyridin-3-yl)-2-oxopropyl)-3-((tert-butyldimethylsilyl)oxy)piperidine-1-carboxylate (75 mg, 0.13 mmol) obtained from Step 14-1 was dissolved in N,N-dimethylformamide (2 mL, 0.07 M) to which (3-chlorophenyl)boric acid (29 mg, 0.19 mmol), tetrakis(triphenylphosphine)palladium (30 mg, 0.03 mmol) and 2M sodium carbonate (0.25 mL, 0.5 mmol) were sequentially added and then stirred at room temperature for 5 minutes. Then, the mixture was reacted at 150° C. for 30 minutes using a microwave. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=1:2) to give the title compound (62 mg, yield: 78%).

Step 14-3: 1-(6-(3-chlorophenyl)-3H-imidazo[4,5-b]pyridin-3-yl)-3-((2R,3S)-3-hydroxypiperidin-2-yl)propane-2-one Benzyl (2R,3S)-3-((tert-butyldimethylsilyl)oxy)-2-(3-(6-(3-chlorophenyl)-3H-imidazo[4,5-b]pyridin-3-yl)-2-oxopropyl)piperidine-1-carboxylate (62 mg, 0.1 mmol) obtained from Step 14-2 was dissolved in 6N hydrogen chloride solution (3 mL, 0.03 M) and then stirred under reflux for 1 hour. When the reaction was completed, the reaction solution was cooled to 0° C., neutralized (pH 7) with potassium carbonate and then extracted with a mixed solution of chloroform and a small amount of acetone. The organic layer was collected, dried over magnesium sulfate, filtered and concentrated under reduced pressure, and then recrystallized with diethylether to give the title compound (28 mg, yield: 75%).

$^1$H-NMR (500 MHz, DMSO-$d_6$): δ 8.65 (d, 1H), 8.41 (d, 1H), 8.35 (s, 1H), 7.84 (s, 1H), 7.74 (d, 1H), 7.48 (t, 1H), 7.44 (d, 1H), 5.36 (dd, 2H), 4.79 (d, 1H), 2.99 (m, 2H), 2.81 (d, 1H), 2.67 (m, 1H), 2.47 (m, 1H), 2.37 (m, 1H), 1.90 (m, 1H), 1.58 (d, 1H), 1.35 (m, 1H), 1.24 (m, 1H).

EXAMPLE 15

Preparation of 1-((2R,3S)-3-hydroxypiperidin-2-yl)-3-(6-(3-(trifluoromethyl)phenyl)-3H-imidazo[4,5-b]pyridin-3-yl)propan-2-one

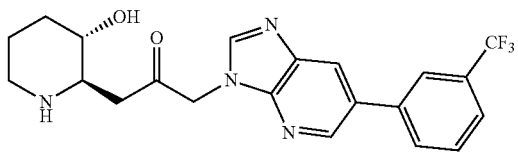 [SMILES: O=C(C[C@H]1NCCC[C@@H]1O)Cn1cnc2cc(-c3cccc(C(F)(F)F)c3)cnc21]

The title compound (33 mg, yield: 76%) was obtained in the same manner as in Example 14, with the exception that (3-(trifluoromethyl)phenyl)boronic acid was used instead of (3-chlorophenyl)boronic acid.

$^1$H-NMR (500 MHz, DMSO-$d_6$): δ 8.70 (d, 1H), 8.48 (d, 1H), 8.38 (s, 1H), 8.09 (m, 2H), 7.75 (m, 1H), 5.37 (dd, 2H), 4.80 (d, 1H), 3.00 (m, 2H), 2.82 (d, 1H), 2.68 (m, 1H), 2.51 (m, 1H), 2.38 (m, 1H), 1.90 (m, 1H), 1.59 (d, 1H), 1.35 (m, 1H), 1.26 (m, 1H).

EXAMPLE 16

Preparation of 1-(5-(3-fluorophenyl)-4-methyl-1H-benzo[d]imidazol-1-yl)-3-((2R,3S)-3-hydroxypiperidin-2-yl)propan-2-one

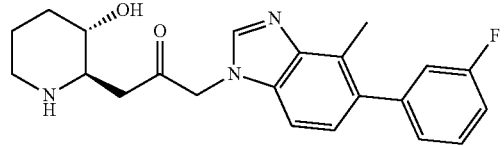 [SMILES: Cc1c(-c2cccc(F)c2)ccc2c1ncn2CC(=O)C[C@H]1NCCC[C@@H]1O]

Step 16-1: Preparation of benzyl (2R,3S)-2-(3-(5-bromo-4-methyl-1H-benzo[d]imidazol-1-yl)-2-oxopropyl)-3-((tert-butyldimethylsilyl)oxy)piperidine-1-carboxylate 5-Bromo-4-methyl-1H-benzo[d]imidazole (86.53 mg, 0.41 mmol) was dissolved in N,N-dimethylformamide (2 mL, 0.20 M) to which potassium carbonate (114.09 mg, 0.83 mmol) was added and then stirred at room temperature for 10 minutes. Then, benzyl (2R,3S)-2-(3-bromo-2-oxopropyl)-3-((tert-butyldimethylsilyl)oxy)piperidine-1-carboxylate (200 mg, 0.41 mmol) was added thereto and stirred at room temperature for 3 hours. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=5:1) to give the title compound (217 mg, yield: 86%).

Step 16-2: Preparation of benzyl (2R,3S)-3-((tert-butyldimethylsilyl)oxy)-2-(3-(5-(3-fluorophenyl)-4-methyl-1H-benzo[d]imidazol-1-yl)-2-oxopropyl)piperidine-1-carboxlate Benzyl (2R,3S)-2-(3-(5-bromo-4-methyl-1H-benzo[d]imidazol-1-yl)-2-oxopropyl)-3-((tert-butyldimethylsilyl)oxy)piperidine-1-carboxylate (50 mg, 0.08 mmol) obtained from Step 16-1 was dissolved in N,N-dimethylformamide (1.5 mL, 0.05 M) to which (3-fluorophenyl)boronic acid (16.79 mg, 0.12 mmol), tetrakis(triphenylphosphine)palladium (23.11 mg, 0.02 mmol), and 2M sodium carbonate (0.3 mL, 0.27 mmol) were sequentially added and then stirred at room temperature for 5 minutes. Then, the mixture was reacted at 130° C. for 45 minutes using a microwave. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=1:3) to give the title compound (36.3 mg, yield: 72%).

Step 16-3: Preparation of 1-(5-(3-fluorophenyl)-4-methyl-1H-benzo[d]imidazol-1-yl)-3-((2R,3S)-3-hydroxypiperidin-2-yl)propane-2-one Benzyl (2R,3S)-3-((tert-butyldimethylsilyl)oxy)-2-(3-(5-(3-fluorophenyl)-4-methyl-1H-benzo[d]imidazol-1-yl)-2-oxopropyl)piperidine-1-carboxlate (36.3 mg, 0.06 mmol)

obtained from Step 16-2 was dissolved in 6N hydrogen chloride solution (2 mL, 0.03 M) and then stirred under reflux for 1 hour. When the reaction was completed, the reaction solution was cooled to 0° C., neutralized (pH 7) with potassium carbonate and then extracted with a mixed solution of chloroform and a small amount of acetone. The organic layer was collected, dried over magnesium sulfate, filtered and concentrated under reduced pressure, and then recrystallized with diethylether to give the title compound (11 mg, yield: 48%).

$^1$H-NMR (500 MHz, DMSO-$d_6$): δ 8.08 (d, 1H), 7.50 (d, 1H), 7.35 (d, 1H), 7.23-7.12 (m, 3H), 7.10 (s, 1H), 5.38-5.5.30 (m, 2H), 4.82 (d, 1H), 3.33 (s, 1H), 2.96 (d, 1H), 2.84 (d, 2H), 2.81 (s, 2H), 2.51 (s, 3H), 2.06 (s, 1H), 1.90 (d, 1H), 1.58 (d, 1H), 1.38-1.26 (m, 1H).

EXAMPLE 17

Preparation of 1-(5-(3-chlorophenyl)-4-methyl-1H-benzo[d]imidazol-1-yl)-3-((2R,3S)-3-hydroxypiperidin-2-yl)propan-2-one

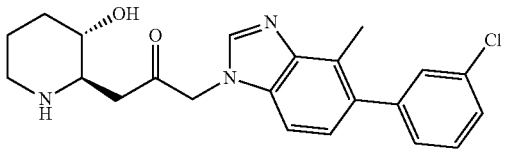 [SMILES: Cc1c(-c2cccc(Cl)c2)ccc2c1ncn2CC(=O)C[C@H]1NCCC[C@@H]1O]

The title compound (11 mg, yield: 55%) was obtained in the same manner as in Example 16, with the exception that (3-chlorophenyl)boronic acid was used instead of (3-fluorophenyl)boronic acid.

$^1$H-NMR (500 MHz, DMSO-$d_6$): δ 8.08 (s, 1H), 7.50-7.43 (m, 3H), 7.37-7.34 (m, 2H) 7.10 (s, 1H) 5.39-5.30 (m, 2H), 4.81 (d, 1H), 3.01 (s, 1H), 2.96-2.92 (dd, 1H), 2.81 (d, 2H), 2.65 (d, 2H), 2.51 (s, 3H), 2.05 (s, 1H), 1.90 (d, 1H), 1.57 (d, 1H), 1.38-1.26 (m, 1H).

EXAMPLE 18

Preparation of 1-(5-(2-chlorophenyl)-4-methyl-1H-benzo[d]imidazol-1-yl)-3-((2R,3S)-3-hydroxypiperidin-2-yl)propan-2-one

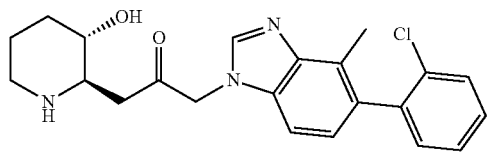

The title compound (4.0 mg, yield: 14.8%) was obtained in the same manner as in Example 16, with the exception that (2-chlorophenyl)boronic acid was used instead of (3-fluorophenyl)boronic acid.

$^1$H-NMR (500 MHz, MeOD): δ 8.11 (s, 1H), 7.65-7.62 (m, 1H), 7.57-7.50 (m, 1H) 7.37-7.28 (m, 3H) 7.04 (d, 1H), 3.49-3.48 (m, 1H), 3.11 (d, 1H), 3.00-2.98 (m, 1H), 2.62 (t, 1H), 2.57-2.55 (m, 2H), 2.35 (s, 3H), 2.04 (d, 1H), 1.77 (d, 1H), 1.58-1.56 (m, 1H), 1.42-1.40 (m, 1H).

EXAMPLE 19

Preparation of 1-(5-(4-chlorophenyl)-4-methyl-1H-benzo[d]imidazol-1-yl)-3-((2R,3S)-3-hydroxypiperidin-2-yl)propan-2-one

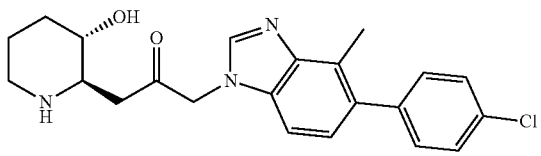 [SMILES: Cc1c(-c2ccc(Cl)cc2)ccc2c1ncn2CC(=O)C[C@H]1NCCC[C@@H]1O]

The title compound (4.0 mg, yield: 15.4%) was obtained in the same manner as in Example 16, with the exception that (4-chlorophenyl)boronic acid was used instead of (3-fluorophenyl)boronic acid.

$^1$H-NMR (500 MHz, MeOD): δ 8.10 (s, 1H), 7.42 (d, 2H), 7.34-7.32 (m, 3H), 7.15 (d, 1H), 3.48-3.44 (m, 1H), 3.16-3.07 (m, 1H), 2.93 (s, 1H), 2.86 (d, 1H), 2.53 (t, 2H), 2.51 (s, 3H), 2.03 (d, 1H), 1.73 (d, 1H), 1.55-1.53 (m, 1H), 1.39-37 (m, 1H).

EXAMPLE 20

Preparation of 3-(1-(3-((2R,3S)-3-hydroxypiperidin-2-yl)-2-oxopropyl)-4-methyl-1H-benzo[d]imidazol-5-yl)benzonitrile

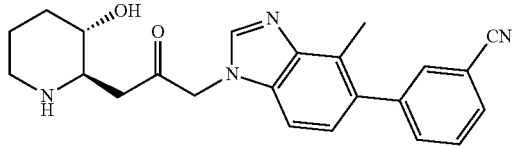 [SMILES: Cc1c(-c2cccc(C#N)c2)ccc2c1ncn2CC(=O)C[C@H]1NCCC[C@@H]1O]

The title compound (3.5 mg, yield: 20.8%) was obtained in the same manner as in Example 16, with the exception that (3-cyanophenyl)boronic acid was used instead of (3-fluorophenyl)boronic acid.

$^1$H-NMR (500 MHz, MeOD): δ 8.12 (s, 1H), 7.72-7.56 (m, 4H), 7.36 (d, 1H), 7.36 (d, 1H), 3.49-3.45 (m, 1H), 3.16-3.08 (m, 1H), 2.94 (s, 1H), 2.88 (d, 1H), 2.60-2.55 (m, 2H), 2.52 (s, 3H), 2.04 (d, 1H), 1.73 (d, 1H), 1.56-1.53 (m, 1H), 1.40-38 (m, 1H).

EXAMPLE 21

Preparation of 1-((2R,3S)-3-hydroxypiperidin-2-yl)-3-(4-methyl-5-(3-(trifluoromethyl)phenyl)-1H-benzo[d]imidazol-1-yl)propan-2-one

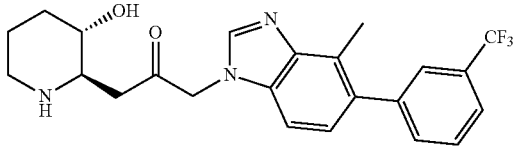 [SMILES: Cc1c(-c2cccc(C(F)(F)F)c2)ccc2c1ncn2CC(=O)C[C@H]1NCCC[C@@H]1O]

The title compound (8.6 mg, yield: 38.2%) was obtained in the same manner as in Example 16, with the exception that (3-(trifluoromethyl)phenyl)boronic acid was used instead of (3-fluorophenyl)boronic acid.

¹H-NMR (500 MHz, MeOD): δ 8.12 (s, 1H), 7.65-7.61 (m, 4H), 7.36 (d, 1H), 7.18 (d, 1H), 3.22-3.07 (m, 2H), 2.92 (d, 2H), 2.87-2.84 (m, 2H), 2.57-2.55 (m, 2H), 2.52 (s, 3H), 2.04 (d, 1H), 1.72 (d, 1H), 1.54-1.52 (m, 1H), 1.41-1.36 (m, 1H).

EXAMPLE 22

Preparation of 1-((2R,3S)-3-hydroxypiperidin-2-yl)-3-(5-(3-methoxyphenyl)-4-methyl-1H-benzo[d]imidazol-1-yl)propan-2-one

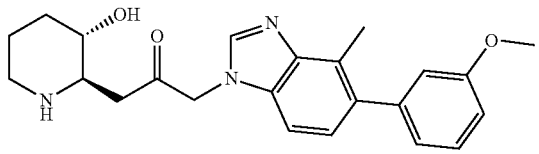 [SMILES: COc1cccc(-c2ccc3c(ncn3CC(=O)C[C@H]3NCCC[C@@H]3O)c2C)c1]

The title compound (5.0 mg, yield: 33.5%) was obtained in the same manner as in Example 16, with the exception that (3-methoxyphenyl)boronic acid was used instead of (3-fluorophenyl)boronic acid.

¹H-NMR (500 MHz, MeOD): δ 8.09 (s, 1H), 7.35-7.29 (m, 2H), 7.16 (d, 1H), 6.91-6.87 (m, 3H), 3.82 (s, 3H), 3.51-3.44 (m, 1H), 3.23-3.07 (m, 1H), 2.93 (d, 1H), 2.88-2.87 (m, 1H), 2.59-2.54 (m, 2H), 2.51 (s, 3H), 2.03 (d, 1H), 1.73 (d, 1H), 1.55-1.52 (m, 1H), 1.41-1.37 (m, 1H).

EXAMPLE 23

Preparation of 1-((2R,3S)-3-hydroxypiperidin-2-yl)-3-(4-methyl-5-(thiazol-4-yl)-1H-benzo[d]imidazol-1-yl)propan-2-one

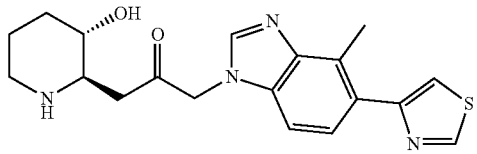 [SMILES: Cc1c(-c2cscn2)ccc2c1ncn2CC(=O)C[C@H]1NCCC[C@@H]1O]

The title compound (10 mg, yield: 50%) was obtained in the same manner as in Example 16, with the exception that (thiazol-4-yl)boronic acid was used instead of (3-fluorophenyl)boronic acid.

¹H-NMR (500 MHz, DMSO-d₆): δ 8.00 (s, 1H), 7.60 (m, 1H), 7.25 (d, 1H), 7.09 (t, 1H), 6.99 (d, 1H), 5.29 (m, 2H), 4.82 (d, 1H), 3.01 (m, 1H), 2.92 (dd, 1H), 2.82 (d, 1H), 2.67 (d, 2H), 2.54 (s, 3H), 2.41 (m, 2H), 1.90 (m, 1H), 1.58 (d, 1H), 1.21-1.37 (m, 2H)

EXAMPLE 24

Preparation of 1-((2R,3S)-3-hydroxypiperidin-2-yl)-3-(6-phenyl-1H-benzo[d]imidazol-1-yl)propan-2-one

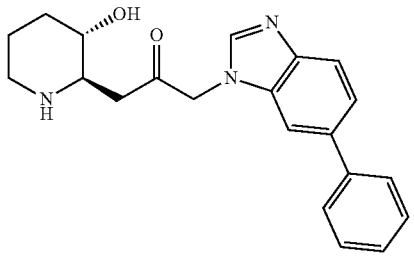 [SMILES: O=C(C[C@H]1NCCC[C@@H]1O)Cn1cnc2ccc(-c3ccccc3)cc21]

The title compound (22 mg, yield: 75%) was obtained in the same manner as in Example 1, with the exception that 4-bromo-1-fluoro-2-nitrobenzene was used instead of 4-bromo-3-fluoro-2-nitrobenzene in Step 1-5 of Example 1.

¹H-NMR (500 MHz, DMSO-d₆): δ 8.06 (s, 1H), 7.77 (d, 1H), 7.66 (m, 3H), 7.52 (m, 1H), 7.43 (m, 2H), 7.33 (m, 1H), 5.37 (d, 2H), 4.92 (m, 1H), 3.05 (m, 1H), 2.97 (m, 1H), 2.81 (m, 1H), 2.68 (m, 1H), 2.36 (m, 2H), 1.85 (m, 1H), 1.55 (m, 1H), 1.36 (m, 1H), 1.22 (m, 1H)

EXAMPLE 25

Preparation of 1-(6-(3-fluorophenyl)-1H-benzo[d]imidazol-1-yl)-3-((2R,3S)-3-hydroxypiperidin-2-yl)propan-2-one

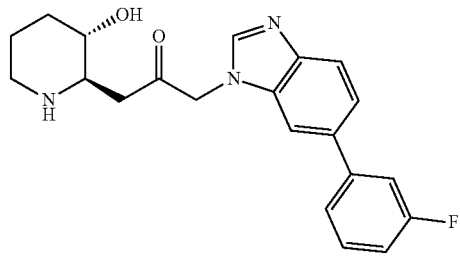 [SMILES: O=C(C[C@H]1NCCC[C@@H]1O)Cn1cnc2ccc(-c3cccc(F)c3)cc21]

The title compound (19 mg, yield: 77%) was obtained in the same manner as in Example 1, with the exception that 4-bromo-2-fluoro-1-nitrobenzene was used instead of 1-bromo-3-fluoro-2-nitrobenzene in Step 1-5 of Example 1, and (3-fluorophenyl)boronic acid was used instead of phenylboronic acid in Step 1-9 of Example 1.

¹H-NMR (500 MHz, DMSO-d₆): δ 8.10 (s, 1H), 7.86 (d, 1H), 7.71 (d, 1H), 7.55 (m, 2H), 7.51 (m, 2H), 7.17 (m, 1H), 5.38 (dd, 2H), 4.82 (m, 1H), 3.01 (m, 1H), 2.98 (dd, 1H), 2.82 (d, 1H), 2.69 (m, 1H), 2.37 (m, 1H), 2.11 (m, 1H), 1.90 (d, 1H), 1.56 (m, 1H), 1.35 (m, 1H), 1.23 (m, 1H)

EXAMPLE 26

Preparation of 1-(6-(2-chlorophenyl)-1H-benzo[d]imidazol-1-yl)-3-((2R,3S)-3-hydroxypiperidin-2-yl)propan-2-one

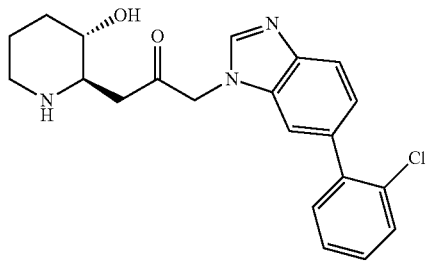 [SMILES: O=C(C[C@H]1NCCC[C@@H]1O)Cn1cnc2ccc(-c3ccccc3Cl)cc21]

The title compound (17 mg, yield: 70%) was obtained in the same manner as in Example 1, with the exception that 4-bromo-2-fluoro-1-nitrobenzene was used instead of 1-bromo-3-fluoro-2-nitrobenzene in Step 1-5 of Example 1, and (2-chlorophenyl)boronic acid was used instead of phenylboronic acid in Step 1-9 of Example 1.

$^1$H-NMR (500 MHz, DMSO-d$_6$): δ 8.10 (s, 1H), 7.71 (d, 1H), 7.58 (s, 1H), 7.57 (d, 1H), 7.40 (m, 3H), 7.26 (d, 1H), 5.36 (dd, 2H), 4.77 (d, 1H), 2.99 (m, 1H), 2.94 (dd, 1H), 2.75 (d, 1H), 2.66 (m, 1H), 2.43 (dd, 1H), 2.33 (t, 1H), 1.88 (d, 1H), 1.55 (d, 1H), 1.33 (m, 1H), 1.22 (m, 1H).

EXAMPLE 27

Preparation of 1-(6-(3-chlorophenyl)-1H-benzo[d]imidazol-1-yl)-3-((2R,3S)-3-hydroxypiperidin-2-yl)propan-2-one

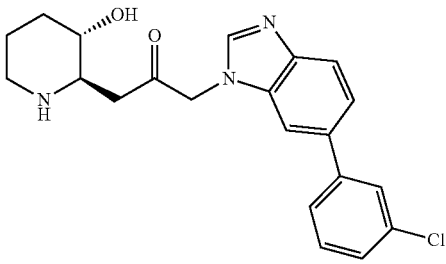 [SMILES: O=C(C[C@H]1NCCC[C@@H]1O)Cn1cnc2ccc(-c3cccc(Cl)c3)cc21]

The title compound (18 mg, yield: 72%) was obtained in the same manner as in Example 1, with the exception that 4-bromo-2-fluoro-1-nitrobenzene was used instead of 1-bromo-3-fluoro-2-nitrobenzene in Step 1-5 of Example 1, and (3-chlorophenyl)boronic acid was used instead of phenylboronic acid in Step 1-9 of Example 1.

$^1$H-NMR (500 MHz, DMSO-d$_6$): δ 8.09 (s, 1H), 7.86 (s, 1H), 7.72 (d, 2H), 7.67 (d, 1H), 7.54 (d, 1H), 7.48 (t, 1H), 7.40 (d, 1H), 5.40 (dd, 2H), 4.83 (d, 1H), 3.01 (m, 1H), 2.89 (dd, 1H), 2.84 (d, 1H), 2.70 (m, 1H), 2.45 (m, 1H), 2.36 (m, 1H), 1.90 (m, 1H), 1.59 (d, 1H), 1.37 (m, 1H), 1.24 (m, 1H).

EXAMPLE 28

Preparation of 1-(6-(4-chlorophenyl)-1H-benzo[d]imidazol-1-yl)-3-((2R,3S)-3-hydroxypiperidin-2-yl)propan-2-one

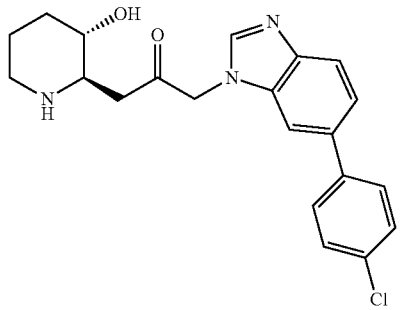 [SMILES: O=C(C[C@H]1NCCC[C@@H]1O)Cn1cnc2ccc(-c3ccc(Cl)cc3)cc21]

The title compound (17 mg, yield: 70%) was obtained in the same manner as in Example 1, with the exception that 4-bromo-2-fluoro-1-nitrobenzene was used instead of 1-bromo-3-fluoro-2-nitrobenzene in Step 1-5 of Example 1, and (4-chlorophenyl)boronic acid was used instead of phenylboronic acid in Step 1-9 of Example 1.

$^1$H-NMR (500 MHz, DMSO-d$_6$): δ 8.08 (s, 1H), 7.82 (s, 1H), 7.71 (m. 3H), 7.52 (m, 3H), 5.39 (dd, 2H), 4.82 (d, 1H), 3.01 (m, 1H), 2.95 (dd, 1H), 2.82 (d, 1H), 2.69 (m, 1H), 2.43 (m, 1H), 2.38 (m, 1H), 1.92 (d, 1H), 1.59 (d, 1H), 1.36 (m, 1H), 1.25 (m, 1H).

EXAMPLE 29

Preparation of 1-((2R,3S)-3-hydroxypiperidin-2-yl)-3-(6-(3-(trifluoromethyl)phenyl)-1H-benzo[d]imidazol-1-yl)propan-2-one

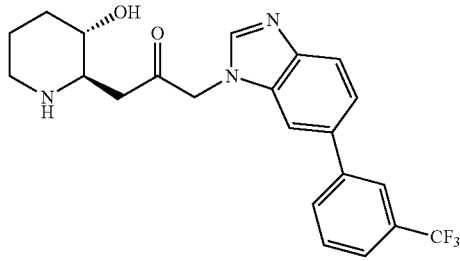 [SMILES: O=C(C[C@H]1NCCC[C@@H]1O)Cn1cnc2ccc(-c3cccc(C(F)(F)F)c3)cc21]

The title compound (18 mg, yield: 73%) was obtained in the same manner as in Example 1, with the exception that 4-bromo-2-fluoro-1-nitrobenzene was used instead of 1-bromo-3-fluoro-2-nitrobenzene in Step 1-5 of Example 1, and (3-trifluorophenyl)boronic acid was used instead of phenylboronic acid in Step 1-9 of Example 1.

$^1$H-NMR (500 MHz, DMSO-d$_6$): δ 8.11 (s, 1H), 7.99 (m, 1H), 7.96 (s, 1H), 7.75 (d, 1H), 7.70 (d, 2H), 7.58 (m, 1H), 5.39 (dd, 2H), 4.85 (d, 1H), 3.02 (m, 1H), 2.97 (dd, 1H), 2.82 (d, 1H), 2.71 (m, 1H), 2.44 (m, 1H), 2.38 (m, 1H), 1.91 (m, 1H), 1.58 (d, 1H), 1.34 (m, 1H), 1.25 (m, 1H).

EXAMPLE 30

Preparation of 1-((2R,3S)-3-hydroxypiperidin-2-yl)-3-(6-(m-tolyl)-1H-benzo[d]imidazol-1-yl)propan-2-one

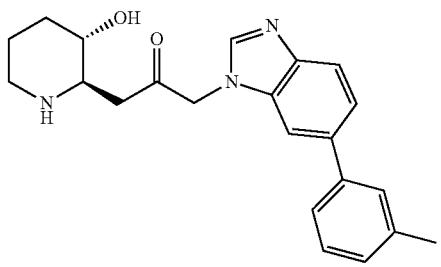 [SMILES: Cc1cccc(-c2ccc3ncn(CC(=O)C[C@H]4NCCC[C@@H]4O)c3c2)c1]

The title compound (20 mg, yield: 70%) was obtained in the same manner as in Example 1, with the exception that 4-bromo-2-fluoro-1-nitrobenzene was used instead of 1-bromo-3-fluoro-2-nitrobenzene in Step 1-5 of Example 1, and (3-methylphenyl)boronic acid was used instead of phenylboronic acid in Step 1-9 of Example 1.

$^1$H-NMR (500 MHz, DMSO-$d_6$): δ 8.06 (s, 1H), 7.78 (d, 1H), 7.69 (d, 1H), 7.49 (d, 1H), 7.45 (m, 2H), 7.34 (m, 1H), 7.15 (m, 1H), 5.41 (dd, 2H), 4.81 (m, 1H), 3.02 (m, 1H), 2.95 (dd, 1H), 2.82 (d, 1H), 2.68 (m, 1H), 2.45 (m, 2H), 2.36 (s, 3H), 1.90 (m, 1H), 1.57 (m, 1H), 1.35 (m, 1H), 1.24 (m, 1H)

EXAMPLE 31

Preparation of 1-(6-(3,5-dichlorophenyl)-1H-benzo[d]imidazol-1-yl)-3-((2R,3S)-3-hydroxypiperidin-2-yl)propan-2-one

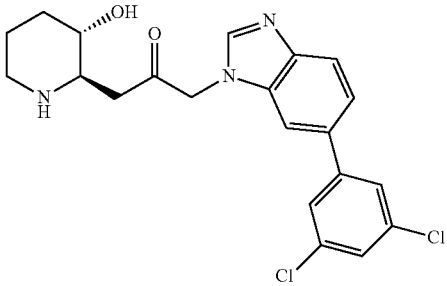 [SMILES: O=C(C[C@H]1NCCC[C@@H]1O)Cn1cnc2ccc(-c3cc(Cl)cc(Cl)c3)cc21]

The title compound (19 mg, yield: 77%) was obtained in the same manner as in Example 1, with the exception that 4-bromo-2-fluoro-1-nitrobenzene was used instead of 1-bromo-3-fluoro-2-nitrobenzene in Step 1-5 of Example 1, and (3,5-dichlorophenyl)boronic acid was used instead of phenylboronic acid in Step 1-9 of Example 1.

$^1$H-NMR (500 MHz, DMSO-$d_6$): δ 8.12 (s, 1H), 7.92 (s, 1H), 7.73 (m, 3H), 7.59 (m, 2H), 5.41 (dd, 2H), 4.89 (d, 1H), 3.05 (m, 1H), 2.99 (dd, 1H), 2.87 (d, 1H), 2.74 (m, 1H), 2.45 (m, 2H), 1.92 (d, 1H), 1.58 (d, 1H), 1.36 (m, 1H), 1.24 (m, 1H).

EXAMPLE 32

Preparation of 1-(6-(3-chloro-5-fluorophenyl)-1H-benzo[d]imidazol-1-yl)-3-((2R,3S)-3-hydroxypiperidin-2-yl)propan-2-one

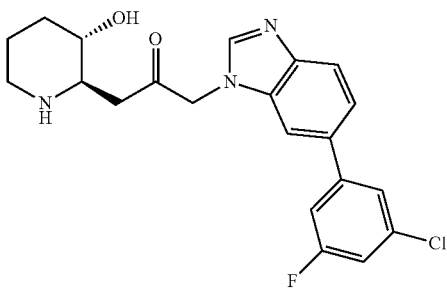 [SMILES: O=C(C[C@H]1NCCC[C@@H]1O)Cn1cnc2ccc(-c3cc(F)cc(Cl)c3)cc21]

The title compound (17 mg, yield: 70%) was obtained in the same manner as in Example 1, with the exception that 4-bromo-2-fluoro-1-nitrobenzene was used instead of 1-bromo-3-fluoro-2-nitrobenzene in Step 1-5 of Example 1, and (3-chloro-5-fluorophenyl)boronic acid was used instead of phenylboronic acid in Step 1-9 of Example 1.

$^1$H-NMR (500 MHz, DMSO-$d_6$): δ 8.21 (s, 1H), 7.92 (s, 1H), 7.73 (d, 1H), 7.63 (s, 1H), 7.59 (dd, 1H), 7.39 (dd, 1H), 5.40 (dd, 2H), 4.87 (d, 1H), 3.03 (m, 1H), 2.99 (dd, 1H), 2.85 (d, 1H), 2.72 (m, 1H), 2.44 (m, 2H), 1.92 (s, 1H), 1.60 (d, 1H), 1.35 (m, 1H), 1.26 (m, 1H).

EXAMPLE 33

Preparation of 1-(6-(3-chloro-4-fluorophenyl)-1H-benzo[d]imidazol-1-yl)-3-((2R,3S)-3-hydroxypiperidin-2-yl)propan-2-one

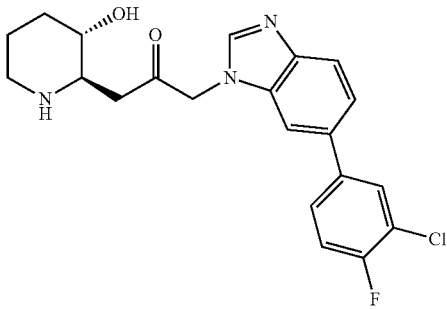 [SMILES: O=C(C[C@H]1NCCC[C@@H]1O)Cn1cnc2ccc(-c3ccc(F)c(Cl)c3)cc21]

The title compound (18 mg, yield: 74%) was obtained in the same manner as in Example 1, with the exception that 4-bromo-2-fluoro-1-nitrobenzene was used instead of 1-bromo-3-fluoro-2-nitrobenzene in Step 1-5 of Example 1, and (3-chloro-4-fluorophenyl)boronic acid was used instead of phenylboronic acid in Step 1-9 of Example 1.

$^1$H-NMR (500 MHz, DMSO-$d_6$): δ 8.09 (s, 1H), 7.86 (m, 2H), 7.69 (m, 2H), 7.51 (m, 2H), 5.39 (dd, 2H), 4.83 (d, 1H), 3.00 (m, 1H), 2.98 (dd, 1H), 2.83 (d, 1H), 2.70 (m, 1H), 2.41 (m, 2H), 1.91 (d, 1H), 1.59 (d, 1H), 1.34 (m, 1H), 1.27 (m, 1H).

EXAMPLE 34

Preparation of 1-(6-(3-chloro-5-methylphenyl)-1H-benzo[d]imidazol-1-yl)-3-((2R,3S)-3-hydroxypiperidin-2-yl)propan-2-one

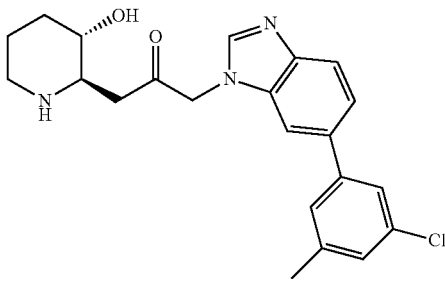 [SMILES: Cc1cc(Cl)cc(-c2ccc3ncn(CC(=O)C[C@H]4NCCC[C@@H]4O)c3c2)c1]

The title compound (17 mg, yield: 70%) was obtained in the same manner as in Example 1, with the exception that 4-bromo-2-fluoro-1-nitrobenzene was used instead of 1-bromo-3-fluoro-2-nitrobenzene in Step 1-5 of Example 1, and (3-chloro-5-methylphenyl)boronic acid was used instead of phenylboronic acid in Step 1-9 of Example 1.

$^1$H-NMR (500 MHz, DMSO-d$_6$): δ 8.09 (s, 1H), 7.84 (s, 1H), 7.71 (d, 1H), 7.51 (m, 3H), 7.23 (s, 1H), 5.38 (dd, 2H), 4.88 (d, 1H), 3.05 (m, 1H), 2.89 (dd, 1H), 2.86 (d, 1H), 2,73 (m, 1H), 2.44 (m, 2H), 2.37 (s, 3H), 1.92 (d, 1H), 1.60 (d, 1H), 1.36 (m, 1H), 1.27 (m, 1H).

EXAMPLE 35

Preparation of 1-(6-(3-chloro-5-methoxyphenyl)-1H-benzo[d]imidazol-1-yl)-3-((2R,3S)-3-hydroxypiperidin-2-yl)propan-2-one

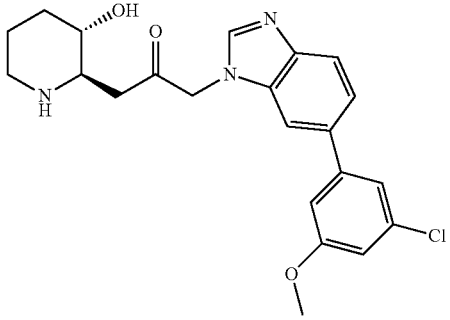 [SMILES: COc1cc(Cl)cc(-c2ccc3ncn(CC(=O)C[C@H]4NCCC[C@@H]4O)c3c2)c1]

The title compound (19 mg, yield: 75%) was obtained in the same manner as in Example 1, with the exception that 4-bromo-2-fluoro-1-nitrobenzene was used instead of 1-bromo-3-fluoro-2-nitrobenzene in Step 1-5 of Example 1, and (3-chloro-5-methoxyphenyl)boronic acid was used instead of phenylboronic acid in Step 1-9 of Example 1.

$^1$H-NMR (500 MHz, DMSO-d$_6$): δ 8.09 (s, 1H), 7.85 (s, 1H), 7.70 (d, 1H), 7.55 (d, 1H), 7.35 (s, 1H), 7.19 (s, 1H), 7.00 (s, 1H), 5.40 (dd, 2H), 4.91 (d, 1H), 3.81 (s, 3H), 3.06 (m, 1H), 2.96 (dd, 1H), 2.87 (d, 1H), 2.75 (m, 1H), 2.40 (m, 1H), 1.89 (d, 1H), 1.60 (d, 1H), 1.36 (m, 1H), 1.27 (m, 1H).

EXAMPLE 36

Preparation of 3-chloro-5-(1-(3-((2R,3S)-3-hydroxypiperidin-2-yl)-2-oxopropyl)-1H-benzo[d]imidazol-6-yl)benzonitrile

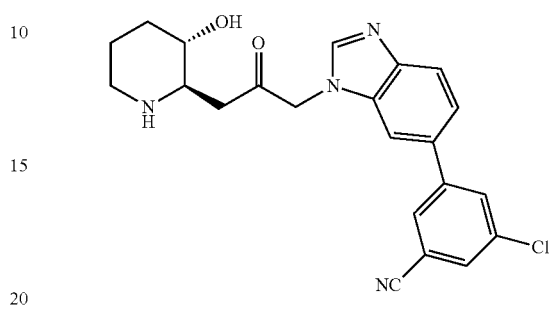

The title compound (17 mg, yield: 69%) was obtained in the same manner as in Example 1, with the exception that 4-bromo-2-fluoro-1-nitrobenzene was used instead of 1-bromo-3-fluoro-2-nitrobenzene in Step 1-5 of Example 1, and (3-chloro-5-cyanophenyl)boronic acid was used instead of phenylboronic acid in Step 1-9 of Example 1.

$^1$H-NMR (500 MHz, DMSO-d$_6$): δ 8.14 (m, 3H), 7.99 (m, 2H), 7.75 (d, 1H), 7.65 (d, 1H), 5.39 (dd, 2H), 4.90 (d, 1H), 3.05 (m, 1H), 3.00 (dd, 1H), 2.86 (d, 1H), 2.74 (m, 1H), 2.42 (m, 1H), 1.92 (d, 1H), 1.60 (d, 1H), 1.36 (m, 1H), 1.27 (m, 1H).

EXAMPLE 37

Preparation of 1-(6-(1H-pyrazol-4-yl)-1H-benzo[d]imidazol-1-yl)-3-((2R,3S)-3-hydroxypiperidin-2-yl)propan-2-one

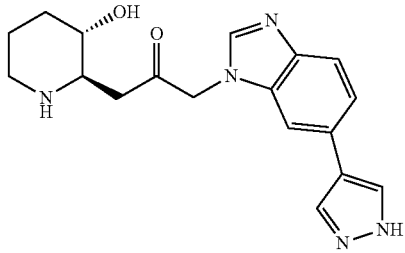 [SMILES: O=C(C[C@H]1NCCC[C@@H]1O)Cn1cnc2ccc(-c3cn[nH]c3)cc21]

The title compound (10 mg, yield: 50%) was obtained in the same manner as in Example 1, with the exception that 4-bromo-2-fluoro-1-nitrobenzene was used instead of 1-bromo-3-fluoro-2-nitrobenzene in Step 1-5 of Example 1, and tert-butyl 4-(4,4,5,5-tetramethyl-1,3,2-dioxoborolan-2-yl)-1H-pyrazol-1-carboxylate was used instead of phenylboronic acid in Step 1-9 of Example 1.

$^1$H-NMR (500 MHz, DMSO-d$_6$): δ 8.10 (s, 1H), 7.89 (s, 1H), 7,87 (s, 1H), 7.66 (s, 1H), 7.60 (d, 1H), 7.45 (d, 1H), 5.32 (dd, 2H), 4.88 (d, 1H), 3.04 (m, 1H), 2.97 (dd, 1H), 2.85 (d, 1H), 2.72 (m, 1H), 2.45 (m, 2H), 1.93 (m, 1H), 1.58 (m, 1H), 1.36 (m, 1H), 1.27 (m, 1H).

EXAMPLE 38

Preparation of 1-(6-(1H-pyrazol-3-yl)-1H-benzo[d]imidazol-1-yl)-3-((2R,3S)-3-hydroxypiperidin-2-yl)propan-2-one

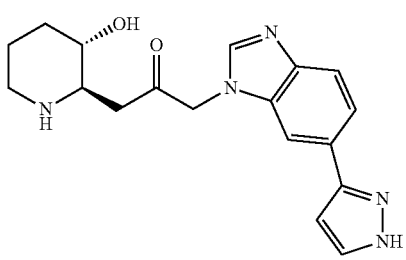 [SMILES: O=C(C[C@H]1NCCC[C@@H]1O)Cn1cnc2ccc(-c3cc[nH]n3)cc21]

The title compound (14 mg, yield: 60%) was obtained in the same manner as in Example 1, with the exception that 4-bromo-2-fluoro-1-nitrobenzene was used instead of 1-bromo-3-fluoro-2-nitrobenzene in Step 1-5 of Example 1, and (1-(tert-butoxy-carbonyl)-1H-pyrazol-3-yl)boronic acid was used instead of phenylboronic acid in Step 1-9 of Example 1.

$^1$H-NMR (500 MHz, DMSO-$d_6$): δ 8.10 (s, 1H), 7.77 (m, 3H), 7.30 (m, 1H), 6.53 (d, 1H), 5.32 (dd, 2H), 4.88 (d, 1H), 3.04 (m, 1H), 2.97 (dd, 1H), 2.85 (d, 1H), 2.72 (m, 1H), 2.45 (m, 2H), 1.93 (m, 1H), 1.58 (m, 1H), 1.36 (m, 1H), 1.27 (m, 1H).

EXAMPLE 39

Preparation of 1-((2R,3S)-3-hydroxypiperidin-2-yl)-3-(6-(thiazol-4-yl)-1H-benzo[d]imidazol-1-yl)propan-2-one

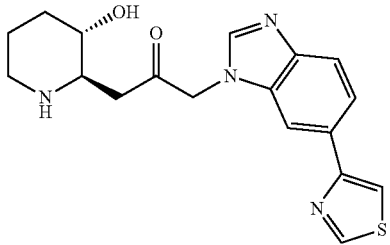 [SMILES: O=C(C[C@H]1NCCC[C@@H]1O)Cn1cnc2ccc(-c3cscn3)cc21]

The title compound (15 mg, yield: 62%) was obtained in the same manner as in Example 1, with the exception that 4-bromo-2-fluoro-1-nitrobenzene was used instead of 1-bromo-3-fluoro-2-nitrobenzene in Step 1-5 of Example 1, and thiazol-4-yl boronic acid was used instead of phenylboronic acid in Step 1-9 of Example 1.

$^1$H-NMR (500 MHz, DMSO-$d_6$): δ 9.19 (s, 1H), 8.10 (m, 3H), 7.85 (d, 1H), 7.69 (d, 1H), 5.39 (dd, 2H), 4.82 (d, 1H), 3.01 (m, 1H), 2.99 (dd, 1H), 2.85 (d, 1H), 2.69 (m, 1H), 2.44 (m, 2H), 1.91 (m, 1H), 1.60 (d, 1H), 1.38 (m, 1H), 1.25 (m, 1H).

EXAMPLE 40

Preparation of 5-(1-(3-((2R,3S)-3-hydroxypiperidin-2-yl)-2-oxopropyl)-1H-benzo[d]imidazol-6-yl)pyridin-2(1H)-one

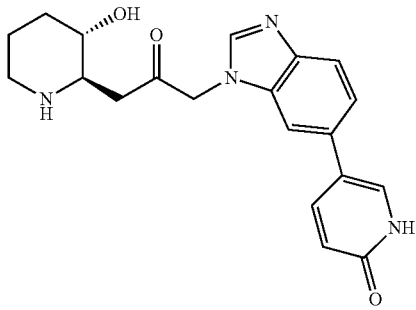 [SMILES: O=C(C[C@H]1NCCC[C@@H]1O)Cn1cnc2ccc(-c3ccc(=O)[nH]c3)cc21]

The title compound (13 mg, yield: 55%) was obtained in the same manner as in Example 1, with the exception that 4-bromo-2-fluoro-1-nitrobenzene was used instead of 1-bromo-3-fluoro-2-nitrobenzene in Step 1-5 of Example 1, and (6-oxo-1,6-dihydropyridin-3-yl)bronic acid was used instead of phenylboronic acid in Step 1-9 of Example 1.

$^1$H-NMR (500 MHz, DMSO-$d_6$): δ 8.06 (d, 1H), 8.04 (s, 1H), 7.82 (dd, 1H), 7.67 (m, 2H), 7.41 (d, 1H), 6.50 (m, 1H), 5.33 (dd, 2H), 4.90 (d, 1H), 3.05 (m, 1H), 2.98 (dd, 1H), 2.85 (d, 1H), 2.73 (m, 1H), 2.42 (m, 2H), 1.90 (m, 1H), 1.61 (d, 1H), 1.38 (m, 1H), 1.29 (m, 1H).

EXAMPLE 41

Preparation of 1-(6-(3-chlorophenyl)-1H-imidazo[4,5-b]pyridin-1-yl)-3-((2R,3S)-3-hydroxypiperidin-2-yl)propan-2-one

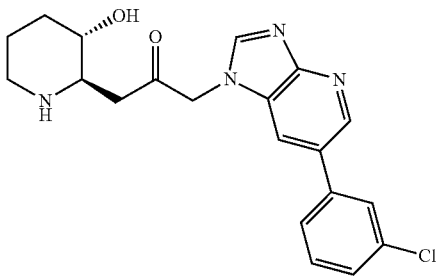 [SMILES: O=C(C[C@H]1NCCC[C@@H]1O)Cn1cnc2ncc(-c3cccc(Cl)c3)cc21]

Step 41-1: Preparation of benzyl (2R,3S)-2-(3-(6-bromo-1H-imidazo[4,5-b]pyridin-1-yl)-2-oxopropyl)-3-((tert-butyldimethylsilyl)oxy)piperidine-1-carboxylate 6-Bromo-3H-imidazo[4,5-b]pyridine (204 mg, 1.03 mmol) was dissolved in N,N-dimethylformamide (3 mL, 0.34 M) to which potassium carbonate (285 mg, 2.06 mmol) was added and then stirred at room temperature for 10 minutes. Then, benzyl (2R,3S)-2-(3-bromo-2-oxopropyl)-3-((tert-butyldimethylsilyl)oxy)piperidine-1-carboxylate (500 mg, 1.03 mmol) was added thereto and stirred at room temperature for 3 hours. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (dichloromethane:methanol=10:1) to give the title compound (266 mg, yield: 43%).

Step 41-2: Preparation of benzyl (2R,3S)-3-((tert-butyldimethylsilyl)oxy)-2-(3-(6-(3-chlorophenyl)-1H-imidazo[4,5-b]pyridin-1-yl)-2-oxopropyl)piperidin-1-carboxylate Benzyl (2R,3S)-2-(3-(6-bromo-1H-imidazo[4,5-b]pyridin-1-yl)-2-oxopropyl)-3-((tert-butyldimethylsilyl)oxy)piperidin-1-carboxylate (75 mg, 0.13 mmol) obtained from Step 41-1 was dissolved in N,N-dimethylformamide (2 mL, 0.07 M) to which (3-chlorophenyl)boronic acid (29 mg, 0.19 mmol), tetrakis(triphenylphosphine)palladium (30 mg, 0.03 mmol) and 2M sodium carbonate (0.25 mL, 0.5 mmol) were sequentially added and then stirred at room temperature for 5 minutes. Then, the mixture was reacted at 150° C. for 30 minutes using a microwave. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=1:2) to give the title compound (62 mg, yield: 78%).

Step 41-3: Preparation of 1-(6-(3-chlorophenyl)-1H-imidazo[4,5-b]pyridin-1-yl)-3-((2R,3S)-3-hydroxypiperidin-2-yl)propan-2-one Benzyl (2R,3S)-3-((tert-butyldimethylsilyl)oxy)-2-(3-(6-(3-chlorophenyl)-1H-imidazo[4,5-b]pyridin-1-yl)-2-oxopropyl)piperidin-1-carboxylate (62 mg, 0.1 mmol) obtained from Step 41-2 was dissolved in 6N hydrogen chloride solution (3 mL, 0.03 M) and then stirred under reflux for 1 hour. When the reaction was completed, the reaction solution was cooled to 0° C., neutralized (pH 7) with potassium carbonate and then extracted with a mixed solution of chloroform and a small amount of acetone. The organic layer was collected, dried over magnesium sulfate, filtered and concentrated under reduced pressure, and then recrystallized with diethylether to give the title compound (28 mg, yield: 75%).

$^1$H-NMR (500 MHz, DMSO-d$_6$): δ 8.76 (d, 1H), 8.35 (s, 1H), 8.30 (d, 1H), 7.78 (s, 1H), 7.73 (d, 1H), 7.53 (t, 1H), 7.47 (d, 1H), 5.43 (dd, 2H), 4.86 (d, 1H), 3.04 (m, 1H), 2.99 (dd, 1H), 2.83 (d, 1H), 2.71 (m, 1H), 2.46 (m, 1H), 2.39 (m, 1H), 1.90 (m, 1H), 1.59 (d, 1H), 1.35 (m, 1H), 1.23 (m, 1H).

EXAMPLE 42

Preparation of 1-((2R,3S)-3-hydroxypiperidin-2-yl)-3-(6-(3-(trifluoromethyl)phenyl)-1H-imidazo[4,5-b]pyridin-1-yl)propan-2-one

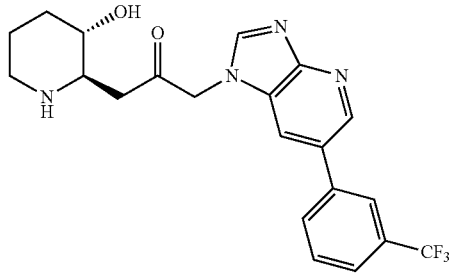 [SMILES: O=C(C[C@H]1NCCC[C@@H]1O)Cn1cnc2ncc(-c3cccc(C(F)(F)F)c3)cc21]

The title compound (33 mg, yield: 76%) was obtained in the same manner as in Example 41, with the exception that (3-(trifluoromethyl)phenyl)boronic acid was used instead of (3-chlorophenyl)boronic acid.

$^1$H-NMR (500 MHz, DMSO-d$_6$): δ 8.80 (d, 1H), 8.37 (s, 1H), 8.34 (d, 1H), 8.07 (d, 1H), 8.03 (s, 1H), 7.76 (m, 2H), 5.45 (dd, 2H), 4.87 (d, 1H), 3.03 (m, 1H), 2.98 (dd, 1H), 2.81 (d, 1H), 2.71 (m, 1H), 2.46 (m, 1H), 2.38 (m, 1H), 1.91 (m, 1H), 1.58 (d, 1H), 1.36 (m, 1H), 1.24 (m, 1H).

EXAMPLE 43

Preparation of 1-(5-(2-fluorophenyl)-3H-imidazo[4,5-b]pyridin-3-yl)-3-((2R,3S)-3-hydroxypiperidin-2-yl)propan-2-one

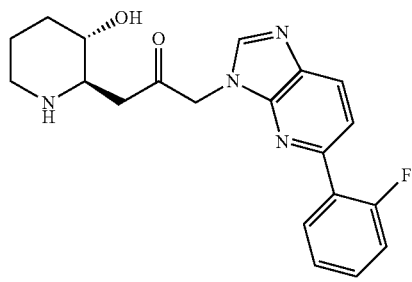 [SMILES: O=C(C[C@H]1NCCC[C@@H]1O)Cn1cnc2ccc(-c3ccccc3F)nc21]

Step 43-1: Preparation of benzyl (2R,3S)-2-(3-(5-bromo-3H-imidazo[4,5-b]pyridin-3-yl)-2-oxopropyl)-3-((tert-butyldimethylsilyl)oxy)piperidine-1-carboxylate 5-Bromo-1H-imidazo[4,5-b]pyridine (245 mg, 1.24 mmol) was dissolved in N,N-dimethylformamide (5 mL, 0.25 M) to which potassium carbonate (324 mg, 2.48 mmol) was added and then stirred at room temperature for 10 minutes. Then, benzyl (2R,3S)-2-(3-bromo-2-oxopropyl)-3-((tert-butyldimethylsilyl)oxy)piperidine-1-carboxylate (600 mg, 1.24 mmol) was added thereto and stirred at room temperature for 3 hours. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (dichloromethane:methanol=10:1) to give the title compound (300 mg, yield: 40%).

Step 43-2: Preparation of benzyl (2R,3S)-3-((tert-butyldimethylsilyl)oxy)-2-(3-(5-(2-fluorophenyl)-3H-imidazo[4,5-b]pyridin-3-yl)-2-oxopropyl)piperidine-1-carboxylate Benzyl (2R,3S)-2-(3-(5-bromo-3H-imidazo[4,5-b]pyridin-3-yl)-2-oxopropyl)-3-((tert-butyldimethylsilyl)oxy)piperidine-1-carboxylate (50 mg, 0.08 mmol) obtained from Step 43-1 was dissolved in N,N-dimethylformamide (2 mL, 0.05 M) to which (2-fluorophenyl)boronic acid (18 mg, 0.13 mmol), tetrakis(triphenylphosphine)palladium (20 mg, 0.02 mmol) and 2M sodium carbonate (0.2 mL, 0.33 mmol) were sequentially added and then stirred at room temperature for 5 minutes. Then, the mixture was reacted at 150° C. for 30 minutes using a microwave. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=1:2) to give the title compound (40 mg, yield: 78%).

Step 43-3: Preparation of 1-(5-(2-fluorophenyl)-3H-imidazo[4,5-b]pyridin-3-yl)-3-((2R,3S)-3-hydroxypiperidin-2-yl)propane-2-one Benzyl (2R,3S)-3-((tert-butyldimethylsilyl)oxy)-2-(3-(5-(2-fluorophenyl)-3H-imidazo[4,5-b]pyridin-3-yl)-2-oxopropyl)piperidine-1-carboxylate (40 mg, 0.06 mmol) obtained from Step 43-2 was dissolved in 6N hydrogen chloride solution (3 mL, 0.02 M) and stirred under reflux for 1 hour. When the reaction was completed, the reaction solution was cooled to 0° C., neutralized (pH 7) with potassium carbonate and then extracted with a mixed solution of chloroform and a small amount of acetone. The organic layer was collected, dried over magnesium sulfate, filtered and concentrated under reduced pressure, and then recrystallized with diethylether to give the title compound (17 mg, yield: 70%).

$^1$H-NMR (500 MHz, DMSO-d$_6$): δ 8.37 (s, 1H), 8.19 (d, 1H), 7.95 (t, 1H), 7.71 (d, 1H), 7.48 (dd, 1H), 7.34 (m, 2H), 5.38 (dd, 2H), 4.77 (d, 1H), 3.01 (dd, 2H), 2.78 (d, 1H), 2.68 (m, 1H), 2.46 (m, 1H), 2.356 (t, 1H), 1.93 (m, 1H), 1.57 (d, 1H), 1.33 (m, 1H), 1.23 (m, 1H).

EXAMPLE 44

Preparation of 1-(5-(3-fluorophenyl)-3H-imidazo[4,5-b]pyridin-3-yl)-3-((2R,3S)-3-hydroxypiperidin-2-yl)propan-2-one

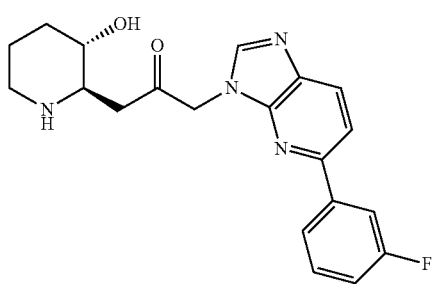 [SMILES: O=C(C[C@H]1NCCC[C@@H]1O)Cn1cnc2ccc(-c3cccc(F)c3)nc21]

The title compound (18 mg, yield: 72%) was obtained in the same manner as in Example 43, with the exception that (3-fluorophenyl)boronic acid was used instead of (2-fluorophenyl)boronic acid.

$^1$H-NMR (500 MHz, DMSO-d$_6$): δ 8.34 (s, 1H), 8.18 (d, 1H), 7.96 (m, 3H), 7.53 (m, 2H), 7.24 (dt, 1H), 5.41 (dd, 2H), 4.80 (d, 1H), 3.02 (m, 2H), 2.82 (d, 1H), 2.70 (m, 1H), 2.54 (m, 1H), 2.38 (m, 1H), 1.92 (m, 1H), 1.59 (d, 1H), 1.37 (m, 1H), 1.27 (m, 1H)

EXAMPLE 45

Preparation of 1-(5-(4-fluorophenyl)-3H-imidazo[4,5-b]pyridin-3-yl)-3-((2R,3S)-3-hydroxypiperidin-2-yl)propan-2-one

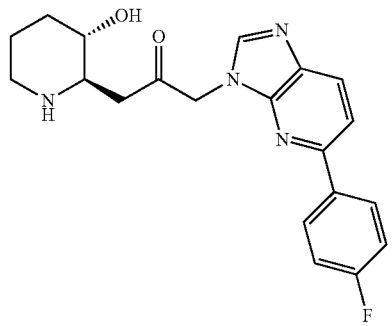 [SMILES: O=C(C[C@H]1NCCC[C@@H]1O)Cn1cnc2ccc(-c3ccc(F)cc3)nc21]

The title compound (17 mg, yield: 70%) was obtained in the same manner as in Example 43, with the exception that (4-fluorophenyl)boronic acid was used instead of (2-fluorophenyl)boronic acid.

$^1$H-NMR (500 MHz, DMSO-d$_6$): δ 8.32 (s, 1H), 8.17 (m, 3H), 7.87 (d, 1H), 7.31(t, 2H), 5.38 (dd, 2H), 4.78 (d, 1H), 3.02 (m, 2H), 2.81 (d, 1H), 2.68 (m, 1H), 2.48 (m, 1H), 2.36 (t, 1H), 1.92 (m, 1H), 1.58 (d, 1H), 1.34 (m, 1H), 1.24 (m, 1H).

EXAMPLE 46

Preparation of 1-(5-(3-chlorophenyl)-3H-imidazo[4,5-b]pyridin-3-yl)-3-((2R,3S)-3-hydroxypiperidin-2-yl)propan-2-one

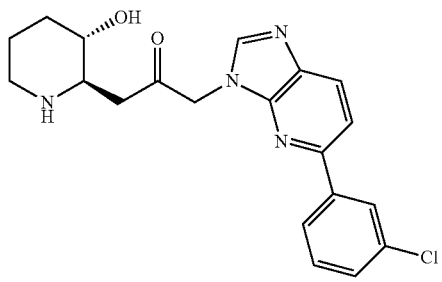 [SMILES: O=C(C[C@H]1NCCC[C@@H]1O)Cn1cnc2ccc(-c3cccc(Cl)c3)nc21]

The title compound (19 mg, yield: 80%) was obtained in the same manner as in Example 43, with the exception that (3-chlorophenyl)boronic acid was used instead of (2-fluorophenyl)boronic acid.

$^1$H-NMR (500 MHz, DMSO-d$_6$): δ 8.34 (s, 1H), 8.18 (m, 2H), 8.10 (d, 1H), 7.95 (d, 1H), 7.51 (t, 1H), 7.48 (d, 1H), 5.41 (dd, 1H), 4.79 (d, 1H), 3.01 (m, 2H), 2.82 (d, 1H), 2.69 (m, 1H), 2.51 (m, 1H), 2.38 (m, 1H), 1.92 (m, 1H), 1.58 (d, 1H), 1.35 (m, 1H), 1.27 (m, 1H).

EXAMPLE 47

Preparation of 1-((2R,3S)-3-hydroxypiperidin-2-yl)-3-(5-(3-(trifluoromethyl)phenyl)-3H-imidazo[4,5-b]pyridin-3-yl)propan-2-one

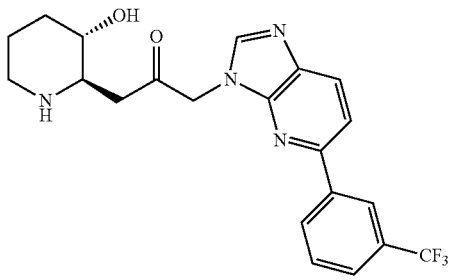

The title compound (20 mg, yield: 75%) was obtained in the same manner as in Example 43, with the exception that (3-(trifluoromethyl)phenyl)boronic acid was used instead of (2-fluorophenyl)boronic acid.

$^1$H-NMR (500 MHz, DMSO-d$_6$): δ 8.44 (d, 2H), 8.37 (d, 1H), 8.21 (dd, 1H), 8.02 (dd, 1H), 7.78 (d, 1H), 7.73 (t, 1H), 5.42 (dd, 2H), 4.78 (d, 1H), 3.03 (d, 2H), 2.80 (d, 1H), 2.68 (m, 1H), 2.52 (m, 1H), 2.36 (t, 1H), 1.92 (m, 1H), 1.58 (d, 1H), 1.34 (m, 1H), 1.24 (m, 1H).

EXAMPLE 48

Preparation of 1-((2R,3S)-3-hydroxypiperidin-2-yl)-3-(7-phenyl-1H-benzo[d]imidazol-1-yl)propan-2-one

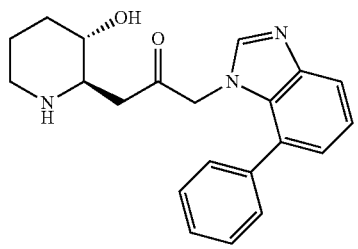 [SMILES: O=C(C[C@H]1NCCC[C@@H]1O)Cn1cnc2cccc(-c3ccccc3)c21]

The title compound (12 mg, yield: 65%) was obtained in the same manner as in Example 1, with the exception that 1-bromo-2-fluoro-3-nitrobenzene was used instead of 1-bromo-3-fluoro-2-nitrobenzene in Step 1-5 of Example 1.

$^1$H-NMR (500 MHz, DMSO-d$_6$): δ 8.04 (s, 1H), 7.70 (d, 1H), 7.45 (m, 3H), 7.27 (m, 3H), 7.01 (dd, 1H), 4.82 (d, 2H), 4.67 (m, 1H), 2.85 (m, 1H), 2.71 (m, 1H), 2.62 (m, 1H), 2.37 (m, 1H), 2.29 (m, 1H), 1.80 (m, 1H), 1.74 (m, 1H), 1.50 (m, 1H), 1.31 (m, 1H), 1.15 (m, 1H)

EXAMPLE 49

Preparation of 1-(7-(3-fluorophenyl)-1H-benzo[d]imidazol-1-yl)-3-((2R,3S)-3-hydroxypiperidin-2-yl)propan-2-one

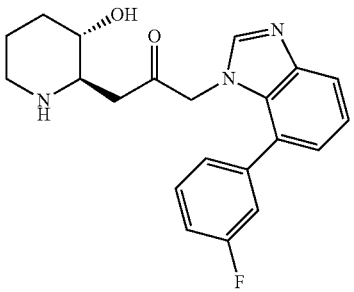

The title compound (27 mg, yield: 80%) was obtained in the same manner as in Example 1, with the exception that 1-bromo-2-fluoro-3-nitrobenzene was used instead of 1-bromo-3-fluoro-2-nitrobenzene in Step 1-5 of Example 1, and (3-fluorophenyl)boronic acid was used instead of phenylboronic acid in Step 1-9 of Example 1.

$^1$H-NMR (500 MHz, DMSO-d$_6$): δ 8.06 (s, 1H), 7.72 (d, 1H), 7.48 (d, 1H), 7.28 (m, 2H), 7.15 (m, 2H), 7.04 (m, 1H), 4.87 (dd, 2H), 4.61 (d, 1H), 2.79 (m, 1H), 2.70 (d, 1H), 2.36 (d, 2H), 2.26 (m, 1H), 1.79 (m, 2H), 1.73 (m, 1H), 1.51 (d, 1H), 1.27 (m, 1H)

EXAMPLE 50

Preparation of 1-(7-(3-chlorophenyl)-1H-benzo[d]imidazol-1-yl)-3-((2R,3S)-3-hydroxypiperidin-2-yl)propan-2-one

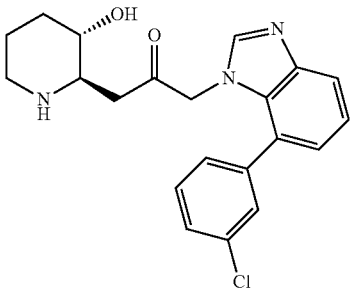 [SMILES: O=C(C[C@H]1NCCC[C@@H]1O)Cn1cnc2cccc(-c3cccc(F)c3)c21]

The title compound (22 mg, yield: 76%) was obtained in the same manner as in Example 1, with the exception that 1-bromo-2-fluoro-3-nitrobenzene was used instead of 1-bromo-3-fluoro-2-nitrobenzene in Step 1-5 of Example 1, and (3-chlorophenyl)boronic acid was used instead of phenylboronic acid in Step 1-9 of Example 1.

$^1$H-NMR (500 MHz, DMSO-d$_6$): δ 8.04 (s, 1H), 7.70 (d, 1H), 7.49 (m, 1H), 7.45 (m, 1H), 7.32 (s, 1H), 7.23 (m, 2H), 7.02 (m, 1H), 4.85 (d, 2H), 4.58 (m, 1H), 2.77 (m, 1H), 2.69 (d, 1H), 2.34 (m, 2H), 2.26 (m, 1H), 1.75 (m, 2H), 1.50 (m, 1H), 1.27 (m, 1H), 1.13 (m, 1H)

EXAMPLE 51

Preparation of 1-(7-(4-chlorophenyl)-1H-benzo[d]imidazol-1-yl)-3-((2R,3S)-3-hydroxypiperidin-2-yl)propan-2-one

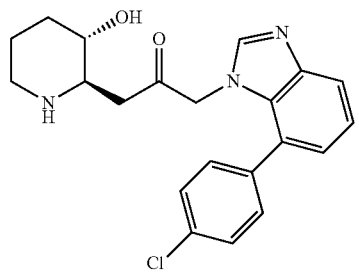 [SMILES: O=C(C[C@H]1NCCC[C@@H]1O)Cn1cnc2cccc(-c3ccc(Cl)cc3)c21]

The title compound (18 mg, yield: 72%) was obtained in the same manner as in Example 1, except that 1-bromo-2-fluoro-3-nitrobenzene was used instead of 1-bromo-3-fluoro-2-nitrobenzene in Step 1-5 of Example 1, and (4-chlorophenyl)boronic acid was used instead of phenylboronic acid in Step 1-9 of Example 1.

$^1$H-NMR (500 MHz, DMSO-$d_6$): δ 8.04 (s, 1H), 7.69 (d, 1H), 7.48 (d, 2H), 7.28 (d, 2H), 7.24 (t, 1H), 6.98 (d, 1H), 4.86 (s, 2H), 4.60 (m, 1H), 2.79 (m, 1H), 2.70 (d, 1H), 2.36 (m, 2H), 2.25 (m, 1H), 1.76 (m, 2H), 1.50 (m, 1H), 1.28 (m, 1H), 1.25 (m, 1H)

EXAMPLE 52

Preparation of 1-((2R,3S)-3-hydroxypiperidin-2-yl)-3-(7-(2-(trifluoromethyl)phenyl)-1H-benzo[d]imidazol-1-yl)propan-2-one

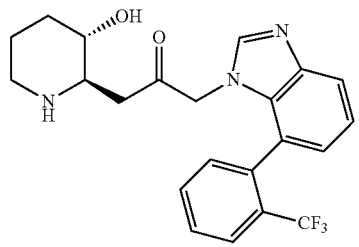 [SMILES: O=C(C[C@H]1NCCC[C@@H]1O)Cn1cnc2cccc(-c3ccccc3C(F)(F)F)c21]

The title compound (11 mg, yield: 55%) was obtained in the same manner as in Example 1, with the exception that 1-bromo-2-fluoro-3-nitrobenzene was used instead of 1-bromo-3-fluoro-2-nitrobenzene in Step 1-5 of Example 1, and (2-trifluorophenyl)boronic acid was used instead of phenylboronic acid in Step 1-9 of Example 1.

$^1$H-NMR (500 MHz, DMSO-$d_6$): δ 7.99 (d, 1H), 7.88 (m, 1H), 7.68 (m, 3H), 7.22 (m, 2H), 6.96 (d, 1H), 4.88 (t, 1H), 4.57 (m, 1H), 4.22 (t, 1H), 2.82 (m, 1H), 2.75 (m, 1H), 2.45 (m, 1H), 2.25 (m, 1H), 1.79 (m, 2H), 1.65 (m, 1H), 1.51 (m, 1H), 1.22 (m, 1H), 1.14 (m, 1H)

EXAMPLE 53

Preparation of 1-((2R,3S)-3-hydroxypiperidin-2-yl)-3-(7-(3-(trifluoromethyl)phenyl)-1H-benzo[d]imidazol-1-yl)propan-2-one

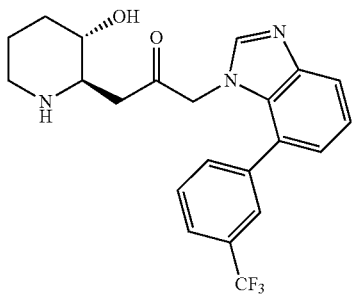 [SMILES: O=C(C[C@H]1NCCC[C@@H]1O)Cn1cnc2cccc(-c3cccc(C(F)(F)F)c3)c21]

The title compound (19 mg, yield: 64%) was obtained in the same manner as in Example 1, with the exception that 1-bromo-2-fluoro-3-nitrobenzene was used instead of 1-bromo-3-fluoro-2-nitrobenzene in Step 1-5 of Example 1, and (3-trifluorophenyl)boronic acid was used instead of phenylboronic acid in Step 1-9 of Example 1.

$^1$H-NMR (500 MHz, DMSO-$d_6$): δ 8.07 (s, 1H), 7.80 (d, 1H), 7.74 (d, 1H), 7.68 (t, 1H), 7.61 (m, 2H), 7.28 (t, 1H), 7.06 (d, 1H), 4.86 (d, 2H), 4.58 (m, 1H), 2.75 (m, 1H), 2.66 (d, 1H), 2.35 (d, 1H), 2.25 (m, 2H), 1.79 (d, 1H), 1.65 (m, 1H), 1.57 (m, 1H), 1.24 (m, 1H), 1.17 (m, 1H)

EXAMPLE 54

Preparation of 1-((2R,3S)-3-hydroxypiperidin-2-yl)-3-(7-(4-(trifluoromethyl)phenyl)-1H-benzo[d]imidazol-1-yl)propan-2-one

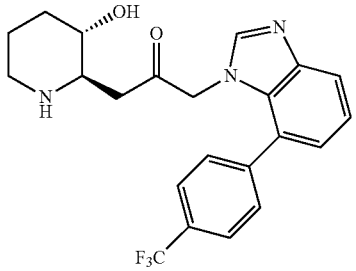 [SMILES: O=C(C[C@H]1NCCC[C@@H]1O)Cn1cnc2cccc(-c3ccc(C(F)(F)F)cc3)c21]

The title compound (25 mg, yield: 75%) was obtained in the same manner as in Example 1, with the exception that 1-bromo-2-fluoro-3-nitrobenzene was used instead of 1-bromo-3-fluoro-2-nitrobenzene in Step 1-5 of Example 1, and (4-trifluorophenyl)boronic acid was used instead of phenylboronic acid in Step 1-9 of Example 1.

$^1$H-NMR (500 MHz, DMSO-$d_6$): δ 8.06 (s, 1H), 7.78 (d, 2H), 7.73 (d, 1H), 7.50 (d, 2H), 7.27 (t, 1H), 7.04 (d, 1H), 4.86 (d, 2H), 4.53 (m, 1H), 2.74 (m, 1H), 2.68 (d, 1H), 2.31 (m, 2H), 2.20 (m, 1H), 1.79 (m, 1H), 1.68 (m, 1H), 1.49 (m, 1H), 1.25 (m, 1H), 1.12 (m, 1H)

EXAMPLE 55

Preparation of 1-(2-(hydroxymethyl)-5-phenyl-1H-benzo[d]imidazol-1-yl)-3-((2R,3S)-3-hydroxypiperidin-2-yl)propan-2-one

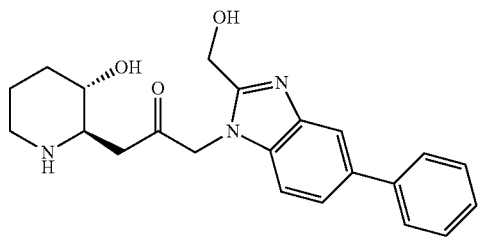 [SMILES: O=C(C[C@H]1NCCC[C@@H]1O)Cn1c(CO)nc2cc(-c3ccccc3)ccc21]

Step 55-1: Preparation of benzyl (2R,3S)-2-(3-((4-bromo-2-nitrophenyl)amino)-2-hydroxypropyl)-3-((tert-butyldimethylsilyl)oxy)piperidin-1-carboxylate Benzyl (2R,3S)-2-(3-amino-2-hydroxypropyl)-3-(tert-butyldimethylsilyl)oxy)piperidine-1-carboxylate (980 mg, 2.21 mmol) obtained from Step 1-4 of Example 1 was dissolved in N,N-dimethylformamide (10 mL, 0.22 M) to which N,N-diisopropylethylamine (0.77 mL, 4.43 mmol) and 4-bromo-1-fluoro-2-nitrobenzene (487 mg, 2.21 mmol) were added and then stirred at 50° C. for 6 hours. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=3:1) to give the title compound (580 mg, yield: 42%).

Step 55-2: Preparation of benzyl (2R,3S)-2-(3-((4-bromo-2-(2-((tert-butyldiphenylsilyl)oxy)acetamido)phenyl)amino)-2-hydroxypropyl)-3-((tert-butyldimethylsilyl)oxy)piperidine-1-carboxylate Benzyl (2R,3S)-2-(3-((4-bromo-2-nitrophenyl)amino)-2-hydroxypropyl)-3-((tert-butyldimethylsilyl)oxy)piperidin-1-carboxylate (550 mg, 0.88 mmol)obtained from Step 55-1 was dissolved in methyl alcohol (6 mL, 0.15 M) to which Raney nickel (1 mL) was added, filled with hydrogen gas and then stirred at room temperature. When the reaction was completed, the organic layer was dried and then dissolved in N,N-dimethylformamide (10 mL, 0.09 M) to which 2-((tert-butyldiphenylsilyl)oxy)acetic acid (280 mg, 0.88 mmol), O-(benzotriazol-1-yl)-N,N,N',N'-tetramethyluronium hexafluorophosphate (502 mg, 1.32 mmol), and diisopropylethylamine(0.38 mL, 2.21 mmol) were added and then stirred at room temperature for 3 hours. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=3:1) to give the title compound (365 mg, yield: 46%).

Step 55-3: Preparation of benzyl (2R,3S)-2-(3-(5-bromo-2-(((tert-butyldiphenylsilyl)oxy)methyl)-1H-benzo[d]imidazol-1-yl)-2-hydroxypropyl)-3-((tert-butyldimethylsilyl)oxy)piperidine-1-carboxylate Benzyl (2R,3S)-2-(3-((4-bromo-2-(2-((tert-butyldiphenylsilyl)oxy)acetamido)phenyl)amino)-2-hydroxypropyl)-3-((tert-butyldimethylsilyl)oxy)piperidine-1-carboxylate (163 mg, 0.18 mmol) obtained from Step 55-2 was added and dissolved in acetic acid (6 mL, 0.03 M) and then stirred at 65° C. for 3 hours. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=3:1) to give the title compound (144 mg, yield: 92%).

Step 55-4: Preparation of benzyl (2R,3S)-2-(3-(5-bromo-2-(((tert-butyldiphenylsilyl)oxy)methyl)-1H-benzo[d]imidazol-1-yl)-2-oxopropyl)-3-((tert-butyldimethylsilyl)oxy)piperidine-1-carboxylate Benzyl (2R,3S)-2-(3-(5-bromo-2-(((tert-butyldiphenylsilyl)oxy)methyl)-1H-benzo[d]imidazol-1-yl)-2-hydroxypropyl)-3-((tert-butyldimethylsilyl)oxy)piperidine-1-carboxylate (144 mg, 0.17 mmol) obtained from Step 55-3 was dissolved in dichloromethane (5 mL, 0.04 M) to which 1,1,1-triacetoxy-1,1-dihydro-1,2-benziodoxol-3(1H)-one (105 mg, 0.25 mmol) was added at 0° C. and stirred at the same temperature for 1 hour, followed by stirring at room temperature for 3 hours. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=3:1) to give the title compound (126 mg, yield: 88%).

Step 55-5: Preparation of benzyl (2R,3S)-3-((tert-butyldimethylsilyl)oxy)-2-(3-(2-(((tert-butyldiphenylsilyl)oxy)methyl)-5-phenyl-1H-bebzo[d]imidazol-1-yl)-2-oxopropyl)piperidine-1-carboxylate Benzyl (2R,3S)-2-(3-(5-bromo-2-(((tert-butyldiphenylsilyl)oxy)methyl)-1H-benzo[d]imidazol-1-yl)-2-oxopropyl)-3-((tert-butyldimethylsilyl)oxy)piperidine-1-carboxylate (63 mg, 0.07 mmol) obtained from Step 55-4 was dissolved in N,N-dimethylformamide (2 mL, 0.04 M) to which phenylboronic acid (13 mg, 0.11 mmol), tetrakis(triphenylphosphine)palladium (17 mg, 0.02 mmol) and 2M sodium carbonate (0.15 mL, 0.29 mmol) were sequentially added and then stirred at room temperature for 5 minutes. Then, the mixture was reacted at 150° C. for 30 minutes using a microwave. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethylacetate=3:1) to give the title compound (26 mg, yield: 41%).

Step 55-6: Preparation of 1-(2-(hydroxymethyl)-5-phenyl-1H-benzo[d]imidazol-1-yl)-3-((2R,3S)-3-hydroxypiperidin-2-yl)propan-2-one Benzyl (2R,3S)-3-((tert-butyldimethylsilyl)oxy)-2-(3-(2-(((tert-butyldiphenylsilyl)oxy)methyl)-5-phenyl-1H-benzo[d]imidazol-1-yl)-2-oxopropyl)piperidine-1-carboxylate (26 mg, 0.03 mmol) obtained from Step 55-5 was dissolved in 6N hydrogen chloride solution (3 mL, 0.02 M) and then stirred under reflux for 1 hour. When the reaction was completed, the reaction solution was cooled to 0° C., neutralized (pH 7) with potassium carbonate and then extracted with a mixed solution of chloroform and a small amount of acetone. The organic layer was collected, dried over magnesium sulfate, filtered and concentrated under reduced pressure, and then recrystallized with diethylether to give the title compound (8 mg, yield: 70%).

$^1$H-NMR (500 MHz, DMSO-d$_6$): δ 7.83 (s, 1H), 7.69 (d, 2H), 7.52 (m, 2H), 7.45 (t, 2H), 7.32 (t, 1H), 5.38 (dd, 2H), 4.82 (d, 1H), 3.00 (m, 1H), 2.98 (dd, 1H), 2.83 (d, 1H), 2.68 (m, 1H), 2.42 (m, 2H), 1.91 (m, 1H), 1.59 (d, 1H), 1.35 (m, 1H), 1.25 (m, 1H).

EXAMPLE 56

Preparation of 1-(5-(3-fluorophenyl)-2-(hydroxymethyl)-1H-benzo[d]imidazol-1-yl)-3-((2R,3S)-3-hydroxypiperidin-2-yl)propan-2-one

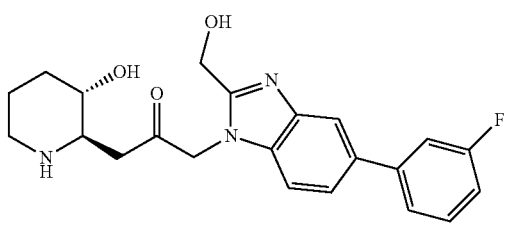 [SMILES: O=C(C[C@H]1NCCC[C@@H]1O)Cn1c(CO)nc2cc(-c3cccc(F)c3)ccc21]

The title compound (10 mg, yield: 75%) was obtained in the same manner as in Example 55, with the exception that (3-fluorophenyl)boronic acid was used instead of phenylboronic acid in Step 55-5 of Example 55.

$^1$H-NMR (500 MHz, DMSO-d$_6$): δ 7.90 (s, 1H), 7.54 (m, 5H), 7.15 (t, 1H), 5.39 (dd, 2H), 4.82 (d, 1H), 4.61 (s, 2H), 3.00 (m, 1H), 2.98 (dd, 1H), 2.83 (d, 1H), 2.68 (m, 1H), 2.42 (m, 2H), 1.91 (m, 1H), 1.35 (m, 1H), 1.23 (m, 1H).

EXAMPLE 57

Preparation of 1-(2-(hydroxymethyl)-6-phenyl-1H-benzo[d]imidazol-1-yl)-3-((2R,3S)-3-hydroxypiperidin-2-yl)propan-2-one

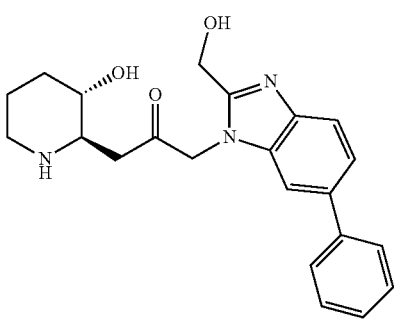 [SMILES: O=C(C[C@H]1NCCC[C@@H]1O)Cn1c(CO)nc2ccc(-c3ccccc3)cc21]

The title compound (10 mg, yield: 75%) was obtained in the same manner as in Example 55, with the exception that 4-bromo-2-fluoro-1-nitrobenzene was used instead of 4-bromo-1-fluoro-2-nitrobenzene in Step 56-1 of Example 55.

$^1$H-NMR (500 MHz, DMSO-d$_6$): δ 7.78 (s, 1H), 7.69 (d, 2H), 7.64 (m, 1H), 7.47 (m, 3H), 7.33 (m, 1H), 5.42 (dd, 2H), 4.81 (d, 1H), 4.60 (s, 2H), 2.99 (m, 1H), 2.82 (d, 1H), 2.69 (m, 1H), 2.41 (m, 2H), 1.91 (m, 1H), 1.59 (d, 1H), 1.34 (m,1H), 1.245 (m, 2H).

EXAMPLE 58

Preparation of 1-(6-(2-fluorophenyl)-2-(hydroxymethyl)-1H-benzo[d]imidazol-1-yl)-3-((2R,3S)-3-hydroxypiperidin-2-yl)propan-2-one

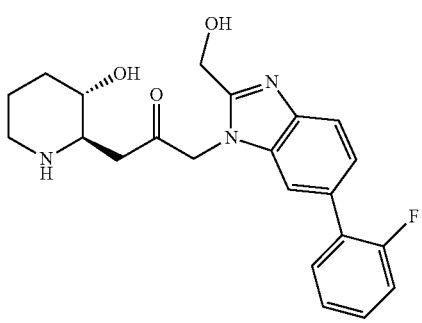 [SMILES: O=C(C[C@H]1NCCC[C@@H]1O)Cn1c(CO)nc2ccc(-c3ccccc3F)cc21]

The title compound (10 mg, yield: 75%) was obtained in the same manner as in Example 55, with the exception that 4-bromo-2-fluoro-3-nitrobenzene was used instead of 4-bromo-1-fluoro-2-nitrobenzene in Step 55-1 of Example 55, and (2-fluorophenyl)boronic acid was used instead of phenylboronic acid in Step 55-5 of Example 55.

$^1$H-NMR (500 MHz, DMSO-d$_6$): δ 7.66 (m, 2H), 7.53 (m, 1H), 7.39 (m, 1H), 7.34 (d, 1H), 7.29 (m, 2H), 5.39 (dd, 2H), 4.80 (d, 1H), 4.61 (s, 2H), 2.99 (m, 2H), 2.79 (m, 1H), 2.68 (m, 1H), 2.44 (dd, 1H), 2.36 (t, 1H), 1.90 (m, 1H), 1.58 (d, 1H), 1.33 (m, 1H), 1.26 (m, 1H).

EXAMPLE 59

Preparation of 1-(6-(3-fluorophenyl)-2-(hydroxymethyl)-1H-benzo[d]imidazol-1-yl)-3-((2R,3S)-3-hydroxypiperidin-2-yl)propan-2-one

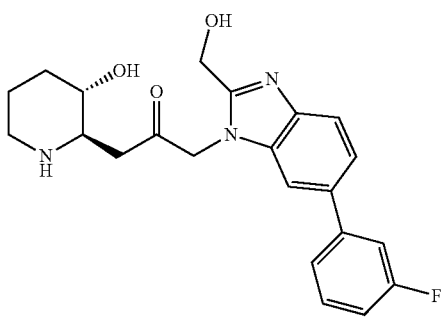 [SMILES: O=C(C[C@H]1NCCC[C@@H]1O)Cn1c(CO)nc2ccc(-c3cccc(F)c3)cc21]

The title compound (16 mg, yield: 78%) was obtained in the same manner as in Example 55, with the exception that 4-bromo-2-fluoro-3-nitrobenzene was used instead of 4-bromo-1-fluoro-2-nitrobenzene in Step 55-1 of Example 55, and (3-fluorophenyl)boronic acid was used instead of phenylboronic acid in Step 55-5 of Example 55.

$^1$H-NMR (500 MHz, DMSO-d$_6$): δ 7.84 (s, 1H), 7.64 (m, 1H), 7.54 (m, 3H), 7.17 (m, 1H), 5.43 (dd, 2H), 4.82 (d, 1H), 4.61 (s, 2H), 2.97 (m, 2H), 2.82 (d, 1H), 2.68 (m, 1h), 2.42 (m, 2H), 1.90 (m, 1H), 1.59 (d, 1H), 1.36 (m, 1h), 1.25 (m, 2H).

EXAMPLE 60

Preparation of 1-(6-(4-fluorophenyl)-2-(hydroxymethyl)-1H-benzo[d]imidazol-1-yl)-3-((2R,3S)-3-hydroxypiperidin-2-yl)propan-2-one

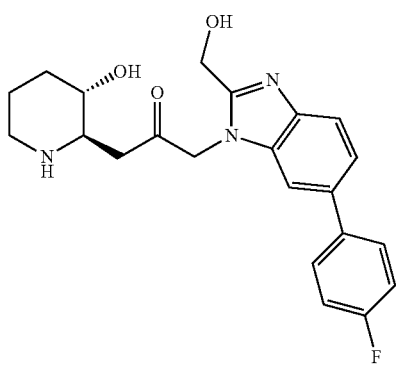 [SMILES: O=C(C[C@H]1NCCC[C@@H]1O)Cn1c(CO)nc2ccc(-c3ccc(F)cc3)cc21]

The title compound (13 mg, yield: 75%) was obtained in the same manner as in Example 55, with the exception that 4-bromo-2-fluoro-3-nitrobenzene was used instead of 4-bromo-1-fluoro-2-nitrobenzene in Step 55-1 of Example 55, and (4-fluorophenyl)boronic acid was used instead of phenylboronic acid in Step 55-5 of Example 55.

$^1$H-NMR (500 MHz, DMSO-d$_6$): δ 7.82 (s, 1H), 7.72 (m, 2H), 7.65 (d, 1H), 7.47 (d, 1H), 7.29 (m, 2H), 5.44 (dd, 2H), 4.64 (s, 2H), 3.20 (m, 1H), 3.06 (dd, 1H), 2.93 (m, 2H), 2.63 (m, 2H), 1.92 (m, 1H), 1.68 (d, 1H), 1.47 (m, 1H), 1.33 (m, 1H).

EXAMPLE 61

Preparation of 1-(2-(hydroxymethyl)-6-(3-(trifluoromethyl)phenyl)-1H-benzo[d]imidazol-1-yl)-3-((2R,3S)-3-hydroxypiperidin-2-yl)propan-2-one

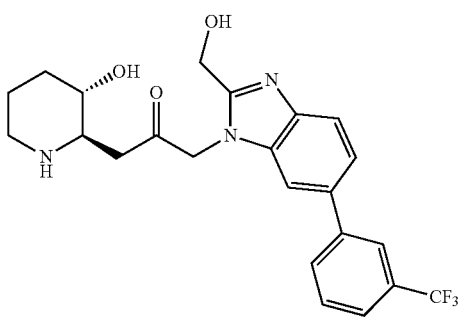 [SMILES: O=C(C[C@H]1NCCC[C@@H]1O)Cn1c(CO)nc2ccc(-c3cccc(C(F)(F)F)c3)cc21]

The title compound (14 mg, yield: 73%) was obtained in the same manner as in Example 55, with the exception that 4-bromo-2-fluoro-3-nitrobenzene was used instead of 4-bromo-1-fluoro-2-nitrobenzene in Step 55-1 of Example 55, and (3-trifluorophenyl)boronic acid was used instead of phenylboronic acid in Step 55-5 of Example 55.

$^1$H-NMR (500 MHz, DMSO-d$_6$): δ 8.00 (m, 3H), 7.69 (m, 3H), 7.57 (d, 1H), 5.46 (dd, 2H), 4.62 (s, 2H), 3.09 (m,1H), 3.03 (dd, 1H), 2.87 (d, 1H), 2.80 (m, 1H), 2.40 (m, 2H), 1.91 (m, 1H), 1.62 (d, 1H), 1.38 (m, 1H), 1.29 (m, 1H).

EXAMPLE 62

Preparation of (2R,3S)-2-(3-(5-(3-chlorophenyl)-3H-imidazo[4,5-b]pyridin-3-yl)-2-hydroxypropyl)piperidin-3-ol

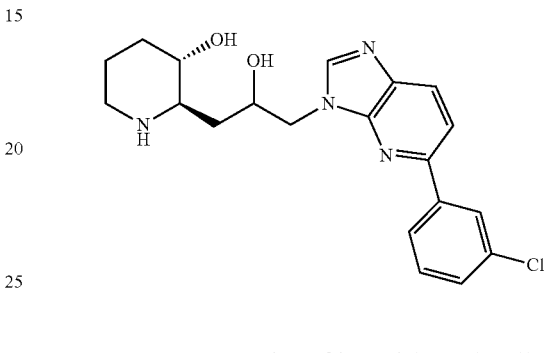

Step 62-1: Preparation of benzyl (2R,3S)-3-((tert-butyldimethylsilyl)oxy)-2-(3-(5-(3-chlorophenyl)-3H-imidazo[4,5-b]pyridin-3-yl)-2-hydroxypropyl)piperidine-1-carboxylate Benzyl (2R,3S)-3-((tert-butyldimethylsilyl)oxy)-2-(3-(5-(3-chlorophenyl)-3H-imidazo[4,5-b]pyridin-3-yl)-2-oxopropyl)piperidine-1-carboxylate (110 mg, 0.17 mmol) was dissolved in methyl alcohol (5 mL, 0.03 M) to which sodium borohydride (20 mg, 0.52 mmol) was added and then stirred at 0° C. for 30 minutes. Then, the mixture was stirred at room temperature for 1 hour. When the reaction was completed, the solvent was removed and the resulting mixture was diluted with ethyl acetate and washed with saturated sodium chloride solution. The organic layer was collected, dried over magnesium sulfate, filtered and concentrated under reduced pressure, and then purified by column chromatography (dichloromethane:methanol=10:1) to give the title compound (94 mg, yield: 85%).

Step 62-2: Preparation of (2R,3S)-2-(3-(5-(3-chlorophenyl)-3H-imidazo[4,5-b]pyridin-3-yl)-2-hydroxypropyl)piperidin-3-ol (2R,3S)-3-((tert-butyldimethylsilyl)oxy)-2-(3-(5-(3-chlorophenyl)-3H-imidazo[4,5-b]pyridin-3-yl)-2-hydroxypropyl)piperidine-1-carboxylate (37 mg, 0.06 mmol) obtained from Step 62-1 was dissolved in 6N hydrogen chloride solution (3 mL, 0.02 M) and then stirred under reflux for 1 hour. When the reaction was completed, the reaction solution was cooled to 0° C., neutralized (pH 7) with potassium carbonate and then extracted with a mixed solution of chloroform and a small amount of acetone. The organic layer was collected, dried over magnesium sulfate, filtered and concentrated under reduced pressure, and then recrystallized with diethylether to give the title compound (17 mg, yield: 76%).

$^1$H-NMR (500 MHz, DMSO-d$_6$): δ 8.42 (s, 1H), 8.21 (s, 1H), 8.16 (d, 1H), 8.12 (d, 1H), 7.93 (d, 1H), 7.53 (t, 1H), 7.49 (t, 1H), 4.64 (d, 1H), 4.37 (m, 1H), 4.22 (m, 2H), 2.97

(m, 1H), 2.80 (d, 1H), 2.44 (m, 1H), 2.38 (m, 1H), 1.85 (m, 2H), 1.56 (d, 1H), 1.37 (m, 2H), 1.21 (m, 1H).

EXAMPLE 63

Preparation of (2R,3S)-2-(3-(6-(3-chlorophenyl)-1H-benzo[d]imidazol-1-yl)-2-hydroxypropyl)piperidin-3-ol

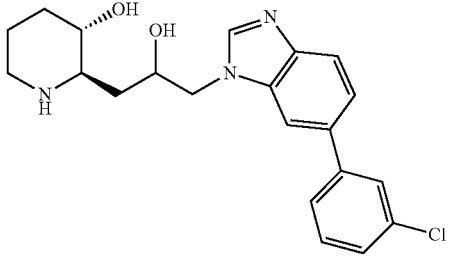 [SMILES: OC(C[C@H]1NCCC[C@@H]1O)Cn1cnc2ccc(-c3cccc(Cl)c3)cc21]

The title compound (14 mg, yield: 73%) was obtained in the same manner as in Example 62, with the exception that benzyl (2R,3S)-3-((tert-butyldimethylsilyl)oxy)-2-(3-(6-(3-chlorophenyl)-1H-benzo[d]imidazol-1-yl)-2-oxopropyl)piperidine-1-carboxylate was used instead of benzyl (2R,3S)-3-((tert-butyldimethylsilyl)oxy)-2-(3-(5-(3-chlorophenyl)-3H-imidazo[4,5-b]pyridin-3-yl)-2-oxopropyl)piperidine-1-carboxylate.

$^1$H-NMR (500 MHz, DMSO-$d_6$): δ 8.17 (s, 1H), 7.94 (s, 1H), 7.77 (s, 1H), 7.69 (d, 2H), 7.49 (m, 2H), 7.39 (m, 1H), 4.63 (d, 1H), 4.34 (dd, 1H), 4.16 (dd, 1H), 4.08 (m, 1H), 2.95 (m, 1H), 2.77 (d, 1H), 2.41 (m, 1H), 2.29 (m, 1H), 1.82 (m, 2H), 1,54(d, 1H), 1.36 (m, 1H), 1.24 (m, 2H).

EXPERIMENTAL EXAMPLE 1

PRS Enzyme Activity Inhibition Experiment

In order to confirm the biological activities of the compounds prepared in Examples, % inhibition or $IC_{50}$ values of PRS enzyme (phosphoribosylpyrophosphate synthetase enzyme) activities were calculated.

Specifically, the portion corresponding to PRS in cDNA of EPRS was subcloned, and the obtained high-purity PRS protein was purified and used in the experiment. The compounds (1 μM) prepared in Examples were added into the reaction buffer (20 mM $KPO_4$ (pH 7.4), 6 mM MgAc, 5 mM ATP, 400 mg/mL tRNA, 0.5 mM DTT, 20 mCi[$^3$H]proline (1 mCi/mL)) and allowed to react at 37° C. for 5 to 10 minutes. The reaction was terminated with 3M paper that was in advance dried by addition of 5% TCA. The radioactivity was measured using a liquid scintillation counter.

% Inhibition and $IC_{50}$ values of the respective compounds were calculated and analyzed using Microsoft Excel or Sigma Plot 8.0. The results are shown in Table 1 below. In Table 1, the results are divided into A, B and C according to the range of $IC_{50}$. The case where the derived $IC_{50}$ is 100 nM or less is represented by "A", the case where the $IC_{50}$ is 100 to 500 nM is represented by "B", and the case where the $IC_{50}$ is 500 nM or higher is represented by "C".

TABLE 1

| Example No. | PRS $IC_{50}$ |
| --- | --- |
| 1 | B |
| 2 | C |
| 3 | C |
| 4 | C |
| 5 | C |
| 6 | C |
| 7 | |
| 8 | C |
| 9 | C |
| 10 | C |
| 11 | C |
| 12 | C |
| 13 | C |
| 14 | B |
| 15 | C |
| 16 | B |
| 17 | B |
| 18 | C |
| 19 | B |
| 20 | C |
| 21 | B |
| 22 | C |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | B |
| 39 | B |
| 40 | C |
| 41 | A |
| 42 | B |
| 43 | B |
| 44 | A |
| 45 | A |
| 46 | A |
| 47 | A |
| 48 | B |
| 49 | A |
| 50 | B |
| 51 | B |
| 52 | C |
| 53 | C |
| 54 | B |
| 55 | C |
| 56 | C |
| 57 | A |
| 58 | A |
| 59 | A |
| 60 | A |
| 61 | B |
| 62 | A |
| 63 | B |

EXPERIMENTAL EXAMPLE 2

Cancer Cell Growth Inhibition Experiment

NCl-H460 cells, lung cancer cell lines, were cultured in 5% $CO_2$, 37° C. incubator using a flask for 75 cm$^2$ tissue culture. 96-well plates were used for the evaluation. These were prepared by differently applying at concentrations in the range of 6,000 to 12,000 cells/well according to the growth rate of the cell lines. The medium containing 5%

FBS were dispensed in 200 μL/well and used. The medium were cultured for 24 hours. After confirming the cell status and dispensing form of a 96-well plate under a microscope, they were used for subsequent experiments. The compounds were evaluated at concentrations of 100, 30, 10, 3, 1, 0.3, 0.03, 0.01 μM. After removing the existing medium, the compounds with various concentrations were treated in an amount of 200 μL/well. The compounds-treated plates were further cultured for 48 hours, and the cell viabilities were measured by MTT assay to calculate $IC_{50}$ values.

% Inhibition and $IC_{50}$ values of the respective compounds were calculated and analyzed using Sigma Plot 8.0. The results are shown in Table 2 below. In Table 2, the results are divided into A, B and C according to the range of $IC_{50}$. The case where the derived $IC_{50}$ is 3 μM or less is represented by "A", the case where the $IC_{50}$ is 3 to 10 μM is represented by "B", and the case where the $IC_{50}$ is 10 μM or higher is represented by "C".

TABLE 2

| Example No. | NCI-H460 $IC_{50}$ |
|---|---|
| 1 | C |
| 7 | C |
| 8 | C |
| 14 | C |
| 16 | C |
| 17 | C |
| 18 | C |
| 19 | C |
| 20 | C |
| 21 | C |
| 22 | C |
| 23 | C |
| 24 | B |
| 25 | A |
| 26 | B |
| 27 | A |
| 28 | B |
| 29 | A |
| 30 | B |
| 31 | B |
| 32 | A |
| 33 | B |
| 34 | B |
| 35 | B |
| 36 | B |
| 37 | C |
| 38 | C |
| 39 | C |
| 40 | C |
| 41 | C |
| 43 | A |
| 44 | A |
| 45 | B |
| 46 | A |
| 47 | A |
| 48 | C |
| 49 | A |
| 50 | C |
| 51 | C |
| 54 | C |
| 56 | C |
| 57 | B |
| 58 | B |
| 59 | A |
| 60 | C |
| 61 | A |
| 62 | C |
| 63 | C |

What is claimed is:

1. A compound of the following Chemical Formula 1, or a pharmaceutically acceptable salt thereof:

[Chemical Formula 1]

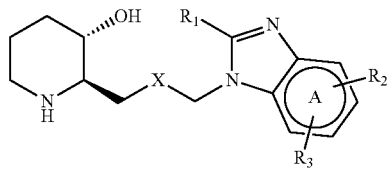

wherein:
A is a benzene ring, or a pyridine ring,
X is CO, or CHOH,
$R_1$ is hydrogen, or $C_{1-4}$ hydroxyalkyl,
$R_2$ is phenyl, pyrazolyl, pyridin-2-onyl, pyrrolidinyl, or thiazolyl,
wherein $R_2$ is unsubstituted or substituted by one or two substituents each independently selected from the group consisting of $C_{1-4}$ alkyl, $C_{1-4}$ alkoxy, $C_{1-4}$ haloalkyl, halogen and cyano, and
$R_3$ is hydrogen, or $C_{1-4}$ alkyl.

2. The compound or a pharmaceutically acceptable salt thereof according to claim 1 wherein
A, together with an imidazole ring fused to A, forms a structure of

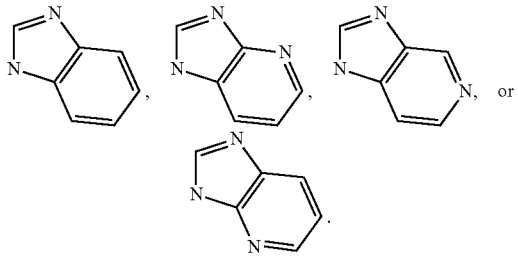

3. The compound or a pharmaceutically acceptable salt thereof according to claim 1 wherein $R_1$ is hydrogen, or hydroxymethyl.

4. The compound or a pharmaceutically acceptable salt thereof according to claim 1 wherein $R_2$ is a phenyl unsubstituted or substituted by one or two substituents each independently selected from $C_{1-4}$ alkyl, $C_{1-4}$ alkoxy, $C_{1-4}$ haloalkyl, halogen and cyano; an unsubstituted pyrazolyl; an unsubstituted pyridin-2-onyl; an unsubstituted pyrrolidinyl; or an unsubstituted thiazolyl.

5. The compound or a pharmaceutically acceptable salt thereof according to claim 1 wherein $R_2$ is unsubstituted or substituted by one or two substituents each independently selected from methyl, methoxy, trifluoromethyl, fluoro, chloro and cyano.

6. The compound or a pharmaceutically acceptable salt thereof according to claim 1 wherein $R_3$ is hydrogen, or methyl.

7. The compound or a pharmaceutically acceptable salt thereof according to claim 1 wherein
A is benzene ring,
X is CO, or CHOH,
$R_1$ is hydrogen, or $C_{1-4}$ hydroxyalkyl,
$R_2$ is phenyl, pyrazolyl, pyridin-2-onyl, or thiazolyl,
wherein $R_2$ is unsubstituted or substituted by one or two substituents each independently selected from the group consisting of $C_{1-4}$ alkyl, $C_{1-4}$ alkoxy, $C_{1-4}$ haloalkyl, halogen and cyano; and
$R_3$ is hydrogen, or $C_{1-4}$ alkyl.

8. The compound or a pharmaceutically acceptable salt thereof according to claim 1 wherein A, together with an imidazole ring fused to A, forms

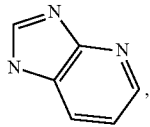

X is CO,
$R_1$ is hydrogen,
$R_2$ is phenyl, or pyrrolidinyl,
wherein $R_2$ is unsubstituted or substituted by one or two substituents each independently selected from $C_{1-4}$ haloalkyl and halogen, and
$R_3$ is hydrogen.

9. The compound or a pharmaceutically acceptable salt thereof according to claim 1 wherein A, together with an imidazole ring fused to A, forms

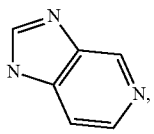

X is CO,
$R_1$ is hydrogen,
$R_2$ is phenyl, or pyrrolidinyl,
wherein $R_2$ is unsubstituted or substituted by one or two substituents each independently selected from the group consisting of $C_{1-4}$ haloalkyl and halogen, and
$R_3$ is hydrogen.

10. The compound or a pharmaceutically acceptable salt thereof according to claim 1 wherein A, together with an imidazole ring fused to A, forms

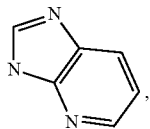

X is CO, or CHOH,
$R_1$ is hydrogen,
$R_2$ is phenyl,
wherein $R_2$ is substituted by $C_{1-4}$ haloalkyl, or halogen, and
$R_3$ is hydrogen.

11. The compound or a pharmaceutically acceptable salt thereof according to claim 1 wherein the compound of Chemical Formula 1 is selected from the group consisting of:

1) 1-((2R,3S)-3-hydroxypiperidin-2-yl)-3-(4-phenyl-1H-benzo[d]imidazol-1-yl)propan-2-one,
2) 1-(4-(3-fluorophenyl)-1H-imidazo[4,5-c]pyridin-1-yl)-3-((2R,3S)-3-hydroxypiperidin-2-yl)propan-2-one,
3) 1-(4-(3-chlorophenyl)-1H-imidazo[4,5-c]pyridin-1-yl)-3-((2R,3S)-3-hydroxypiperidin-2-yl)propan-2-one,
4) 1-((2R,3S)-3-hydroxypiperidin-2-yl)-3-(4-(3-(trifluoromethyl)phenyl)-1H-imidazo[4,5-c]pyridin-1-yl)propan-2-one,
5) 1-(4-(3-chloro-5-fluorophenyl)-1H-imidazo[4,5-c]pyridin-1-yl)-3-((2R,3S)-3-hydroxypiperidin-2-yl)propan-2-one,
6) 1-(4-(3,5-dichlorophenyl)-1H-imidazo[4,5-c]pyridin-1-yl)-3-((2R,3S)-3-hydroxypiperidin-2-yl)propan-2-one,
7) 1-((2R,3S)-3-hydroxypiperidin-2-yl)-3-(4-(pyrrolidin-1-yl)-1H-imidazo[4,5-c]pyridin-1-yl)propan-2-one,
8) 1-((2R,3S)-3-hydroxypiperidin-2-yl)-3-(5-phenyl-1H-benzo[d]imidazol-1-yl)propan-2-one,
9) 1-(5-(2-fluorophenyl)-1H-imidazo[4,5-b]pyridin-1-yl)-3-((2R,3S)-3-hydroxypiperidin-2-yl)propan-2-one,
10) 1-(5-(3-fluorophenyl)-1H-imidazo[4,5-b]pyridin-1-yl)-3-((2R,3S)-3-hydroxypiperidin-2-yl)propan-2-one,
11) 1-(5-(4-fluorophenyl)-1H-imidazo[4,5-b]pyridin-1-yl)-3-((2R,3S)-3-hydroxypiperidin-2-yl)propan-2-one,
12) 1-(5-(3-chlorophenyl)-1H-imidazo[4,5-b]pyridin-1-yl)-3-((2R,3S)-3-hydroxypiperidin-2-yl)propan-2-one,
13) 1-((2R,3S)-3-hydroxypiperidin-2-yl)-3-(5-(3-(trifluoromethyl)phenyl)-1H-imidazo[4,5-b]pyridin-1-yl)propan-2-one,
14) 1-(6-(3-chlorophenyl)-3H-imidazo[4,5-b]pyriclin-3-yl)-3-((2R,3S)-3-hydroxypiperidin-2-yl)propan-2-one,
15) 1-((2R,3S)-3-hydroxypiperidin-2-yl)-3-(6-(3-(trifluoromethyl)phenyl)-3H-imidazo[4,5-b]pyridin-3-yl)propan-2-one,
16) 1-(5-(3-fluorophenyl)-4-methyl-1H-benzo[d]imidazol-1-yl)-3-((2R,3S)-3-hydroxypipericlin-2-yl)propan-2-one,
17) 1-(5-(3-chlorophenyl)-4-methyl-1H-benzo[d]imidazol-1-yl)-3-((2R,3S)-3-hydroxypipericlin-2-yl)propan-2-one,
18) 1-(5-(2-chlorophenyl)-4-methyl-1H-benzo[d]imidazol-1-yl)-3-((2R,3S)-3-hydroxypipericlin-2-yl)propan-2-one,
19) 1-(5-(4-chlorophenyl)-4-methyl-1H-benzo[d]imidazol-1-yl)-3-((2R,3S)-3-hydroxypipericlin-2-yl)propan-2-one,
20) 3-(1-(3-((2R,3S)-3-hydroxypiperidin-2-yl)-2-oxopropyl)-4-methyl-1H-benzo[d]imidazol-5-yl)benzonitrile,
21) 1-((2R,3S)-3-hydroxypiperidin-2-yl)-3-(4-methyl-5-(3-(trifluoromethyl)phenyl)-1H-benzo[d]imidazol-1-yl)propan-2-one,
22) 1-((2R,3S)-3-hydroxypiperidin-2-yl)-3-(5-(3-methoxyphenyl)-4-methyl-1H-benzo[d]imidazol-1-yl)propan-2-one,
23) 1-((2R,3S)-3-hydroxypiperidin-2-yl)-3-(4-methyl-5-(thiazol-4-yl)-1H-benzo[d]imidazol-1-yl)propan-2-one,
24) 1-((2R,3S)-3-hydroxypiperidin-2-yl)-3-(6-phenyl-1H-benzo[d]imidazol-1-yl)propan-2-one,
25) 1-(6-(3-fluorophenyl)-1H-benzo[d]imidazol-1-yl)-3-((2R,3S)-3-hydroxypiperidin-2-yl)propan-2-one,
26) 1-(6-(2-chlorophenyl)-1H-benzo[d]imidazol-1-yl)-3-((2R,3S)-3-hydroxypiperidin-2-yl)propan-2-one,
27) 1-(6-(3-chlorophenyl)-1H-benzo[d]imidazol-1-yl)-3-((2R,3S)-3-hydroxypiperidin-2-yl)propan-2-one,
28) 1-(6-(4-chlorophenyl)-1H-benzo[d]imidazol-1-yl)-3-((2R,3S)-3-hydroxypiperidin-2-yl)propan-2-one,
29) 1-((2R,3S)-3-hydroxypiperidin-2-yl)-3-(6-(3-(trifluoromethyl)phenyl)-1H-benzo[d]imidazol-1-yl)propan-2-one,
30) 1-((2R,3S)-3-hydroxypiperidin-2-yl)-3-(6-(m-tolyl)-1H-benzo[d]imidazol-1-yl)propan-2-one,
31) 1-(6-(3,5-dichlorophenyl)-1H-benzo[d]imidazol-1-yl)-3-((2R,3S)-3-hydroxypiperidin-2-yl)propan-2-one, 32) 1-(6-(3-chloro-5-fluorophenyl)-1H-benzo[d]imidazol-1-yl)-3-((2R,3S)-3-hydroxypiperidin-2-yl)propan-2-one,
33) 1-(6-(3-chloro-4-fluorophenyl)-1H-benzo[d]imidazol-1-yl)-3-((2R,3S)-3-hydroxypiperidin-2-yl)propan-2-one,
34) 1-(6-(3-chloro-5-methylphenyl)-1H-benzo[d]imidazol-1-yl)-3-((2R,3S)-3-hydroxypiperidin-2-yl)propan-2-one,
35) 1-(6-(3-chloro-5-methoxyphenyl)-1H-benzo[d]imidazol-1-yl)-3-((2R,3S)-3-hydroxypiperidin-2-yl)propan-2-one,
36) 3-chloro-5-(1-(3-((2R,3S)-3-hydroxypiperidin-2-yl)-2-oxopropyl)-1H-benzo[d]imidazol-6-yl)benzonitrile,
37) 1-(6-(1H-pyrazol-4-yl)-1H-benzo[d]imidazol-1-yl)-3-((2R,3S)-3-hydroxypiperidin-2-yl)propan-2-one,
38) 1-(6-(1H-pyrazol-3-yl)-1H-benzo[d]imidazol-1-yl)-3-((2R,3S)-3-hydroxypiperidin-2-yl)propan-2-one,
39) 1-((2R,3S)-3-hydroxypiperidin-2-yl)-3-(6-(thiazol-4-yl)-1H-benzo[d]imidazol-1-yl)propan-2-one,
40) 5-(1-(3-((2R,3S)-3-hydroxypiperidin-2-yl)-2-oxopropyl)-1H-benzo[d]imidazol-6-yl)pyridin-2(1H)-one,
41) 1-(6-(3-chlorophenyl)-1H-imidazo[4,5-b]pyridin-1-yl)-3-((2R,3S)-3-hydroxypiperidin-2-yl)propan-2-one,
42) 1-((2R,3S)-3-hydroxypiperidin-2-yl)-3-(6-(3-(trifluoromethyl)phenyl)-1H-imidazo[4,5-b]pyridin-1-yl)propan-2-one,
43) 1-(5-(2-fluorophenyl)-3H-imidazo[4,5-b]pyridin-3-yl)-3-((2R,3S)-3-hydroxypiperidin-2-yl)propan-2-one,
44) 1-(5-(3-fluorophenyl)-3H-imidazo[4,5-b]pyridin-3-yl)-3-((2R,3S)-3-hydroxypiperidin-2-yl)propan-2-one,
45) 1-(5-(4-fluorophenyl)-3H-imidazo[4,5-b]pyridin-3-yl)-3-((2R,3S)-3-hydroxypiperidin-2-yl)propan-2-one,
46) 1-(5-(3-chlorophenyl)-3H-imidazo[4,5-b]pyridin-3-yl)-3-((2R,3S)-3-hydroxypiperidin-2-yl)propan-2-one,
47) 1-((2R,3S)-3-hydroxypiperidin-2-yl)-3-(5-(3-(trifluoromethyl)phenyl)-3H-imidazo[4,5-b]pyridin-3-yl)propan-2-one,
48) 1-((2R,3S)-3-hydroxypiperidin-2-yl)-3-(7-phenyl-1H-benzo[d]imidazol-1-yl)propan-2-one,
49) 1-(7-(3-fluorophenyl)-1H-benzo[d]imidazol-1-yl)-3-((2R,3S)-3-hydroxypiperidin-2-yl)propan-2-one,
50) 1-(7-(3-chlorophenyl)-1H-benzo[d]imidazol-1-yl)-3-((2R,3S)-3-hydroxypiperidin-2-yl)propan-2-one,
51) 1-(7-(4-chlorophenyl)-1H-benzo[d]imidazol-1-yl)-3-((2R,3S)-3-hydroxypiperidin-2-yl)propan-2-one,
52) 1-((2R,3S)-3-hydroxypiperidin-2-yl)-3-(7-(2-(trifluoromethyl)phenyl)-1H-benzo[d]imidazol-1-yl)propan-2-one,
53) 1-((2R,3S)-3-hydroxypiperidin-2-yl)-3-(7-(3-(trifluoromethyl)phenyl)-1H-benzo[d]imidazol-1-yl)propan-2-one,
54) 1-((2R,3S)-3-hydroxypiperidin-2-yl)-3-(7-(4-(trifluoromethyl)phenyl)-1H-benzo[d]imidazol-1-yl)propan-2-one,
55) 1-(2-(hydroxymethyl)-5-phenyl-1H-benzo[d]imidazol-1-yl)-3-((2R,3S)-3-hydroxypiperidin-2-yl)propan-2-one,
56) 1-(5-(3-fluorophenyl)-2-(hydroxymethyl)-1H-benzo[d]imidazol-1-yl)-3-((2R,3S)-3-hydroxypiperidin-2-yl)propan-2-one,
57) 1-(2-(hydroxymethyl)-6-phenyl-1H-benzo[d]imidazol-1-yl)-3-((2R,3S)-3-hydroxypiperidin-2-yl)propan-2-one,
58) 1-(6-(2-fluorophenyl)-2-(hydroxymethyl)-1H-benzo[d]imidazol-1-yl)-3-((2R,3S)-3-hydroxypiperidin-2-yl)propan-2-one,
59) 1-(6-(3-fluorophenyl)-2-(hydroxymethyl)-1H-benzo[d]imidazol-1-yl)-3-((2R,3S)-3-hydroxypiperidin-2-yl)propan-2-one,
60) 1-(6-(4-fluorophenyl)-2-(hydroxymethyl)-1H-benzo[d]imidazol-1-yl)-3-((2R,3S)-3-hydroxypiperidin-2-yl)propan-2-one,
61) 1-(2-(hydroxymethyl)-6-(3-(trifluoromethyl)phenyl)-1H-benzo[d]imidazol-1-yl)-3-((2R,3S)-3-hydroxypiperidin-2-yl)propan-2-one,
62) (2R,3S)-2-(3-(6-(3-chlorophenyl)-1H-benzo[d]imidazol-1-yl)-2-hydroxypropyhpiperidin-3-ol, and
63) (2R,3S)-2-(3-(5-(3-chlorophenyl)-3H-imidazo[4,5-b]pyridin-3-yl)-2-hydroxypropyhpiperidin-3-ol.

12. A pharmaceutical composition for the inhibition of prolyl-tRNA synthetase, comprising the compound according to claim 1 or the pharmaceutically acceptable salt thereof.

* * * * *